(12) United States Patent
Ueda et al.

(10) Patent No.: US 11,135,243 B2
(45) Date of Patent: Oct. 5, 2021

(54) COMPOSITION FOR TREATMENT OF DAMAGED PART

(71) Applicant: SHED Tech Corporation, Tokushima (JP)

(72) Inventors: Minoru Ueda, Tokushima (JP); Yoichi Yamada, Tokushima (JP); Katsumi Ebisawa, Tokushima (JP); Akihito Yamamoto, Tokushima (JP); Kiyoshi Sakai, Tokushima (JP); Kohki Matsubara, Tokushima (JP); Hisashi Hattori, Tokushima (JP); Masahiko Sugiyama, Tokushima (JP); Takanori Inoue, Tokushima (JP)

(73) Assignee: SHED Tech Corporation, Tokushima (JP)

( * ) Notice: Subject to any disclaimer, the term of this patent is extended or adjusted under 35 U.S.C. 154(b) by 0 days.

(21) Appl. No.: 16/043,395

(22) Filed: Jul. 24, 2018

(65) Prior Publication Data
US 2018/0325946 A1 Nov. 15, 2018

Related U.S. Application Data

(62) Division of application No. 13/637,107, filed as application No. PCT/JP2011/057412 on Mar. 25, 2011, now abandoned.

(60) Provisional application No. 61/437,697, filed on Jan. 31, 2011, provisional application No. 61/410,370, filed on Nov. 5, 2010, provisional application No. 61/317,713, filed on Mar. 26, 2010.

(30) Foreign Application Priority Data

Dec. 1, 2010 (JP) ................................ 2010-267962
Feb. 23, 2011 (JP) ................................ 2011-037028

(51) Int. Cl.
| | |
|---|---|
| *A61K 35/12* | (2015.01) |
| *A61K 35/545* | (2015.01) |
| *A61K 35/28* | (2015.01) |
| *A61K 35/30* | (2015.01) |
| *A61K 35/32* | (2015.01) |
| *C12N 5/0775* | (2010.01) |
| *A61K 38/30* | (2006.01) |
| *A61K 38/18* | (2006.01) |

(52) U.S. Cl.
CPC ............ *A61K 35/12* (2013.01); *A61K 35/28* (2013.01); *A61K 35/30* (2013.01); *A61K 35/32* (2013.01); *A61K 35/545* (2013.01); *A61K 38/18* (2013.01); *A61K 38/1833* (2013.01); *A61K 38/1841* (2013.01); *A61K 38/1858* (2013.01); *A61K 38/1866* (2013.01); *A61K 38/30* (2013.01); *C12N 5/0664* (2013.01)

(58) Field of Classification Search
None
See application file for complete search history.

(56) References Cited

U.S. PATENT DOCUMENTS

| | | | |
|---|---|---|---|
| 2007/0274958 A1* | 11/2007 | Shi ...................... | C12N 5/0618 424/93.7 |
| 2009/0035376 A1 | 2/2009 | Carinci et al. | |
| 2009/0053182 A1 | 2/2009 | Ichim et al. | |
| 2011/0177041 A1 | 7/2011 | Nakashima et al. | |

FOREIGN PATENT DOCUMENTS

| | | | |
|---|---|---|---|
| JP | 2002281962 A | 10/2002 | |
| JP | 2010505849 A | 2/2010 | |
| KR | 20090043559 A | 5/2009 | |
| WO | 02086108 A1 | 10/2002 | |
| WO | 2008020815 A1 | 2/2008 | |
| WO | 2008024996 A2 | 2/2008 | |
| WO | WO-2008020815 A1 * | 2/2008 | ........... C12N 5/0662 |
| WO | WO-2008024996 A2 * | 2/2008 | ........... C12N 5/0667 |
| WO | 2008060374 A2 | 5/2008 | |
| WO | 2009072527 A1 | 6/2009 | |

(Continued)

OTHER PUBLICATIONS

Iohara et al. "A novel stem cell source for vasculogenesis in ischemia: subtraction of side population cells from dental pulp", Stem Cells 26: 2408-2418, 2008 (Year: 2008).*
Gandia et al. "Human dental pulp stem cells improve left ventricular function, induce angiogenesis, and reduce infarct size in rats with acute myocardial infarction." Stem cells 26 (3): 638-645, 2008 (Year: 2008).*
Tran-Hung et al. "Quantification of angiogenic growth factors released by human dental cells after injury." Archives of Oral Biology 53 (1): 9-13, 2008 (Year: 2008).*
Nosrat et al. "Dental pulp cells provide neurotrophic support for dopaminergic neurons and differentiate into neurons in vitro; implications for tissue engineering and repair in the nervous system." European Journal of Neuroscience 19.9 (2004): 2388-2398. (Year: 2004).*

(Continued)

*Primary Examiner* — Emily A Cordas
(74) *Attorney, Agent, or Firm* — Banner & Witcoff, Ltd.

(57) ABSTRACT

The present invention provides a damaged part treatment composition for repairing a damaged part of a target tissue that includes a stem cell-conditioned medium obtained by culturing stem cells; a damaged part treatment method for repairing or restoring a damaged part of a target tissue that includes administering the damaged part treatment composition to a patient having the target tissue for the damaged part treatment composition in an amount therapeutically effective for repairing the damaged part of the target tissue; a method of treating cerebral infarction that includes administering the damaged part treatment composition to a cerebral infarct patient in an amount effective for repairing a damaged part of the brain; and a method of treating a CNS disease that includes administering, as a CNS disease treatment composition, the damaged part treatment composition to a CNS disease patient in a therapeutically effective amount.

19 Claims, 27 Drawing Sheets

(56) References Cited

FOREIGN PATENT DOCUMENTS

| WO | 2010021412 A1 | 2/2010 |
| WO | 2011/118795 A1 | 9/2011 |

OTHER PUBLICATIONS

Iohara et al. "Side Population Cells Isolated from Porcine Dental Pulp Tissue with Self-Renewal and Multipotency for Dentinogenesis, Chondrogenesis, Adipogenesis, and Neurogenesis" Stem Cells 2006; 24:2493-2503.

Sakai et al. "Human dental pulp-derived stem cells promote locomotor recovery after complete transection of the rat spinal cord by multiple neuroregenerative mechanisms". J Clin Invest; 2012; 122(1):80-90.

English Translation of Office Action issued for corresponding Japanese Patent Application No. 2012-507105, dated Mar. 24, 2015.

Cheng, Songming, "Combination therapy with intranasal NGF and electroacupuncture enhanced cell proliferation and survival in rats after stroke" Neumlog;cal Research, Sep. 2009, pp. 753-758, vol. 31.

Greenberg, David A., "Growth Factors and Stroke," The Journal of the American Society for Experimental NeuroTherapeutics, Oct. 2006, pp. 458-465, vol. 3, The American Society for Experimental NeuroTherapeutics, Inc.

Wang, Zhao-Lu, "Intranasally delivered bFGF enhances neurogenesis in adult rats following cerebral ischemia," Neuroscience Letters, Sep. 10, 2008, pp. 30-35, vol. 446, Elsevier Ireland Ltd.

Office Action issued for corresponding Japanese Patent Application No. 2012-507105, dated Oct. 20, 2015.

Journal of the Japanese Society of Conservative Dentistry, 2002, vol. 45, No. 6, p. 1131-1139.

Arch.Histol. Cytol., 2009, vol. 72, No. 1, p. 51-64.

Journal of Japan Tissue Culture Society for Dental Research, Feb. 1, 2010, vol. 19, No. 1, p. 37-38, Description of article considered in English translation of Japan Patent Application 2012-507105 Decision of Refusal dated Oct. 13, 2015.

English Translation of Office Action issued for corresponding Japanese Patent Application No. 2006-008932, dated Dec. 13, 2016.

Kyoko Harada, et al., "Alterations in Deciduous Dental Pulp Cells Cultured with Serum-free Medium," Journal of Hard Tissue Biology, 2015, Bol. 24, No. 1, p. 17-22.

English Translation of Office Action issued for corresponding Korean Patent Application No. 2012-7027806, dated Dec. 21, 2016.

English Translation of Office Action issued for corresponding Japanese Patent Application No. 2016-008932, dated Jul. 25, 2017.

Chaudhry, M.A. et al., Basal medium composition and serum or serum replacement concentration influences on the maintenance of murine embryonic stem cells, Cytotechnology, 2008, vol. 58, pp. 173-179.

Picou, A.A. et al, Characterization of Bovine Adult-Derived Adipose Stem Cells for Use in Nuclear Transfer, Reproduction, Fertility and Development, 2010, vol. 22, Article 394, pp. 353-354.

Arthur, Agnes, et al., "Adult Human Dental Pulp Stem Cells Differentiate Toward Functionally Active Neurons Under Appropriate Environmental Cues," Stem Cells, 2008, vol. 26, pp. 1787-1795.

Chung, Jin Ho, et al., "Regulations of Collagen Synthesis by Ascorbic Acid, Transforming Growth Factor $\hat{I}^2$ and Interferon-$\hat{I}^3$ in Human Dermal Febroblasts Cultured in Three-Dimensional Collagen Gel are Photoaging-and Aging-Independent," Journal of Dermatological Science, 1997, vol. 15, pp. 188-200.

Fitzpatrick, Richard, et al., "Reversal of Photodamage with Topical Growth Factors: A Pilot Study, Journal of Cosmetic and Laser Therapy," 2003, vol. 5, pp. 25-34.

Gandia, Carolina, et al., "Human Dental Pulp Stem Cells Improve Left Ventricular Function, Induce Angiogenesis, and Reduce Infarct Size in Rats with Acute Myocardial Infarction," Stem Cells, 2008, vol. 26, pp. 638-645.

Gronthos, S., et al., "Postnatal Human Dental Pulp Stem Cells (DPSCs) in vitro and in vivo," Proceedings of the National Academy of Sciences, Dec. 5, 2000, vol. 97, No. 25, pp. 13625-13630.

He Huixia, et al., "Effects of FGF2 and TGF$\hat{I}^2$1 on the Differentiation of Human Dental Pulp Stem Cells in vitro," Cell Biology International, 2008, pp. 827-834.

Hsien-Cheng Huang, Anderson, et al., "Putative Dental Pulp-Derived Stem/Stromal Cells Promote Proliferation and Differentiation of Endogenous Neural Cells in the Hippocampus of Mice," Stem Cells, 2008, vol. 26, pp. 2654-2663.

Iohara, Koichiro, et al., "A Novel Stem Cell Source for Vasculogenesis in Ischemia: Subtraction of Side Population Cells from Dental Pulp," Stem Cells, 2008, vol. 26, pp. 2408-2418.

Jettanacheawchankit, Suwimon, et al., "Acemannan Stimulates Gengival Fibroblast Proliferation; Expressions of Keratinocyte Growth Factor-1, Vascular Endothelial Growth Factor, and Type 1 Collagen; and Wound Healing," Journal of Pharmacological Sciences, 2009, vol. 109, pp. 525-531.

Keirstead, Hans, S., et al., "Human Embryonic Stem Cell-Derived Oligodendrocyte Progenitor Cell Transplants Remyelinate and Restore Locomotion After Spinal Cord Injury," The Journal of Neuroscience, May 11, 2005, vol. 25, pp. 4694-4705.

Matsubara, Kohki, et al., "Verification of the Nerve Regeneration Effect of a Conditioned Medium from Dental Pulp Stem Cells," Journal of the Japanese Society for Regenerative Medicine, Feb. 2011, vol. 10, p. 212.

Miura, Masako, et al., "SHED: Stem Cells from Human Exfoliated Deciduous Teeth," Proceedings of the National Academy of Sciences, May 13, 2003, vol. 100, No. 10, pp. 5807-5812.

Safavi, Seyed Mohammadreza, et al., "Effects of Low-Level He—Ne Laser Irradiation on the Gene Expression of IL-1$\hat{I}^2$, TNF-$\hat{I}\pm$, IFN-$\hat{I}^3$, TGF-$\hat{I}^2$, , bFGF, and PDGE in Rat's Gingiva," Lasers in Medical Science, 2008, vol. 23, pp. 331-335.

Okada, Yohei, et al., "Spatiotemporal Recapitulation of Central Nervous System Development by Murine Embryonic Stem Cell-Derived Neural Stem/Progenitor Cells," Stem Cells, 2008, vol. 26, pp. 3086-3098.

Okano, Hideyuki, et al., "Neural Stem Cells and Regeneration of Injured Spinal Cord," Kidney International, 2005, vol. 68, pp. 1927-1931.

Robey, Pamela Gehron, "Stem Cells Near the Century Mark," The Journal of Clinical Investigation, Jun. 2000, vol. 105, No. 11, pp. 1489-1491.

Saygun, Isil, et al., "Effects of Laser Irradiation on the Release of Basic Fibroblast Growth Factor (bFGF), Insulin Like Growth Factor-1 (IGF-1), and Receptor of IGF-1 (IGFBP3) from Gingival Fibroblasts," Lasers in Medical Science, 2008, vol. 23, pp. 211-215.

Extended European Search Report, dated Jul. 24, 2013, in corresponding European Patent Application No. 11759599.1.

Timmers, Leo et al., "Reduction of myocardial infarct size by human mesenchymal stem cell conditioned medium", Stem Cell Research (2008), No. 1, pp. 129-137.

Sakai et al. "Human dental pulp-derived stem cells promote locomotor recovery after complete transection of the rat spinal cord by multiple neuro-regenerative mechanisms" The Journal of clinical investigation 122(1 ): 80-90, 2012.

Kim et al. "Antiwrinkle effect of adipose-derived stem cell: activation of dermal fibroblast by secretory factors." Journal of Dermatological Science 53(2): 96-1 02, 2009.

Tran-Hung et al. "Quantification of angiogenic growth factors released by human dental cells after injury." Archives of Oral Biology 53 (1 ): 9-13, 2008.

Pierdomenico et al. "Multipotent mesenchymal stem cells with immunosuppressive activity can be easily isolated from dental pulp", Transplantation 80: 836-42, 2005.

What are adult stem cells?. In Stem Cell Information [World Wide Web site]. Bethesda, MD: National Institutes of Health, U.S. Department of Health and Human Services, 2012 [cited Friday, Sep. 19, 2014] Available at <http://stemcells.nih.gov/info/basics/pp./basics4.aspx>.

(56) References Cited

OTHER PUBLICATIONS

English translation of the Decision of Refusal in corresponding Japanese Application No. 2012-507105, Oct. 13, 2015 drafting date.

* cited by examiner $$BIC(\%) = \frac{\text{total length of bone contact}}{\text{total length of implant surfaces}} \times 100$$

Case 1.Macro view

18W

56,M

Case 1

Panoromic view    18W

3 male beagle dogs
(ca. 1 year old, ca.15kgs)

extraction of $M_1$ and $_2M$

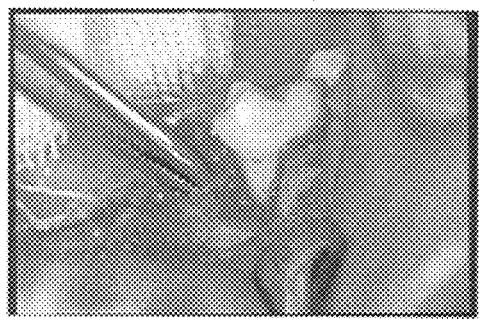

・2-wall bony defects at the mesial sites of $M_2$s and at the distal sites of $PM_4$s
  5 mm (depth), 3mm (width), 3mm(length)

・fill the defects with dental materials in order to ensure bacterial infection

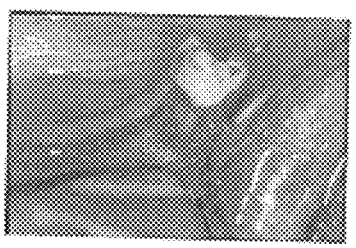

2.GTR

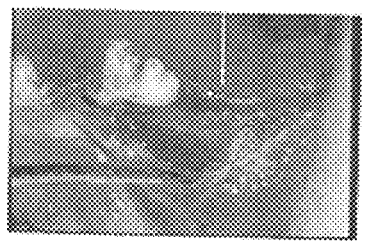

・Bio-resolvable periodontal membrane
(GC membrane®, GC, Tokyo, Japan)
Poly-lactic acids-co-glycolic acid(PLGA)

・Bio-resolvable suture
(Vicryl, Ethicon, USA)

FIG.18
3. MSC
4. GF
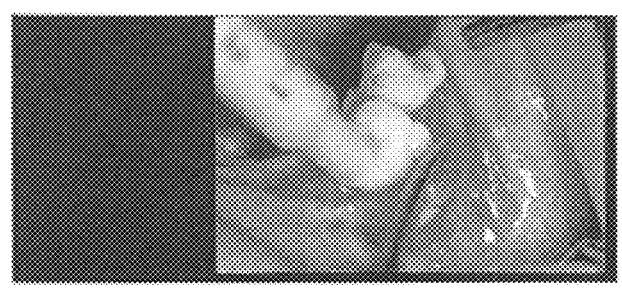
FIG.19
$N_1$-JE: length of the epithelial down growth
$N_2$-NC: length of the new cementum
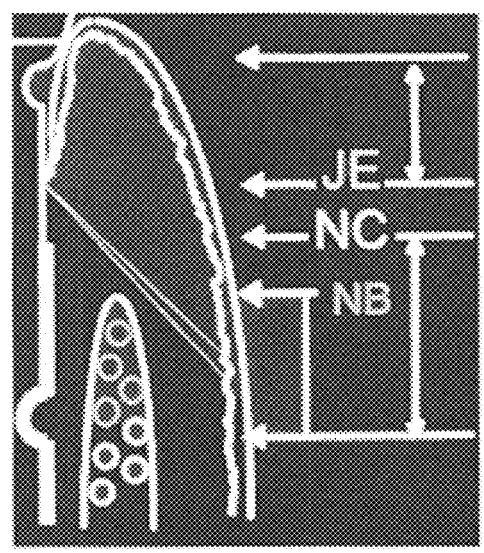

Pre.treatment

G.F+collagen sponge

16w

PBS:phosphate buffer saline, pMCAO: permanent focal cerebral ischemia
SH-CM:SHED-derived conditioned medium

FIG.37
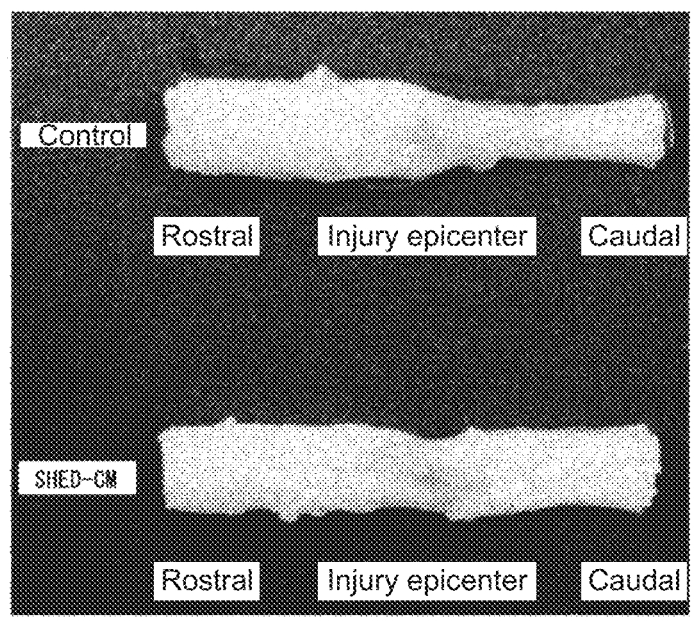
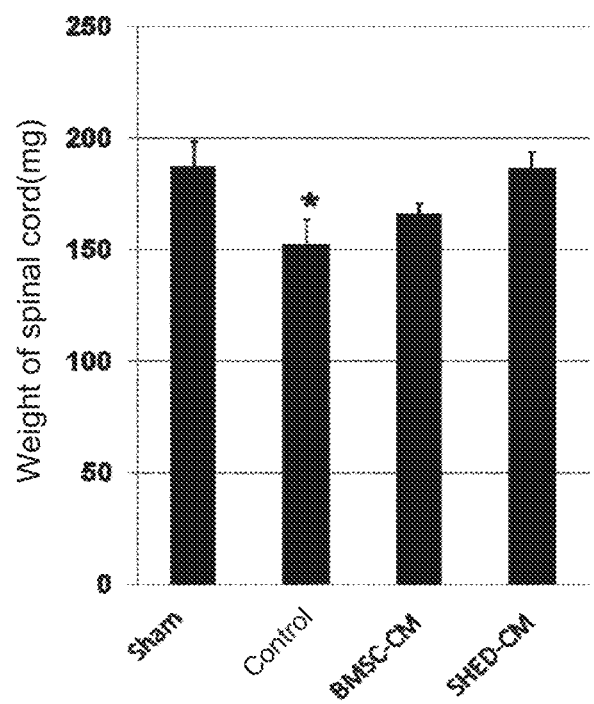

COMPOSITION FOR TREATMENT OF DAMAGED PART

RELATED APPLICATION DATA

This application is a Divisional of co-pending U.S. Utility application Ser. No. 13/637,106, filed on Dec. 13, 2012, which is a National Stage Application under 35 U.S.C. 371 of co-pending PCT application PCT/JP2011/057412 designating the United States and filed Mar. 25, 2011; which claims the benefit of JP patent application number 2011-037028 and filed Feb. 23, 2011; which claims the benefit of U.S. Provisional application No. 61/437,697 and filed Jan. 31, 2011; which claims the benefit of JP patent application No. 2010-267962 and filed Dec. 1, 2010; which claims the benefit of U.S. Provisional application No. 61/410,370 and filed Nov. 5, 2010; which claims the benefit of U.S. Provisional application No. 61/317,713 and filed Mar. 26, 2010 each of which are hereby incorporated by reference in their entireties.

TECHNICAL FIELD

The present invention relates to a composition for treatment of a damaged part, and a treatment method using the same.

Regenerative medicine utilizing stem cells attracts attention as a versatile alternative technique for diseases that are hard to treat by conventional medicine.

Regenerative medicine using stem cells is a promising tool in a new clinical platform for a whole spectrum of intractable diseases. Various stem cells have been reported, including embryonic stem cells (ES cells), induced pluripotent stem cells (iPS cells) and somatic stem cells. Among somatic stem cells, mesenchymal stem cells (MSCs) isolated from various tissues including bone marrow, adipose tissue, skin, umbilical cord and placenta have been used in particular in clinical applications in skin regeneration. However, bone marrow aspiration is an invasive and painful procedure for the donor. In addition, the number, and proliferation and differentiation potential of bone marrow stem cells (BMSCs) decline with increasing age.

There are many diseases to which regenerative medicine is applicable or expected to be applicable, and various researches for clinical application thereof have been carried out. A neurological disorder, particularly an intractable neurological disorder such as spinal cord injury, is one of the diseases to which therapy by regenerative medicine is expected to be applied.

Transplantation therapy of an intractable neurological disorder using neural stem cells from human embryos or ES cells (for example, Japanese Patent Application Laid-open (JP-A) No. 2002-281962) is recognized as a realistic research target, but has a serious problem in terms of morality and safety. Therefore, practical "stem cell source" is still searched for (for example, Keirstead et al., *Human embryonic stem cell-derived oligodendrocyte progenitor cell transplants remyelinate and restore locomotion after spinal cord injury*, Journal of Neuroscience (2005) vol. 25 (19) pp. 4694; Okano et al., Neural stem cells and regeneration of injured spinal cord, Kidney international (2005), Vol. 68, pp. 1927-1931; Okada et al., *Spatiotemporal recapitulation of central nervous system development by murine embryonic stem cell derived neural stem and progenitor cells*, Stem Cells (2008) vol. 26 (12) pp. 3086-3098).

Examples of stem cells in a living organism include stem cells derived from bone marrow or adipose tissue (for example, International Publication 02/086108 pamphlet). These stem cells have shortcomings such as (1) reduction with age in the number of stem cells that can be obtained, (2) difficulty in terms of ensuring the safety of transplanted stem cells due to accumulation of genetic mutations with age, (3) low proliferative capacity of the cells and (4) severe body invasion accompanying the collection of stem cells (for example, Gronthos et al., *Postnatal human dental pulp stem cells (DPSCs) in vitro and in vivo*, Proc Natl Acad Sci USA (2000) vol. 97 (25) pp. 13625-13630; Miura et al., *SHED: stem cells from human exfoliated deciduous teeth*, Proceedings of the National Academy of Sciences (2003) Vol. 100, 5807-5812). Development of a novel stem cell resource for treatment of intractable neurological disorders to solve these problems is important.

Stem cells from human exfoliated deciduous teeth (SHED) and permanent teeth dental pulp stem cells (DPSCs) derived from wisdom tooth, which are medical wastes, were identified as novel stem cell groups having self-renewal capacity and pluripotency similar to those of BMSCs.

These cells are cell groups derived from neural crest, and exhibit similar properties to neural lineage and high reactivity to the induction of neuronal differentiation (for example, Miura et al., *SHED: stem cells from human exfoliated deciduous teeth*, Proceedings of the National Academy of Sciences (2003) Vol. 100, 5807-5812; Arthur et al., *Adult human dental pulp stem cells differentiate toward functionally active neurons under appropriate environmental cues*, Stem Cells (2008) vol. 26 (7) pp. 1787-1795). Since SHED and DPSCs are self-derived tissue stem cells, safety in the case of transplantation is high, and hardly any moral problem is involved.

However, in conventional study on SHED and DPSCs, there is no finding more than fragmentary analysis of neuronal cell lineage, or observation of engraftment of neuronal-differentiation-induced SHED or DPSCs transplanted into rodents (for example, Arthur et al., *Adult human dental pulp stem cells differentiate toward functionally active neurons under appropriate environmental cues*, Stem Cells (2008) vol. 26 (7) pp. 1787-1795; Huang et al., *Putative dental pulp-derived stem/stromal cells promote proliferation and differentiation of endogenous neural cells in the hippocampus of mice*, Stem Cells (2008) vol. 26 (10) pp. 2654-2663).

Further, there are reports that DPSCs have a potential to be employed in cell-based treatment for systemic disorders such as neuronal disorders and cardiac diseases, and that DPSCs ameliorate ischemic disorders (Arthur et al., *Adult human dental pulp stem cells differentiate toward functionally active neurons under appropriate environmental cues*, Stem Cells (2008) vol. 26 (7) pp. 1787-1795; Gandia C, Arminan A, Garcia-Verdugo J M, et al., *Human dental pulp stem cells improve left ventricular function, induce angiogenesis, and reduce infarct size in rats with acute myocardial infarct*, Stem Cells 2008; 26: 638-645; Iohara K, Zheng L, Wake H, et al., *A novel stem cell source for vasculogenesis in schemia: subfraction of side population cells from dental pulp*, Stem Cells 2008; 26:2408-2418).

Recent research has indicated that MSCs can contribute to skin repair. Further, wound healing by external application of various growth factors is widely studied. However, the result of the use of growth factors in single administration or multiple administrations, or the result of the use of multiple growth factors in combination with a view to obtaining synergistic effects, has not been clinically confirmed.

Further, treatment of a group of aged population who has excessively been exposed to sunlight is a large focus of cosmeceutical products and dermatologists. Various non-invasive treatments and topical cosmeceutical products are used in order to treat some of the symptoms of photo-aged skin such as wrinkles (Chung J H, Youn S H, Kwon O S, Cho K H, Youn J I, Eun H C., *Regulations of collagen synthesis by ascorbic acid, transforming growth factor-beta and interferon gamma in human dermal fibroblasts cultured in three-dimensional collagen gel are photoaging-and aging-independent*, J Dermatol Sci 1997; 15: 188-200; Fitzpatrick R E, Rostan E F., *Reversal of photodamage with topical growth factors: a pilot study*, J Cosmet Laser Ther 2003; 5: 25-34).

Exposure to short-wavelength ultraviolet rays (UVB), which is one reason of aging, is known to stimulate collagenase production by human dermal fibroblasts (HDF) in the dermis, and to up-regulate the expression of a collagenase gene. This is considered to induce the degradation of collagen and deposition of a degenerated elastic tissue which appears as skin wrinkles and yellowing.

Previous studies indicate that MSCs produce various cytokines such as vascular endothelial growth factor (VEGF), hepatocyte growth factor (HGF), insulin-like growth factor (IGF), platelet-derived growth factor (PDGF) and transforming growth factor β(TGF-β). In recent years, the production and secretion of cytokines are reported as important functions of MSCs, and a wide variety of pharmaceutical activities of MSCs has been demonstrated in, particularly, skin biology (Jettanacheawchankit S, Sasithanasate S, Sangvanich P, Banlunara W, Thunyakitpisal P., *Acemannan stimulates gingival fibroblast proliferation; expressions of keratinocyte growth factor-1, vascular endothelial growth factor, and type I collagen; and wound healing*, J Pharmacol Sci. 2009 April; 109(4): 525-531; Miura et al., *SHED: stem cells from human exfoliated deciduous teeth*, Proceedings of the National Academy of Sciences (2003) Vol. 100, 5807-5812; Safavi S M, Kazemi B, Esmaeili M, Fallah A, Modarresi A, Mir M., *Effects of low-level He—Ne laser irradiation on the gene expression of IL-1 beta, TNF-alpha, IFN-gamma, TGF-beta, bFGF, and PDGF in rat's gingiva*, Lasers Med Sci. 2008 July; 23(3): 331-335; Saygun I, Karacay S, Serdar M, Ural A U, Sencimen M, Kurtis B, *Effects of laser irradiation on the release of basic fibroblast growth factor (bFGF), insulin like growth factor-1 (IGF-1), and receptor of IGF-1 (IGFBP3) from gingival fibroblasts*, Lasers Med Sci. 2008 April; 23(2): 211-215). For example, it was reported that MSCs have skin healing effects via production of various growth factors (see, Minoru Ueda, *The Use of fibroblasts*, The Biochemical Society, 11-15, 2007). These growth factors activated HDF, enhanced growth/migration of HDF, and mediated collagen secretion from HDF. Since secretion factors from MSCs were indicated to protect HDF from oxidation stress, the antioxidant effect of MSCs was also demonstrated. Application of topical growth factors resulted in stimulation of repair of photoaging of the face, and provided a smoother clinical appearance of the skin with de novo synthesis of collagen, decreased thickening of epithelium and a reduction in visually-noticeable wrinkles (He H, Yu J, Liu Y, et al., *Effects of FGF2 and TGFbeta1 on the differentiation of human dental pulp stem cells in vitro*, Cell Biol Int 2008; 32: 827-834; Robey P G., *Stem cells near the century mark*, J Clin Invest 2000; 105: 1489-1491).

SUMMARY OF INVENTION

Problem to be Solved by Invention

Nonetheless, it is still unclear how dental pulp stem cells such as SHED or DPSCs can be medically applied, and specific target diseases thereof are not known at all.

An object of the present invention is to provide a novel therapeutic means that utilizes dental pulp stem cells.

Means for Solving the Problem

The present invention encompasses the following aspects:

[1] A damaged part treatment composition for repairing a damaged part of a target tissue, the composition including a stem cell-conditioned medium obtained by culturing stem cells.

[2] The damaged part treatment composition according to [1], which does not include the stem cells.

[3] The damaged part treatment composition according to [1] or [2], wherein the stem cell-conditioned medium includes at least two cytokines.

[4] The damaged part treatment composition according to any one of [1] to [3], wherein the stem cell-conditioned medium includes at least two cytokines selected from the group consisting of vascular endothelial growth factor (VEGF), hepatocyte growth factor (HGF), insulin-like growth factor (IGF), platelet-derived growth factor (PDGF) and transforming growth factor β (TGF-β).

[5] The damaged part treatment composition according to any one of [1] to [4], wherein the stem cells are somatic stem cells.

[6] The damaged part treatment composition according to any one of [1] to [5], wherein the stem cells are derived from mesenchymal stem cells.

[7] The damaged part treatment composition according to any one of [1] to [6], wherein the stem cells are dental pulp stem cells.

[8] The damaged part treatment composition according to any one of [1] to [7], which does not include any serum.

[9] The damaged part treatment composition according to any one of [1] to [8], wherein the treatment of a damaged part includes treatment of damage to skin, periodontal tissue or bone, treatment of cerebral infarction or treatment of a central nervous system (CNS) disease.

[10] The damaged part treatment composition according to any one of [1] to [9], wherein the treatment of a damaged part includes treatment of a CNS disease, and the CNS disease is a disease or disorder selected from the group consisting of a spinal cord injury, a neurodegenerative disorder, degeneration or loss of neuronal cells and a retinal disease involving a neuronal cell disorder.

[11] A method of producing the damaged part treatment composition of any one of [1] to [10], the method including the following steps (1) to (3):

(1) a step of selecting adhesive cells from dental pulp cells;

(2) a step of culturing the adhesive cells; and (3) a step of collecting a conditioned medium.

[12] The production method according to [11], further including the following step (4):

(4) a step of subjecting the collected conditioned medium to at least one treatment selected from the group consisting of centrifugation, concentration, solvent substitution, dialysis, freezing, drying, freeze-drying, dilution, desalting and storage.

[13] The production method according to [11] or [12], further including one of the following steps (a) or (b):

(a) a step of checking the collected conditioned medium with respect to the presence or absence of a neurite outgrowth activity in the presence of a nerve regeneration inhibitory substance; or (b) a step of checking the collected conditioned medium with respect to the presence or absence of an apoptosis inhibitory activity toward neuronal cells.

[14] A damaged part treatment method for repairing a damaged part of a target tissue, the method including administering the damaged part treatment composition of any one of [1] to [10] to a patient having the target tissue for the damaged part treatment composition, in an amount effective for repairing the damaged part of the target tissue.

[15] The damaged part treatment method according to [14], wherein the administrating is such that the repairing of the damaged part is achieved based on an ability of endogenous stem cells.

[16] The damaged part treatment method according to [14] or [15], wherein the damaged part treatment composition is administered by an administration method selected from the group consisting of intravenous administration, intraarterial administration, intraportal administration, intradermal administration, subcutaneous administration, intramuscular administration, intraperitoneal administration and intranasal administration.

[17] A method of treating cerebral infarction including administering the damaged part treatment composition of any one of [1] to [10] to a cerebral infarction patient, in an amount therapeutically effective for repairing a damaged part of the brain.

[18] The method of treating cerebral infarction according to [17], wherein the damaged part treatment composition is administered by intranasal administration.

[19] A method of treating a CNS disease including administering the damaged part treatment composition of any one of [1] to [10] as a CNS disease treatment composition to a CNS disease patient, in a therapeutically effective amount.

[20] The treatment method according to [19], wherein a dental pulp stem cell is administered to the CNS disease patient simultaneously with, or after, the administering of the CNS disease treatment composition.

[21] The treatment method according to [20], wherein the dental pulp stem cell is an undifferentiated dental pulp stem cell that has not been subjected to differentiation-inducing treatment after obtainment thereof, or a differentiation-induced dental pulp stem cell that has been induced to differentiate into a neural cell after obtainment thereof.

[22] The treatment method according to any one of [19] to [21], wherein a pluripotent stem cell that has been induced to differentiate into a neural cell is administered to the CNS disease patient after the administering of the CNS disease treatment composition.

[23] A method of determining whether or not a prepared dental pulp stem cell-conditioned medium is effective as an active ingredient of the CNS disease treatment composition to be employed in the CNS disease treatment method according to any one of claims 19 to 22, the method including at least one of the following steps (a) or (b):

(a) a step of checking the conditioned medium with respect to the presence or absence of a neurite outgrowth activity in the presence of a nerve regeneration inhibitory substance; or (b) a step of checking the conditioned medium with respect to the presence or absence of an apoptosis inhibitory activity toward neuronal cells.

Advantageous Effect of Invention

According to the invention, a novel treatment means utilizing a dental pulp stem cell, specifically a damaged part treatment composition and a production method thereof, and a damaged part treatment method using the damaged part treatment composition, can be provided.

BRIEF DESCRIPTION OF DRAWINGS

FIG. 16 is a view explaining the experimental model of Example 4 of the invention.

FIG. 17 is a photograph explaining the treatment modalities employed in Example 4 of the invention.

FIG. 18 is a photograph explaining the treatment modalities employed in Example 4 of the invention.

FIG. 19 is a diagram explaining the treatment modalities employed in Example 4 of the invention.

FIG. 37 shows the results of an experiment using an animal model of spinal cord crush injury. Comparison between the control group and the SHED-CM group is shown in terms of the bone marrow state (upper photograph) and the spinal cord weight (lower graph).

BEST EMBODIMENT FOR CARRYING OUT THE INVENTION

<Damaged Part Treatment Composition>

Figure 1:
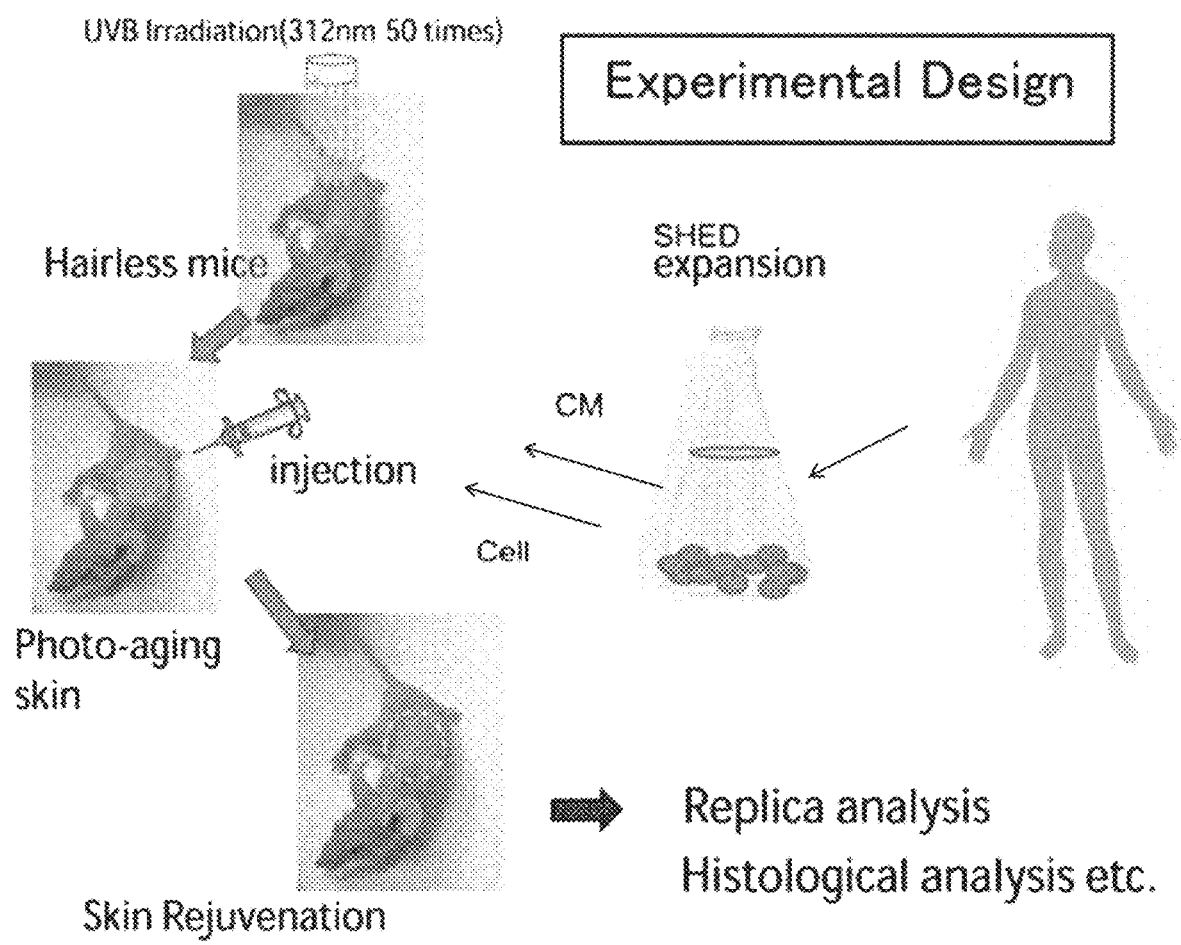
FIG. 1 is a diagram illustrating an experimental design using hairless mice. Wrinkle was induced by UVB irradiation.

The damaged part treatment composition of the invention is a damaged part treatment composition for repairing a damaged part of a target tissue, the composition including a stem cell-conditioned medium obtained by culturing stem cells.

The damaged part treatment method of the invention is a damaged part treatment method for repairing or restoring a damaged part of a target tissue, the method including administering the damaged part treatment composition to a patient having the target tissue for the damaged part treatment composition, in an amount effective for repairing the damaged part of the target tissue.

When the application of SHED to wound healing was still an inference, the inventors of the invention studied the relationship between a growth factor derived from stem cells from human exfoliated deciduous teeth (SHED) and human dermal fibroblasts (HDFs) for the first time. SHED affect HDFs by enhancing collagen synthesis and activating the growth and migration activity of HDFs. This suggests that SHED or SHED-derived conditioned medium (SH-CM) can be used for treatment of photo-aging. The results suggest that SHED and SH-CM should be structurally suitable for treatment of photo-aging. SHED contribute to enhancement of the wound healing activity of HDFs, mainly with a secreted growth factor or extracellular matrix protein. Further study of the mechanism using neutralizing antibodies against respective growth factors clarifies the roles of soluble factors from SHED in the process of wound healing. Further, deciduous teeth naturally exfoliate during infancy, and are usually disposed of as they are. Therefore, utilization of stem cells from human exfoliated deciduous teeth has a great advantage in terms of the absence of invasiveness of the obtainment thereof and morality problem for utilization.

According to the invention, a stem cell-conditioned medium obtained by culturing stem cells is used as an active ingredient for a damaged part treatment composition. When the stem cell-conditioned medium, which contains a cytokine mixture, is applied to a damaged part, the stem cell-conditioned medium induces cell growth in the damaged part, as a result of which the tissue having the damaged part can be repaired. In an embodiment of the invention, it can be presumed that the mixture of cytokines in the stem cell-conditioned medium used in the invention serves as an inductive signal for endogenous stem cells in the target tissue, and, therefore, the endogenous stem cells can differentiate and proliferate. As a result, the proliferation of cells, generation of extracellular matrix, etc. may occur in the damaged part of the target tissue. From these, it is thought that a tissue having a damaged part can be repaired based on such regenerative ability of endogenous stem cells in the target tissue.

For example, secretion of several growth factors involved in skin regeneration from MSCs allows SHED and SHED-derived growth factor to reverse UVB-induced photo-damage. Therefore, wrinkles were induced in hairless mice by an eight-week regimen of UVB irradiation, and an anti-wrinkle effect by the subcutaneous injection of SHED and its conditioned medium was investigated. In addition, mechanisms for improving wrinkling via paracrine routes by further using SH-CM in cultured HDFs were investigated.

In the invention, the term "damaged part" means a part in a tissue that became unable to perform its original function due to occurrence of physical or physiological defect in the tissue, and the concept thereof encompasses external injury as well as a injured part, dysfunctional part or diseased part caused by physical or physiological defect of the tissue.

In the invention, "repair" means that some or all of the functions that was lost due to damage to the target tissue are maintained or recovered as compared to the functions of the damaged part at the time of damaging, and broadly encompasses recovery of the functions of the tissue as well as regeneration as a functional tissue. The assessment for the maintenance or recovery of the functions may be carried out based on, for example, an assay usually employed for the assessment of the appearance and the degree of the function of interest, although the assessment varies depending on the damaged tissue.

Examples of somatic stem cells used in the invention include, but are not limited to, stem cells from the dermal system, the digestive system, the bone marrow system, the nervous system, etc. Examples of the somatic stem cells in the dermal system include epidermal stem cells, hair follicle stem cells, etc. Examples of the somatic cells in the digestive system include pancreatic (common) stem cells, hepatic stem cells, etc. Examples of the somatic cells in the bone marrow system include hematopoietic stem cells, mesenchymal stem cells, etc. Examples of somatic stem cells in the nervous system include neural stem cells, retinal stem cells, etc. Somatic cells used in the invention may be naturally-occurring or genetically-modified as long as they can achieve the intended treatment.

The origins of stem cells are classified into ectoderm, endoderm and mesoderm. Stem cells of ectodermal origin are present mainly in the brain, and include neural stem cells. Stem cells of endodermal origin are present mainly in the bone marrow, and include blood vessel stem cells, hematopoietic stem cells, mesenchymal stem cells, etc. Stem cells of mesoderm origin are present mainly in organs, and include hepatic stem cells, pancreatic stem cells, etc.

In the invention, it is preferable to use somatic stem cells which may be derived from any mesenchyme, more preferably somatic stem cells derived from dental pulp, and most preferably somatic stem cells derived from human exfoliated deciduous teeth. Somatic stem cells from mesenchyme may produce various cytokines such as vascular endothelial growth factor (VEGF), hepatocyte growth factor (HGF), insulin-like growth factor (IGF), platelet-derived growth factor (PDGF), transforming growth factor-$\beta$ (TGF-$\beta$)-1 and -3, TGF-$\alpha$, KGF, HBEGF and SPARC. In the invention, the stem cell-conditioned medium preferably includes at least two cytokines, and more preferably includes a combination of two or more selected from the group consisting of vascular endothelial growth factor (VEGF), hepatocyte growth factor (HGF), insulin-like growth factor (IGF), platelet-derived growth factor (PDGF) and transforming growth factor (TGF-$\beta$).

The mixture of cytokines for use in the invention may be used as a part of the stem cell-conditioned medium or as a mixture of cytokines that has been isolated from the stem cell-conditioned medium. In the mixture of cytokines isolated from the stem cell-conditioned medium, a part of the cytokines may be replaced with one or more known corresponding cytokine.

The stem cell-conditioned medium for use in the invention is preferably obtained from a culture of somatic stem cells derived from the same individual as that having the target tissue, in order to avoid rejection. The target tissue may be the same as or different from a tissue from which the somatic stem cell used to obtain the stem cell-conditioned medium is derived.

A stem cell-conditioned medium used in the invention is not limited to a stem cell-conditioned medium obtained from culturing somatic stem cells, and may contain a stem cell-conditioned medium obtained from culturing embryonic stem cells (ES cells), induced pluripotent stem cells (iPS cells), embryonal carcinoma cells (EC cells) or the like.

The somatic stem cell-conditioned medium is a medium obtained by culturing somatic stem cells, and does not include the cells themselves. The conditioned medium that can be used in the invention can be obtained by, for example, removing cell components by separation after culturing. The conditioned medium may be subjected to various treatments (such as centrifugation, concentration, solvent substitution, dialysis, freezing, drying, freeze-drying, dilution, desalting or storage), as appropriate, before use.

The stem cells for obtaining the stem cell-conditioned medium can be selected by an ordinary method, and can be selected based on the size and morphology of cells, or as adhesive cells. In the case of dental pulp stem cells, the stem cells can be selected as adhesive cells from dental pulp cells obtained from exfoliated deciduous teeth or permanent teeth, or as subcultured cells thereof, as described below. The later-described method of producing a CNS disease treatment composition can preferably be used as a method of producing the damaged part treatment composition. The dental pulp stem cell-conditioned medium to be used may be a conditioned medium obtained by culturing the selected stem cells. In the case of using other stem cells, the stem cell-conditioned medium can be obtained after obtaining target stem cells from a tissue that may contain the target stem cells in a similar manner.

The "stem cell-conditioned medium" is defined as a medium that is obtained by culturing stem cells, and that does not include cells themselves. The composition of the invention includes the "stem cell-conditioned medium" as an active ingredient. In an aspect of the composition, the composition as a whole does not include any cells (regardless of the type of cells). The composition according to this aspect is clearly distinguished from the stem cells themselves as a matter of course, and from various compositions that contain stem cells, due to the feature described above. A typical example of this aspect is a composition that does not include any stem cells, and that consists only of the stem cell-conditioned medium.

A basal medium, or a medium obtained by adding serum or the like to a basal medium, can be used for the stem cell culture medium. In the case of preparing a serum-free "dental pulp stem cell-conditioned medium", it is preferable to use a serum-free medium throughout the entire process or to use a serum-free medium at subculturing for the last passage, or for the last few passages. DMEM, Iscove's Modified Dulbecco's Medium (IMDM) (GIBCO Corporation, etc.), Ham's F12 medium (HamF12) (Sigma-Aldrich Corporation, GIBCO Corporation, etc.), RPMI1640 medium, etc., can be used as the basal medium. Two or more basal media may be used in combination. An example of a mixed medium is a medium formed by mixing equivalent amounts of IMDM and HamF12 (commercially available as, for example, IMDM/HamF12 (tradename, GIBCO Corporation)). Examples of ingredients that can be added to the medium include serums (such as fetal bovine serum, human serum and sheep serum), serum replacements (knockout serum replacement (KSR), etc.), bovine serum albumin (BSA), antibiotics, various vitamins and various minerals.

For the cultivation of stem cells, usually-employed conditions can be applied as they are. The method for producing a stem cell-conditioned medium may be the same as the later-described method of producing a CNS disease treatment composition, except for appropriately modifying the step of isolation and selection of stem cells in accordance with the type of stem cells. Those skilled in the art would be able to appropriately carry out the isolation and selection of stem cells in accordance with the type of stem cells.

Figure 9:
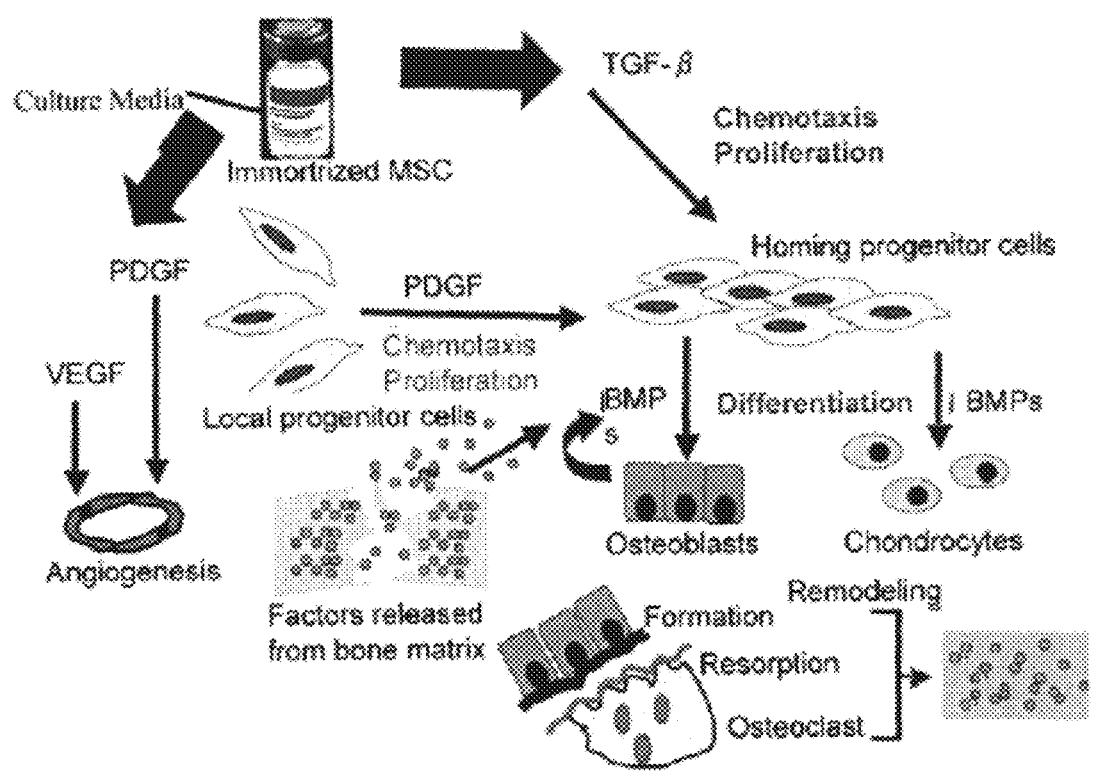
FIG. 9 is a conceptual diagram illustrating the mechanism of bone regeneration using the composition of the invention.

The target tissue in the invention is not particularly limited, and examples thereof include skin, bone, periodontal tissue, brain, etc. The composition of the invention is effective for repairing such target tissues. As an example, FIG. 9 shows a conceptual diagram of the mechanism of bone regeneration using the composition of the invention.

The composition of the invention is also effective for the treatment of disorders related to tissue damage. Examples of such disorders include cerebral infarction, periodontal disease, spinal cord injury, skin ulceration, osteoporosis, etc. In other words, the composition of the invention is a composition for treatment of cerebral infarction, periodontal disease, spinal cord injury, skin ulceration, osteoporosis, etc., and includes a stem cell-conditioned medium obtained by culturing somatic stem cells. For example, the damaged part treatment composition of the invention is used as a composition for treatment of a damaged part, such as treatment of a damage to skin, periodontal tissue or bone, treatment of cerebral infarction or treatment of CNS disease. The dosage of the damaged part treatment composition may be any therapeutically effective amount. When the damaged part treatment composition, which includes the stem cell-conditioned medium as an active ingredient, is used for treatment, the dosage of the damaged part treatment composition may be adjusted, as appropriate. The damaged part treatment composition may be used after concentrating the active ingredient as described below.

Other ingredients may additionally be used in the composition of the invention in accordance with the state of the subject to which the composition is applied, as long as the expected therapeutic effect is maintained. Some examples of ingredients that can additionally be used in the invention include the following:

(i) Bioabsorbable Materials

Hyaluronic acid, collagen, fibrinogen (for example, BOL-HEAL (registered trademark)), etc., may be used as organic bioabsorbable materials.

(ii) Gelling Materials

Gelling materials for use preferably have high bioaffinity, and hyaluronic acid, collagen, fibrin adhesive or the like may be used. Various hyaluronic acids and collagens may be selected and used, and it is preferable to adopt those suitable for the purpose of application of the composition of the invention (the tissue to which the composition is to be applied). Collagens to be used are preferably soluble (acid-soluble collagens, alkali-soluble collagens, enzyme-solubilized collagens, etc.).

(iii) Others

Other pharmaceutically-acceptable ingredients (for example, carriers, excipients, disintegrants, buffer agents, emulsifying agents, suspending agents, soothing agents, stabilizers, preservatives, antiseptic agents, physiological saline, etc.) may be contained. Lactose, starch, sorbitol, D-mannitol, white sugar, etc. may be used as excipients. Starch, carboxymethylcellulose, calcium carbonate, etc. may be used as disintegrants. Phosphoric acid salts, citric acid salts, acetic acid salts, etc. may be used as buffering agents. Gum arabic, sodium alginate, Tragacanth, etc. may be used as emulsifying agents. Glycerin monostearate, aluminum monostearate, methylcellulose, carboxymethylcellulose, hydroxymethylcellulose, sodium lauryl sulfate, etc. may be used as suspending agents. Benzyl alcohol, chlorobutanol, sorbitol, etc. may be used as soothing agents. Propyleneglycol, ascorbic acid, etc. may be used as stabilizers. Phenol, benzalkonium chloride, benzylalcohol, chlorobutanol, methylparaben, etc. may be used as preservatives. Benzalkonium chloride, parahydroxybenzoic acid, chlorobutanol, etc. may be used as antiseptic agents. Antibiotics, pH adjusting agents, growth factors (such as epidermal growth factor (EGF), nerve growth factor (NGF) and brain-derived neurotrophic factor (BDNF)), etc. may also be contained.

The final form of the composition of the invention is not particularly limited. Examples of the form include liquid forms (such as a purely liquid form and a gel form), and solid forms (such as a powdery form, a fine grain form and a granular form).

Other aspects of the invention include a method of repairing a damaged part of a target tissue and a method of treating a damaged tissue. These methods include administering the stem cell-conditioned medium to the damaged part of the target tissue or the damaged tissue. Due to the administering, the target tissue having the damaged part can effectively be repaired. In particular, in a case in which the target tissue is brain, the methods can preferably applied as a method of treating cerebral infarction.

The method and route of the administration of the damaged part treatment composition are not particularly limited. For example, the damaged part treatment composition is preferably administered parenterally, and the parenteral administration may be systemic administration or topical administration. Examples of topical administration include injection, application or spraying to the target tissue, etc. Examples of the method of administering the damaged part treatment composition include intravenous administration, intraarterial administration, intraportal administration, intradermal administration, subcutaneous administration, intramuscular administration, intraperitoneal administration, intranasal administration, etc. In particular, intranasal administration or the like is preferable due to its low invasiveness. The dosage regimen may be, for example, from once to several times a day, once every two days, once every three days, or the like. The dosage regimen may be prepared in consideration of the sex, age, weight, pathological condition, etc. of the subject (recipient).

The selection of the administration method may be carried out by a person skilled in the art, based on the type of target tissue, the type of disease to be treated, etc. For example, application of intranasal administration or the like is particularly preferable for, for example, the treatment of a disorder or repair of a damaged tissue of which target tissue is located in the brain, because the intranasal administration is less invasive and free from the need to consider the passage through the blood-brain barrier. For example, intranasal administration may preferably be applied in a case in which the target tissue is brain. Intranasal administration may preferably be applied to treatment of cerebral infarction.

The subject to which the damaged part treatment composition is administered is typically a human patient having damage in the target tissue. However, application to mammals other than human (including pet animals, farm animals and laboratory animals, specific examples of which include mice, rats, guinea pigs, hamsters, monkeys, cattle, pigs, goats, sheep, dogs, cats, etc.) is also contemplated.

The method of treating cerebral infarction of the invention includes intranasally administering the stem cell-conditioned medium, to repair a damaged part of the brain. According to this treatment method, a region that was damaged by cerebral infarction can effectively be restored with less invasiveness.

<CNS Disease Treatment Composition>

Other aspects of the invention encompass, particularly, a CNS disease treatment composition and a method of treating a CNS disease.

The inventors carried out research under the circumstance discussed above. The inventors have clarified that dental pulp stem cells are a unique group of cells that coexpress all neural lineage markers including neural stem cell markers, differentiated neural cell markers, astrocyte markers and oligodendrocyte markers, and that dental pulp stem cells highly express brain-derived neurotrophic factor (BDNF), and have also demonstrated, through animal experiments, that dental pulp stem cells induce nerve regeneration (see Japanese Patent Application No. 2010-92585).

As described above, the inventors thus far looked for the potential capacity of dental pulp stem cells (SHED, DPSCs), and studied the utility thereof as cells from various viewpoints. During the course of further advancing the research, the inventors have drastically changed their viewpoint, and carried out various experiments focusing on a dental pulp stem cell-conditioned medium. Here, there is an already known fact that peripheral nerves easily regenerate after being damaged, but central nerves (brain, spinal cord) rarely regenerate. The biggest reason why the central nerve regeneration does not occur is the presence of various factors that inhibit outgrowth of regenerated axons in the CNS after being damaged. Activated astrocyte-derived chondroitin sulfate proteoglycan (CSPG), myelin-associated glycoprotein (MAG), etc. have thus far been identified as nerve regeneration inhibitory factors. These inhibitory substances inhibit neuronal axon outgrowth via activation of intracellular protein Rho or ROCK, and induce apoptosis. No agent has been found which inhibits apoptosis even in the presence of nerve regeneration inhibitory factor, and which exerts axon elongation effect. Analysis by the inventors revealed a surprising fact that a dental pulp stem cell-conditioned medium inhibits the action of nerve regeneration inhibitory substances (cancels the inhibition), promotes outgrowth of neurites, and suppresses apoptosis even in the environment of a damaged CNS (i.e., the environment in which substances that inhibit outgrowth of neurites and induce apoptosis are present). The inventors further studied the activity of the dental pulp stem cell-conditioned medium using model animals with injured spinal cord, as a result of which the administration of the dental pulp stem cell-conditioned medium remarkably improved the motor function of hindlimbs. Further, as a result of histological evaluation, the administration of the dental pulp stem cell-conditioned medium suppressed morphological alteration of the spinal cord and enlargement of nerve injury. As discussed above, excellent regenerative and therapeutic effects of the dental pulp stem cell-conditioned medium were confirmed also by animal experiments.

As described above, earnest study by the inventors of the invention resulted in a finding that the dental pulp stem cell-conditioned medium is quite effective for regeneration and healing of the CNS. The invention as discussed below is mainly based on this finding. Here, the dental pulp stem cell-conditioned medium is more advantageous than a case in which dental pulp stem cells themselves are used, in terms of advance preparation and storage, and the dental pulp stem cell-conditioned medium is particularly suitable for the treatment of the acute or subacute phase of CNS diseases. The utility of the dental pulp stem cell-conditioned medium is quite high also in the sense that the dental pulp stem cell-conditioned medium does not include any cellular components and is capable of overcoming the immune rejection problem.

The present aspect of the invention includes the following:

[1] A CNS disease treatment composition including a dental pulp stem cell-conditioned medium.

[2] The CNS disease treatment composition according to [1], which exhibits a neurite outgrowth activity in the presence of a nerve regeneration inhibitory substance.

[3] The CNS disease treatment composition according to [2], wherein the nerve regeneration inhibitory substance is chondroitin sulfate proteoglycan or myelin-associated glycoprotein.

[4] The CNS disease treatment composition according to any one of [1] to [3], which exhibits an apoptosis inhibitory activity toward neuronal cells.

[5] The CNS disease treatment composition according to any one of [1] to [4], which does not include any dental pulp stem cells.

[6] The CNS disease treatment composition according to any one of [1] to [4], which is combined with dental pulp stem cells.

[7] The CNS disease treatment composition according to [6], wherein the dental pulp stem cells are undifferentiated dental pulp stem cells that have not been subjected to differentiation-inducing treatment after obtainment thereof.

[8] The CNS disease treatment composition according to any one of [1] to [7], which does not include serum.

[9] The CNS disease treatment composition according to any one of [1] to [9], wherein the conditioned medium is a conditioned medium obtained by culturing adhesive cells in dental pulp cells or subcultured cells thereof.

[10] The CNS disease treatment composition according to any one of [1] to [9], wherein the CNS disease is a disease or disorder selected from the group consisting of neurodegenerative diseases such as spinal cord injury, amyotrophic lateral sclerosis, Alzheimer's disease, Parkinson's disease, progressive supranuclear palsy, Huntington's disease, multiple system atrophy and spinocerebellar ataxia, degeneration or loss of neuronal cells caused by cerebral ischemia, intracerebral hemorrhage or cerebral infarction and a retinal disease involving a neuronal cell disorder.

[11] A method of producing a CNS disease treatment composition including the following steps (1) to (3):

(1) a step of selecting adhesive cells from dental pulp cells;

(2) a step of culturing the adhesive cells; and (3) a step of collecting a conditioned medium.

[12] The production method according to [11], wherein the step (2) is carried out using a serum-free medium.

[13] The production method according to [11] or [12], wherein the conditioned medium after subculturing is collected in step (3).

[14] The production method according to any one of [11] to [13], further including the following step (4):

(4) a step of subjecting the collected conditioned medium to at least one treatment selected from the group consisting of centrifugation, concentration, solvent substitution, dialysis, freezing, drying, freeze-drying, dilution, desalting and storage.

[15] The production method according to any one of [11] to [14], further including the following step (a) and/or (b):

(a) a step of checking the collected conditioned medium with respect to the presence or absence of a neurite outgrowth activity in the presence of a nerve regeneration inhibitory substance; and (b) a step of checking the collected conditioned medium with respect to the presence or absence of an apoptosis inhibitory activity toward neuronal cells.

[16] The production method according to any one of [11] to [15], wherein the CNS disease is a disease or disorder selected from the group consisting of spinal cord injury, neurodegenerative diseases such as amyotrophic lateral sclerosis, Alzheimer's disease, Parkinson's disease, progressive supranuclear palsy, Huntington's disease, multiple system atrophy and spinocerebellar ataxia, degeneration or loss of neuronal cells caused by cerebral ischemia, intracerebral hemorrhage or cerebral infarction and a retinal disease involving a neuronal cell disorder.

[17] A method of treating a CNS disease including a step of administering the CNS disease treatment composition of any one of [1] to [10] to a CNS disease patient, in a therapeutically effective amount.

[18] The treatment method according to [17], wherein a dental pulp stem cell is administered to the CNS disease patient simultaneously with, or after, the administering of the CNS disease treatment composition.

[19] The treatment method according to [18], wherein the dental pulp stem cell is an undifferentiated dental pulp stem cell that has not been subjected to differentiation-inducing treatment after obtainment thereof, or a differentiation-induced dental pulp stem cell that has been induced to differentiate into a neural cell after obtainment thereof.

[20] The treatment method according to [17], wherein a pluripotent stem cell that has been induced to differentiate into a neural cell is administered to the CNS disease patient after the administering of the CNS disease treatment composition.

[21] A method of determining whether or not a prepared dental pulp stem cell-conditioned medium is effective as an active ingredient of the CNS disease treatment composition, the method comprising the following step (a) and/or (b):

(a) a step of checking the conditioned medium with respect to the presence or absence of a neurite outgrowth activity in the presence of a nerve regeneration inhibitory substance; and (b) a step of checking the conditioned medium with respect to the presence or absence of an apoptosis inhibitory activity toward neuronal cells.

The CNS disease treatment composition of the invention includes a dental pulp stem cell-conditioned medium. Dental pulp stem cells are roughly classified into two types—dental pulp stem cells from deciduous teeth and permanent teeth dental pulp stem cells. In the present specification, dental pulp stem cells from deciduous teeth are abbreviated to SHED, and permanent teeth dental pulp stem cells are abbreviated to DPSCs, in accordance with customary practices. Each of a SHED-conditioned medium and a DPSC-conditioned medium can be used as a conditioned medium for forming the CNS disease treatment composition.

The CNS disease treatment composition can be characterized by the feature—"exhibiting a neurite outgrowth activity in the presence of nerve regeneration inhibitory substance".

Dissimilar to the peripheral nervous system, nerve regeneration inhibitory substances (neurite outgrowth inhibitory factors) are present in the CNS. This is an important point when CNS disease therapy (mainly nerve regeneration) is planned, and needs consideration. Using the CNS disease treatment composition having the feature described above allows for suppression of the action of nerve regeneration inhibitory substances, and promotion of nerve regeneration. Examples of the nerve regeneration inhibitory substances are chondroitin sulfate proteoglycan (CSPG) and myelin-associated glycoprotein (MAG). Whether or not the CNS disease treatment composition has the feature can be confirmed by, for example, an in vitro experimentation using neuronal cells and a nerve regeneration inhibitory substance (CSPG or MAG) (see later-described Examples with respect to the details of the experimentation). A test composition is confirmed to have the above-described feature if neurite outgrowth is observed when the neuronal cells are cultured in the coexistence of the test composition and CSPG or MAG.

The CNS disease treatment composition can alternatively be characterized by the feature—"exhibiting an apoptosis inhibiting activity toward neuronal cells". Whether or not the CNS disease treatment composition has this feature can be confirmed by, for example, an in vitro experimentation using neuronal cells (see later-described Examples with respect to the details of the experimentation). A test composition is confirmed to have this feature if cell death due to apoptosis is suppressed when the neuronal cells are cultured in the presence of the test composition. In a preferable aspect, the CNS disease treatment composition has both of this feature and the above-described feature (exhibiting a neurite outgrowth activity in the presence of a nerve regeneration inhibitory substance).

In the present aspect, the term "dental pulp stem cell-conditioned medium" refers to a medium that is obtained by culturing dental pulp stem cells, and that does not include cell components (i.e., dental pulp cells and dental pulp stem cells). Therefore, a conditioned medium that can be used in the invention can be obtained by, for example, removing cell components by separation after culturing. The conditioned medium may be subjected to various treatments (such as centrifugation, concentration, solvent substitution, dialysis, freezing, drying, freeze-drying, dilution, desalting or storage), as appropriate, before use. Details of treatment methods for the conditioned medium are described later.

Dental pulp stem cells can be selected as adhesive cells in dental pulp cells. Therefore, a conditioned medium obtained by culturing adhesive cells in dental pulp cells collected from exfoliated deciduous teeth or permanent teeth, or subcultured cells thereof, can be used as the dental pulp stem cell-conditioned medium. Details of the method of preparing the dental pulp stem cell-conditioned medium are described later.

As described above, the dental pulp stem cell-conditioned medium is defined as a medium that is obtained by culturing dental pulp stem cells and that does not include cell components. The CNS disease treatment composition includes the dental pulp stem cell-conditioned medium as an active ingredient, and, in one aspect thereof, the composition as a whole does not include any cells (regardless of the type of cells). The composition according to this aspect is clearly distinguished from the dental pulp stem cells themselves as a matter of course, and from various compositions that contain dental pulp stem cells, based on the feature described above. A typical example of this aspect is a composition consisting only of the dental pulp stem cell-conditioned medium.

One embodiment of the present aspect has characteristics in that the dental pulp stem cell-conditioned medium and the dental pulp stem cells are used in combination. Preferably, dental pulp stem cells from deciduous teeth (SHED) are used in consideration of their higher cell proliferation capacity compared to permanent teeth dental pulp stem cells (DPSCs). Further, SHED are considered to have higher differentiation capacity. A high BDNF expression level of SHED (see, Japanese Patent Application No. 2010-92585), which may provide higher therapeutic effects, is another advantage of using SHED. In addition, SHED also has an advantage in that SHED can be easily obtained.

In recent years, researches aiming to realize regenerative medicine using cells have been carried out by many research groups. In the case of using cells, cells obtained from a living body are subjected to cultivation, selection, treatment or the like, and are thereafter recovered and used as transplant components. In this series of operations, a conditioned medium is usually disposed of or replaced by, for example, physiological saline. Therefore, the final transplant does not actively contain the conditioned medium. In view of this, even the composition of the above-described embodiment in which the dental pulp stem cell-conditioned medium and the dental pulp stem cells are used in combination is literally and practically distinguished from compositions or agents in which the dental pulp stem cells are used as active ingredients with a focus on the utility of dental pulp stem cells themselves, based on the point that the composition of the above-described embodiment includes the dental pulp stem cell-conditioned medium as an essential active ingredient.

The embodiment described above is characterized by combined use of the dental pulp stem cell-conditioned medium and the dental pulp stem cells. The expression "combined use" as used herein means that the dental pulp stem cell-conditioned medium and the dental pulp stem cells are used together. Typically, the CNS disease treatment composition is provided as a combination preparation in which the dental pulp stem cell-conditioned medium and the dental pulp stem cells are mixed. In such a case, it is preferable to use dental pulp stem cells that have not been subjected to induction of differentiation after obtainment thereof (i.e., dental pulp stem cells that remain undifferentiated; also referred to as "undifferentiated dental pulp stem cells" herein). In this case, the CNS disease treatment composition exerts strong nerve protection activity, and is thus suitable to, particularly, application in the acute or subacute phase of CNS diseases (for example, intractable neural diseases involving severe loss or degeneration of neuronal cells, such as spinal cord injury or cerebral infarction). The dental pulp stem cells used in this embodiment are positive for the neural stem cell marker Nestin, positive for the neural stem cell marker Doublecortin, positive for the neuronal call marker β-III tubulin, positive for the neuronal call marker NeuN, positive for the astrocyte marker GFAP, and positive for the oligodendrocyte marker CNPase, and highly express BDNF (see, Japanese Patent Application No. 2010-92585).

The CNS disease treatment composition may also be provided in the form of, for example, a kit composed of a first constituent element containing the dental pulp stem cell-conditioned medium and a second constituent element containing the dental pulp stem cells.

In this case, to a subject to be treated (usually, a CNS disease patient) administered with the first constituent element, the second constituent element is administered simultaneously with the administration of the first constituent element or after the administration of the first constituent element. A regimen in which the first constituent element and the second constituent element are simultaneously administered is particularly suitable for application in the acute or subacute phase of CNS diseases. In order that high therapeutic effects are exerted in the case of application in the acute or subacute phase, it is preferable to use undifferentiated dental pulp stem cells as an active ingredient of the second constituent element.

Here, the term "simultaneously" does not require exact simultaneity. Accordingly, the concept of "simultaneously" encompasses a case in which both elements are administered with no time lag such as administration to the subject after mixing of both constituent elements, as well as a case in which both constituent elements are administered with substantially no time lag such as administration of one of the constituent elements immediately after the administration of the other one of the constituent elements.

According to a regimen in which the first constituent element is administered in the acute or subacute phase, and the second constituent element is administered thereafter (for example, 3 days to 1 week after the administration of the first constituent element), continuous and comprehensive therapeutic effects can be expected. In a case in which this regimen is planned, it is preferable to use dental pulp stem cells that have been induced to differentiate into neural cells (here also referred to as "differentiation-induced dental pulp stem cells") as an active ingredient of the second constituent element. Here, the scope of the term "neural cells" encompasses motor neurons, dopamine-producing cells, various CNS cells, astrocytes, oligodendrocytes and Schwann cells. The type of neural cells into which the dental pulp stem cells are to be induced to differentiate may be determined in consideration of the disease and pathological condition of the subject to be treated. For example, for the treatment of spinal cord injury, dental pulp stem cells that have been induced to differentiate into mature nerve cells, oligodendrocytes or Schwann cells may be used in the second constituent element. An example of a method of inducing neural differentiation is described below.

A method composed of the following two steps may be used for induction of differentiation into dopamine-producing neuronal cells. In the first step, dental pulp stem cells are cultured for 2 to 3 days in, for example, a DMED medium that contains 12.5 U/mL Nystatin, N2 supplement, 20 ng/mL bFGF and 20 ng/mL EGF, using a dish coated with poly-L-lysine. As a result of this step, neural stem cell differentiation of the dental pulp stem cell is induced. In the second step, the cells after the first step are cultured for 6 to 7 days in, for example, a NeurobasaP medium that contains B27 supplement, 1 mM db-cAMP, 0.5 mM IBMX, 200 μM ascorbic acid and 50 ng/mL BDNF. The induced dopamine-producing neuronal cells can be confirmed by immunostaining using an anti-tyrosine hydroxylase antibody. Besides the above method, various methods that have been reported as methods for inducing differentiation of neural stem cells or embryonic stem cells into dopamine-producing neuronal cells, such as a method of culturing in the presence of bFGF followed by floating culture of aggregates (Studer, L. et al.: Nat. Neurosci., 1: 290-295, 1998), a method of culturing in the presence of bFGF and glia cell-conditioned medium (Daadi, M. M. and Weiss, S. J.: Neuroscience, 19: 4484-4497, 1999), a method utilizing FGF8, Shh, bFGF, ascorbic acid, etc. (Lee, S. H. et al.: Nat. Biotechnol., 18: 675-679, 2000), and a method of co-culturing with bone marrow stromal cells (Kawasaki, H. et al.: Neuron, 28: 31-40, 2000), may be utilized after appropriate modification thereof, if necessary.

A method composed of the following two steps may be used for induction of astrocyte differentiation. In the first step, dental pulp stem cells are cultured for four days in, for example, a DMEM/F12 medium that contains N2 supplement and 10 ng/mL bFGF, using a dish doubly coated with poly-L-ornithine and fibronectin. In the second step, the cells are cultured for three days in the medium further added with 80 ng/mL LIF and 80 ng/mL BMP2. The differentiation induced astrocytes can be confirmed by immunostaining using an anti-GFAP antibody.

A method composed of the following two steps may be used for induction of oligodendrocyte differentiation. Similar to the induction of astrocyte differentiation, in the first step, dental pulp stem cells are cultured for four days in, for example, a DMEM/F12 medium that contains N2 supplement, 10 ng/mL bFGF and 0.5% FCS, using a dish doubly coated with poly-L-ornithine and fibronectin. As a result of this step, the dental pulp stem cells are induced into oligodendrocyte progenitor cells. In the subsequent second step, the cells are cultured for four days in a DMEM/F12 medium that contains 20 ng/mL T3 (Triiodothyronine), 20 ng/mL T4 (Thyroxine) and N2 supplement. The differentiation induced oligodendrocytes can be confirmed using an anti-04 antibody.

As a component of the second constituent element, pluripotent stem cells that have been induced to differentiate into neural cells may be used in addition to, or in place of, the differentiation induced dental pulp stem cells. Examples of pluripotent stem cells include induced pluripotent stem cells (iPS cells) and embryonic stem cells (ES cells). The "induced pluripotent stem cells (iPS cells)" are cells having pluripotency (multipotency) and proliferative capacity that are produced by reprogramming somatic cells by introduction of reprogramming factors. The induced pluripotent stem cells exhibit properties similar to those of ES cells. The iPS cells can be produced by various iPS cell production methods that have been reported thus far. Of course, application of iPS cell production methods that will be developed in the future is also contemplated, as a matter of course.

The most basic technique among iPS cell production methods is a method of introducing the four transcriptional factors of Oct3/4, Sox2, KIF4 and c-Myc into a cell using a virus (Takahashi K, Yamanaka S: Cell 126 (4), 663-676, 2006; Takahashi, K, et al: Cell 131 (5), 861-72, 2007). Establishment of human iPS cells by introducing the four factors of Oct4, Sox2, Lin28 and Nonog is also reported (Yu J, et al: Science 318 (5858), 1917-1920, 2007). Establishment of iPS cells by introducing the three factors other than c-Myc (Nakagawa M, et al: Nat. Biotechnol. 26 (1), 101-106, 2008), the two factors of Oct3/4 and Klf4 (Kim J B, et al: Nature 454 (7204), 646-650, 2008) or only Oct3/4 (Kim J B, et al: Cell 136 (3), 411-419, 2009) has also been reported. Further, a technique of introducing proteins as expression products of the genes into a cell (Zhou H, Wu S, Joo J Y, et al: Cell Stem Cell 4, 381-384, 2009; Kim D, Kim C H, Moon J I, et al: Cell Stem Cell 4, 472-476, 2009) has also been reported. There is also a report that the use of, for example, an inhibitor (BIX-01294) against histone methyltransferase G9a, histone deacetylase inhibitor valproic acid (VPA) or BayK8644 allows for improvement in the production efficiency, reduction of factors to be introduced, etc (Huangfu D, et al: Nat. Biotechnol. 26 (7), 795-797, 2008; Huangfu D, et al: Nat. Biotechnol. 26 (11), 1269-1275, 2008; Silva J, et al: PLoS. Biol. 6 (10), e 253, 2008). Studies on gene introduction methods have also been carried out, and techniques using retroviruses, as well as lentiviruses (Yu J, et al: Science 318(5858), 1917-1920, 2007), adenovirus (Stadtfeld M, et al: Science 322 (5903), 945-949, 2008), plasmids (Okita K, et al: Science 322 (5903), 949-953, 2008), transposon vectors (Woltjen K, Michael I P, Mohseni P, et al: Nature 458, 766-770, 2009; Kaji K, Norrby K, Pac a A, et al: Nature 458, 771-775, 2009; Yusa K, Rad R, Takeda J, et al: Nat Methods 6, 363-369, 2009), or episomal vectors (Yu J, Hu K, Smuga-Otto K, Tian S, et al: Science 324, 797-801, 2009) for transfection have been developed.

Cells in which transformation into iPS cells, i.e., reprogramming, has occurred can be selected using, for example, expression of a pluripotent stem cell marker (undifferentiated marker) such as Fbox15, Nanog, Oct/4, Fgf-4, Esg-1 or Cript as an indicator. The selected cells are collected as iPS cells.

Several types of ES cells are provided from public institutions or commercially available. Examples of mouse ES cells include ES-E14TG2a cells (ATCC), ES-D3 cells or the like (ATCC), H1 cells (Riken BioResource Center, Tsukuba-city, Japan), B6G-2 cells (Riken BioResource Center, Tsukuba-city, Japan), R1 cells (Samuel Lunenfeld Research Institute, Toronto, Canada), mouse ES cells (129SV, catalogue number R-CMTI-1-15, R-CMTI-1A) (Dainippon Sumitomo Pharma Co., Ltd., Osaka, Japan) and mouse ES cells (C57/BL6, catalogue number R-CMTI-2A (Dainippon Sumitomo Pharma Co., Ltd., Osaka, Japan). Monkey ES cells are available from, for example, Stem Cell Research Center, Institute for Frontier Medical Sciences, Kyoto University. Human ES cells are available from, for example, Stem Cell Research Center, Institute for Frontier Medical Sciences, Kyoto University, WiCell Research Institute (Madison, USA), and ES Cell International Pte Ltd (Singapore). Methods for establishing ES cells have been achieved, and part thereof has been practice routinely. Therefore, one can himself establish desired ES cells using ordinary methods. For example, Nagy. A. et al. eds., *Manipulating the Mouse Embryo, A Laboratory Manual, Third Edition*, Cold spring Harbor Laboratory Press, 2003, *Jikken-igaku Bessatsu Baiyousaiboujikkenn Handbook* (Culture Cell Experiment Handbook (supplementary volume of Experimental medicine)), Yodosha Co., Ltd. may be referenced with respect to method for establishing mouse ES cells. For methods for establishing monkey ES cells, Suemori H, Tada T, Torii R, et al., Dev Dyn 222, 273-279, 2001, etc. may be referenced. For method for establishing human ES cells, Wassarman, P. M. et al.: Methods in Enzymology, Vol. 365 (2003), etc. may be referenced.

The CNS disease treatment composition is preferably free from serum. The absence of serum in the CNS disease treatment composition improves the safety of the composition. For example, a serum-free conditioned medium can be prepared by culturing dental pulp stem cells in a medium that does not contain any serum (serum-free medium). In the case of subculturing for one passage or plural passages, a serum-free conditioned medium can be obtained by carrying out subculturing for the last passage, or for the last few passages, in a serum-free medium. A serum-free conditioned medium can be obtained also by removing serum from a collected conditioned medium, using, for example, solvent substitution by dialysis or column.

The CNS disease treatment composition is utilized for treatment of diseases of central nerves (brain and spinal cord). Examples of CNS diseases to which the CNS disease treatment composition can be applied include spinal cord injury, neurodegenerative diseases such as amyotrophic lateral sclerosis, Alzheimer's disease, Parkinson's disease, progressive supranuclear palsy, Huntington's disease, multiple system atrophy and spinocerebellar ataxia, degeneration or loss of neuronal cells caused by cerebral ischemia, intracerebral hemorrhage or cerebral infarction, and a retinal disease involving a neuronal cell disorder. Application of the CNS disease treatment composition promotes regeneration and healing of CNS tissues due to its neurite outgrowth effects and/or its apoptosis inhibitory effects toward neuronal cells. Any disease or disorder to which treatment based on this mechanism is effective can be the target disease of the invention, regardless of the type or cause (for example, primary cause such as external injury or cerebral infarction or secondary cause such as infection or tumor) of the disease or disorder.

Spinal cord injury refers to a state in which the spinal cord is damaged by an external impact or by an internal factor such as a spinal tumor or hernia, and is classified according to complete-type (a state in which the spinal cord is completely severed at a certain point) and incomplete-type (a state in which the function of the spinal cord is partially maintained although the spinal cord is damaged or compressed), based on the degree of the damage. With the current medical technology, complete recovery from spinal cord injury cannot be achieved, and a new treatment method is desired to be established. Spinal cord injury is one of the diseases to which regenerative medicine is expected to be applied, and use of bone marrow, neural stem cells, embryonic stem cells, artificial pluripotent stem cells, etc. is under investigation. However, a decisive treatment technique has not been realized owing to various problems. Under such a circumstance, the CNS disease treatment composition provides a treatment method that is expected to provide a high therapeutic effect, and the significance and value thereof is quite high.

Other diseases or disorders to which the CNS disease treatment composition can be applied include cerebral infarction caused by degeneration or loss of neuronal cells caused by cerebral ischemia, intracerebral hemorrhage or the like in the acute phase or subacute phase, and periventricular leukomalacia, which is a neonatal encephalopathy caused by hypoxic ischemia during perinatal period. Cerebral ischemia is a state in which blood supply to the brain is insufficient, and oxygen and nutrients are not sufficiently supplied to the brain. Cerebral ischemia causes the death of neuronal cells and cerebral edema, and serves as a cause of cerebral infarction. The composition of the invention can be applied also to the treatment of destruction of neuronal cells due to cerebral ischemia or the like, or various diseases that accompany the destruction of neuronal cells.

Parkinson's disease, spinocerebellar ataxia, Alzheimer's disease, Huntington's disease, multiple system atrophy and progressive supranuclear palsy are intractable neural diseases caused by region-specific neuronal loss in the cerebrum, midbrain and cerebellum regions. The CNS disease treatment composition is able to exert a therapeutic effect by suppressing the neuronal degeneration and loss of in these diseases.

The CNS disease treatment composition can also be applied to retinal diseases accompanied by neuronal cell disorders. According to rough classification, five types of neuronal cells—photoreceptor cells (cone photoreceptor cells, rod photoreceptor cells), bipolar cells, horizontal cells, amacrine cells and ganglion cells—are present in retina. The CNS disease treatment composition exerts a therapeutic effect by suppressing the neuronal death and loss in retinal diseases caused by damage to one type, or two or more types, selected from these neuronal cells present in retina, as well as in retinal diseases with pathological conditions exhibiting damage to one type, or two or more types, selected from these neuronal cells, example of which include traumatic retinal detachment, retinal tear, concussion of retina, optic canal fracture, diabetic retinopathy, age-related macular degeneration, retinitis pigmentosa, glaucoma, choroideremia, Leber's hereditary optic neuropathy, cone dystrophy, familial drusen, central areolar choroidal dystrophy and autosomal dominant optic atrophy.

Other ingredients may additionally be used in the composition of the invention, as long as the expected therapeutic effect is maintained. Ingredients that can additionally be used in the invention include those listed below.

(i) Bioabsorbable Materials

Hyaluronic acid, collagen, fibrinogen (for example, BOL-HEAL (registered trademark)), etc., may be used as organic bioabsorbable materials.

(ii) Gelling Materials

Gelling materials for use preferably have high bioaffinity, and hyaluronic acid, collagen or fibrin adhesive or the like may be used. Various hyaluronic acids and collagens may be selected and used, and it is preferable to adopt those suitable for the purpose of application of the composition of the invention (the tissue to which the composition is to be applied). Collagens to be used are preferably soluble (acid-soluble collagens, alkali-soluble collagens, enzyme-solubilized collagens, etc.).

(iii) Others

Other pharmaceutically-acceptable ingredients (for example, carriers, excipients, disintegrants, buffer agents, emulsifying agents, suspending agents, soothing agents, stabilizers, preservatives, antiseptic agents, physiological saline, etc.) may be contained. Lactose, starch, sorbitol, D-mannitol, white sugar, etc. may be used as excipients. Starch, carboxymethylcellulose, calcium carbonate, etc. may be used as disintegrants. Phosphoric acid salts, citric acid salts, acetic acid salts, etc. may be used as buffering agents. Gum arabic, sodium alginate, Tragacanth, etc. may be used as emulsifying agents. Glycerin monostearate, aluminum monostearate, methylcellulose, carboxymethylcellulose, hydroxymethylcellulose, sodium lauryl sulfate, etc. may be used as suspending agents. Benzyl alcohol, chlorobutanol, sorbitol, etc. may be used as soothing agents. Propyleneglycol, ascorbic acid, etc. may be used as stabilizers. Phenol, benzalkonium chloride, benzylalcohol, chlorobutanol, methylparaben, etc. may be used as preservatives. Benzalkonium chloride, parahydroxybenzoic acid, chlorobutanol, etc. may be used as antiseptic agents. Antibiotics, pH adjusting agents, growth factors (such as nerve growth factor (NGF), brain-derived neurotrophic factor (BDNF)), etc. may also be contained.

The final form of the CNS disease treatment composition is not particularly limited. Examples of the form include liquid forms (such as a purely liquid form and a gel form), and solid forms (such as a powdery form, a fine grain form and a granular form).

Methods for producing the CNS disease treatment composition are not particularly limited. A production method that includes the following steps (1) to (3) is preferable:

(1) a step of selecting adhesive cells from dental pulp cells;

(2) a step of culturing the adhesive cells; and (3) a step of collecting a conditioned medium.

Each step is described in the following.

In step (1), dental pulp stem cells, which are adhesive cells, are selected from dental pulp cells. The dental pulp cells may be prepared by isolating from a living organism in advance. This selection step may include preparing dental pulp cells. A specific example of a procedure of a series of operations from the preparation of dental pulp cells to the selection of dental pulp stem cells is described below.

(a) Collection of Dental Pulp

A naturally-exfoliated deciduous tooth (or extracted deciduous tooth or permanent tooth) is disinfected using a chlorhexidine or ISODINE solution, and, thereafter, the tooth crown part is divided, and a dental pulp tissue is collected using a dental reamer.

(b) Treatment with Enzyme

The collected dental pulp tissue is suspended in a basal medium (Dulbecco's Modified Eagle's Medium containing 10% bovine serum and an antibiotic), and treated with 2 mg/mL collagenase and DISPASE at 37° C. for 1 hour. The dental pulp cells after the enzymatic treatment are collected by centrifugation (5,000 rpm) for 5 minutes. Cell separation using a cell strainer should basically not be carried out since it decreases the collection efficiency of neural stem cell fraction such as SHED or DPSC.

(c) Selection of Adhesive Cells

The cells are re-suspended in 4 cc of the basal medium, and seeded in a culture dish for adhesive cells having a diameter of 6 cm. After adding a medium (for example, Dulbecco's Modified Eagle's Medium (DMEM) containing 10% FCS), the cells are cultured in an incubator maintained at 5% $CO_2$ and 37° C. for about two weeks. After removing the medium, the cells are washed with, for example, PBS for once or a few times. This operation (the removal of the medium and the washing of the cells) may be replaced by harvesting adhesive cells (dental pulp stem cells) that have formed colonies. In this case, for example, treatment with 0.05% trypsin-EDTA is carried out at 37° C. for 5 minutes, and cells that have detached from the dish are harvested.

In step (2) following step (1), the selected adhesive cells are cultured. For example, the cells are seeded in a culture dish for adhesive cells, and cultured in an incubator maintained at 5% $CO_2$ and 37° C. Subculture is carried out, if necessary. For example, when visual observation confirmed that cells has reached subconfluence (the state in which cells cover about 70% of the surface area of the culture vessel) or confluence, the cells are detached from the culture vessel and harvested, and seeded again into a culture vessel filled with a culture medium. Subculture may be carried out repeatedly. For example, subculture may be carried out for one to eight passages, thereby allowing the cells to proliferate to the required cell number (for example, about $1 \times 10^7$ cells/mL). Here, the detachment of cells from the culture vessel can be carried out using an ordinary method such as treatment with trypsin. After the culture described above, the cells may be harvested and stored (in which the storage condition may be, for example, −198° C.). Cells collected from various donors may be stored in the form of a dental pulp stem cell bank.

The medium may be, for example, a basal medium or a basal medium supplemented with serum or the like. However, in the case of preparing a serum-free dental pulp stem cell-conditioned medium, a serum-free medium may be used throughout the entire process or at subculturing for the last passage or for the last few passages. DMEM, Iscove's Modified Dulbecco's Medium (IMDM) (GIBCO Corporation, etc.), Ham's F12 medium (HamF12) (Sigma-Aldrich Corporation, GIBCO Corporation, etc.), RPMI1640 medium, etc., can be used as the basal medium. Two or more basal media may be used in combination. An example of a mixed medium is a medium formed by mixing equivalent amounts of IMDM and HamF12 (commercially available as, for example, IMDM/HamF12 (tradename, GIBCO Corporation)). Examples of ingredients that can be added to the medium include serums (such as fetal bovine serum, human serum and sheep serum), serum replacements (knockout serum replacement (KSR), etc.), bovine serum albumin (BSA), antibiotics, various vitamins and various minerals.

In step (3) following step (2), the conditioned medium from the dental pulp stem cells selected and cultured by the above-described method is collected. For example, the conditioned medium can be collected by suctioning the culture medium using a dropper of a pipette. The collected conditioned medium is used as an active ingredient of the composition of the invention, directly or after being subjected to one or more treatments. Examples of the treatments include centrifugation, concentration, solvent substitution, dialysis, freezing, drying, freeze-drying, dilution, desalting and storage (for example, 4° C. or −80° C.). The dental pulp stem cell-conditioned medium exhibited the expected activity (neurite outgrowth activity and apoptosis inhibitory activity) even without complex high purification, as shown in the later-described Examples. This means that the composition of the invention effective for CNS diseases can be produced through simple steps. The absence of the necessity for complex purification step is advantageous also in that a decrease in activity caused by purification can be avoided.

In order to confirm the quality of the conditioned medium, the collected conditioned medium may be subjected to the following step (a) or step (b), or both.

(a) a step of checking the conditioned medium with respect to the presence or absence of a neurite outgrowth activity in the presence of a nerve regeneration inhibitory substance.

(b) a step of checking the conditioned medium with respect to the presence or absence of an apoptosis inhibitory activity toward neuronal cells.

A conditioned medium that exhibited a positive result in step (a) is expected to provide an excellent therapeutic effect by its neurite outgrowth activity. Similarly, a conditioned medium that exhibited a positive result in step (b) is expected to provide an excellent therapeutic effect by its apoptosis inhibitory activity toward neuronal cells. It is preferable to carry out both of step (a) and step (b), and use a conditioned medium that exhibited a positive result in both steps as an active ingredient of the composition of the invention. Methods for checking in steps (a) and (b) are as described above (in the section discussing the first aspect of the invention). The quality of a collected, prepared or stored conditioned medium can also be checked through steps (a) and (b). Therefore, it is understood that these steps themselves have high utility and value as a method of determining the quality of a dental pulp stem cell-conditioned medium (i.e., as a means for determining the suitability as an active ingredient for CNS disease treatment).

<Method of Concentrating Stem Cell-Conditioned Medium>

With regard to the damaged part treatment composition and the CNS disease treatment composition encompassed by the invention, physiologically active substances contained in the stem cell-conditioned medium can be formulated as a drug. This allows, for example, a nerve regenerative active substance to be formulated as a drug. For the method of concentrating the cell-conditioned medium for drug formulation, methods usually employed for this purpose may be applied. Examples of the concentration method include the following two methods.

1. Spin Column Concentration Method

The conditioned medium is concentrated (up to 75-fold) using an AMICON ULTRA CENTRIFUGAL FILTER UNITS-10K (manufactured by Millipore Corporation). Specific operation procedure thereof is as described below.

(i) Add the conditioned medium (up to 15 mL) into an AMICON ULTRA CENTRIFUGAL FILTER UNITS-10K, and centrifuge at 4000×g for about 60 minutes to concentrate to 200 µl.

(ii) Add the same amount sterile PBS as the conditioned medium into the tube, and centrifuge again at 4000×g for about 60 minutes to substitute the basal solution with the PBS.

(iii) Collect the 200 μl of obtained solution into a microtube. The collected solution serves as a concentrated stem cell-conditioned medium.

2. Ethanol Precipitation Concentration Method

The conditioned medium is concentrated (up to 10-fold) using an ethanol precipitation method. Specific protocol thereof is as follows.

(i) Add 45 mL of 100% ethanol to 5 mL of the conditioned medium, mix the solution well, and left at −20° C. for 60 minutes.

(ii) Centrifuge at 15,000×g at 4° C. for 15 minutes.

(iii) Remove a supernatant, add 10 mL of 90% ethanol, and stir well.

(iv) Centrifuge at 15,000×g at 4° C. for 5 minutes.

(v) Remove a supernatant, dissolve the resultant pellet in 500 μl of sterile water and collect the resultant solution in a microtube. The collected solution serves as a concentrated stem cell-conditioned medium.

<Method of Freeze-Drying Stem Cell-Conditioned Medium>

The stem cell-conditioned medium in the composition of the invention may be freeze-dried. This provides excellent storage stability. The method of freeze-drying the stem cell-conditioned medium may be any method usually employed for this purpose. Examples of the freeze-drying method include the following method:

(i) freezing the stem cell-conditioned medium or concentrated stem cell-conditioned medium obtained by the above-described method at −80° C. for 2 hours to half a day.

(ii) opening the cap of the sample tube after the freezing, and set the sample tube to a freeze-dryer.

(iii) freeze-drying the sample for one to two days.

(iv) obtaining the resultant sample, which serves as a freeze-dried stem cell-conditioned medium (capable of being stored at −80° C.).

A further aspect of the invention provides a method of treating a CNS disease which includes a step of administering a therapeutically effective amount of the CNS disease treatment composition to a CNS disease patient. The administration route of the composition of the invention is not particularly limited as long as the composition is delivered to the target tissue. The composition may be applied, for example, by topical administration. Examples of the topical administration include injection into the target tissue or application to the target tissue. The composition of the invention may be administered by intravenous administration, intraarterial administration, intraportal administration, intradermal administration, subcutaneous administration, intramuscular administration or intraperitoneal administration. The dosage regimen may be, for example, from once to several times a day, once every two days, once every three days, or the like. The dosage regimen may be prepared in consideration of the sex, age, weight, pathological condition, etc. of the subject (recipient). The subject to which the composition of the invention is administered is typically a human patient suffering from a CNS disease. However, application to mammals other than human (including pet animals, farm animals and laboratory animals, specific examples of which include mice, rats, guinea pigs, hamsters, monkeys, cattle, pigs, goats, sheep, dogs, cats, etc.) is also contemplated. The composition of the invention is administered preferably to a subject in the acute or subacute phase, so that the effects of the composition of the invention are most exerted.

Simultaneously with or after the administration of the CNS disease treatment composition, dental pulp stem cells may be administered to the same subject, thereby providing a complex or continuous effect, according to an embodiment of the invention. Here, undifferentiated dental pulp stem cells that have not been subjected to differentiation inducing treatment after obtainment thereof, or differentiation-induced dental pulp stem cells that have been induced to differentiate into a neural cell after obtainment thereof, may be used as the dental pulp stem cells. In the case of administering dental pulp stem cells simultaneously with the administration of the CNS disease treatment composition, it is preferable to administer undifferentiated dental pulp stem cells in order that high therapeutic effects are exerted. In the case of administering dental pulp stem cells after the administration of the CNS disease treatment composition, it is preferable to use differentiation-induced dental pulp stem cells that have been induced to differentiate into neural cells. It is also possible to use pluripotent stem cells (such as iPS cells or ES cells) that have been induced to differentiate into neural cells in addition to, or in place of, the differentiation-induced dental pulp stem cells.

Examples of the invention are described below, but not limited thereto. In the examples, "%" is based on weight (mass) unless otherwise specified.

EXAMPLES

Example 1

Materials and Methods (1) Subjects and Cell Cultures

Human dental pulp tissues were obtained from clinically healthy extracted deciduous teeth and permanent teeth from eight patients. These experimental protocols were approved by the ethics committee of Nagoya University. SHED and DPSCs were isolated and cultured as described in Proc Natl Acad Sci USA 2000; 97: 13625-30 or Proc Natl Acad Sci USA 2003; 100: 5807-12.

Briefly, the pulp was gently removed and digested in a solution of 3 mg/mL collagenase type I and 4 mg/mL dispase at 37° C. for 1 hour. After filtration using 70-mm cell strainers (Falcon; BD Labware, Franklin Lakes, N.J.), cells were cultured in Dulbecco's Modified Eagle Medium (DMEM; GIBCO, Rockville, Md.) containing 20% mesenchymal cell growth supplement (Lonza Inc, Walkersville, Md.) and antibiotics (100 U/mL penicillin, 100 mg/mL streptomycin and 0.25 mg/mL amphotericin B; GIBCO) at 37° C. with 5% $CO_2$. After primary culture, the cells were subcultured at about $1 \times 10^4$ cells/$cm^2$. Cells passaged from once to three times were used in the experiments. Human BMMSCs were purchased from Lonza Inc., and cultured according to the manufacturer's instructions.

(2) Analysis of Cell Proliferation

The proliferation rates of SHED, DPSCs and BMSCs were assessed by bromodeoxyuridine (BrdU) incorporation for 12 hours using a BrdU staining kit (Invitrogen, Carlsbad, Calif.) according to the manufacturer's instructions (n=3 for each group). The experiment was repeated five times. Statistically significant differences were evaluated by the Tukey-Kramer test following one-way analysis of variance.

For STRO-1 immunofluorescence, SHED, DPSCs and BMSCs were fixed with 3% paraformaldehyde, and then rinsed twice with phosphate-buffered saline, and treated with 100 mM glycine for 20 minutes. Cells were then permeabilized with 0.2% Triton-X (Sigma-Aldrich, St. Louis, Mo.) for 30 minutes, and subsequently incubated in a mixture of 5% donkey serum and 0.5% bovine serum albumin for 20 minutes. Next, the cells were incubated with a mouse anti-human STRO-1 antibody (1:100; R&D, Minneapolis, Minn.) as a primary antibody for 1 hour, incubated for 30 minutes with a goat anti-mouse immunoglobulin M-FITC antibody (1:500; Southern Biotech, Birmingham, Ala.) as a secondary antibody, and mounted using Vectashield with DAPI (Vector Laboratories Inc, Burlingame, Calif.).

(3) Animal Experiment (FIG. 1)

Five-week-old female hairless mice (Hos: HR-1) were provided from SLC Inc. (Shizuoka, Japan). All mice were housed in climate-controlled quarters (22±1° C. at 50% humidity) with a 12/12-hour light/dark cycle. Animals were allowed free access to water and a chow diet, and were observed daily. The mice were irradiated dorsally using a UVB-emitting system RMX-3W (Handok Biotech, Seoul, Korea) for eight weeks, five times a week. A bank of 10 Toshiba SE lamps was used without any filtering for UVB (peak of emission being about 312 nm, and the irradiance between 290 and 320 nm corresponding to 55% of the total amount of UVB). The distance from the lamps to the animals' backs was 89 cm. During exposure, the animals were allowed to move around freely in their cages. The irradiation dose was 1 MED (minimal erythemal dose; 60 mJ/cm$^2$) in the first two weeks, 2 MEDs (120 mJ/cm$^2$) in the third week, 3 MEDs (180 mJ/cm$^2$) in the forth week, and 4 MEDs (240 mJ/cm$^2$) in the fifth through eight weeks. The total UVB dose was approximately 115 MEDs (6.9 J/cm$^2$). Five weeks after wrinkle induction, SH-CM (100%) was subcutaneously injected into the restricted area of the mice. In a positive control, PBS-suspended SHED (4×10$^5$) was injected directly into the dermis. In a negative control, the dermis was treated by PBS only.

(4) Preparation of SH-CM

SHED (4×10$^5$ cells) were cultured in DMEM/F12 (Invitrogen-Gibco-BRL, Grand Island, N.Y.) serum-free medium. Conditioned medium of SHED was collected after 72 hours of culture, centrifuged at 300×g for 5 min, and filtered using a 0.22 mm syringe filter.

(5) Skin Replica and Image Analysis

At the time of wrinkle induction and one week after the injection, negative replicas of the dorsal skin surface were taken using a silicon-based impression material, FLEX-TIME1 (Heraeus Kulzer, New York, N.Y.). To obtain replicas of the wrinkles from the same skin area, the skin was marked using an oil-based marker pen. Five weeks after the final injection of SH-CM or SHED to the skin, impressions were taken from the marked area. For ease of measurement, all replicas were cut into square pieces of 1 cm, and the back of each replica was processed into a flat plane using the same impression material. Light was directed at an angle of 208°, and images were incorporated from the replica using a CCD camera. The image of the negative replicas was observed using a wrinkle analysis system, skin visiometer SV 600 (Courage & Khazaka, Cologne, Germany). The parameters used in the assessment of the skin wrinkles are number, depth and area thereof.

(6) Histology

Dorsal skins (1 cm×1 cm) were fixed with a 10% formalin neutral buffered solution, embedded in polyester wax, and sectioned at 6 mm. The sections were subjected to Hematoxylin & Eosin (H&E) staining and Masson's trichrome staining.

(7) HDF Culture and UVB Irradiation Dose

HDFs were cultured in a DMEM supplemented with 10% fetal bovine serum, 100 U/mL penicillin and 100 mg/mL streptomycin at 37° C. with 5% $CO_2$. After starvation with serum-free medium for 24 hours, cells were washed with PBS, and exposed to UVB with 3 to 4 drops of PBS. UVB irradiation was carried out using a UV light source (Waldmann, Schwenningen, Germany). Immediately after the irradiation, the PBS was aspirated, and replaced with a complete medium. UVB irradiation doses were varied in the range of from 50 to 250 mJ/cm$^2$ during the test, and finally fixed to 70 mJ/cm$^2$ for further experimentation.

(8) Cell Proliferation Assay

HDFs were plated at a density of 5×10$^3$ cells/well in 96-well plates, and the proliferation of HDFs was measured using a CCK-8 Kit (Dojindo, Gaithersburg, Md.). After starvation for 24 hours in a serum-free medium, the cells were continuously cultured for 24 hours with or without SH-CM, and were exposed to UVB (70 mJ/cm$^2$) for 90 seconds. Then, UVB-irradiated cells were cultured in a complete medium for 24 hours and harvested. HDFs were added to 10 mL of the CCK-8 solution, and incubated for 3 hours. The absorbance was measured at 450 nm using a microplate reader (TECAN, Grodig, Austria). OD values of each well were converted into their relative cell numbers based on a comparative standard curve.

(9) Western Blot Analysis

HDFs (2×10$^4$ cells/well) were seeded in 24-well plates, and pretreated as described above. Then, the cells were lysed in a RIPA buffer (50 mM Tris-HCl, 0.15 M NaCl, 1 mM EDTA, 1% Triton X-100, 1% SDS, 50 mM NaF, 1 mM $Na_3VO_4$, 5 mM dithiothreitol, 1 mg/mL leupeptin and 20 mg/mL PMSF, pH 7.4). Fifty micrograms of proteins were separated on an 8% SDS-polyacrylamide gel by electrophoresis. The proteins were transferred to a PVDF membrane. The membrane was incubated with an anti-collagen type I antibody (Santa Cruz, Saint Louis, Mo.) and an anti-matrix metalloproteinase-1 (MMP-1) antibody (Calbiochem, Darmstadt, Germany). Then, the membrane was washed, and incubated with horseradish peroxidase-conjugated antigoat IgG antibody (1:10,000, Santa Cruz, Saint Louis, Mo.). The blots were reacted with an immunoglobulin western reagent, and were exposed to X-ray film.

Results (1) Characterization of SHED, DPSCs and BMSCs.

Figure 2:
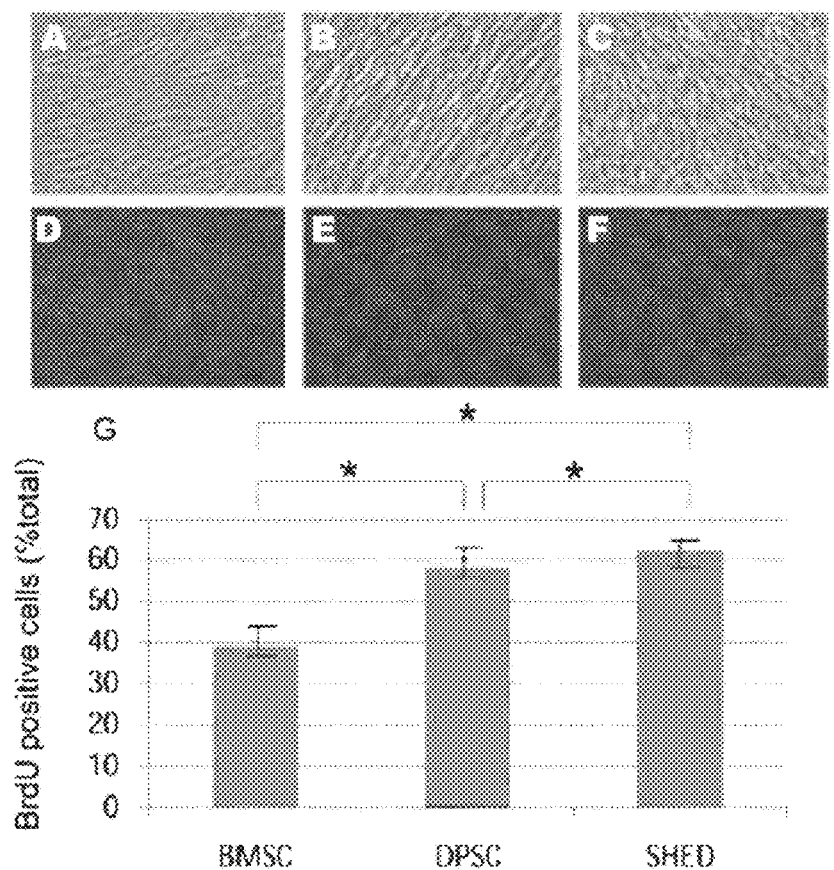
FIG. 2 is a view showing the morphology, immunological analysis and proliferation rates of various types of cells. (A) to (C) respectively represent (A) BMSC, (B) DPSC and (C) SHED (×40). (D) to (F) represent immunofluorescence staining images of the stem cell marker STRO-1. (D) BMSC, (E) DPSC and (F) SHED were positive for STRO-1 (green fluorescence). DAPI was used to visualize the nuclei (blue fluorescence). (G) The proliferation rates of SHED, DPSCs and BMSCs were assessed using BrdU. Bar: standard deviation. Significance: *$P<0.05$.

SHED and DPSCs displayed a fibroblastic morphology resembling BMSCs (FIG. 2A-C). Immunofluorescence analysis indicated that SHED, DPSCs and BMSCs contained STRO-1 positive cells (FIG. 2D-F). The proliferation rate of SHED was significantly higher than those of DPSCs and BMSCs (FIG. 2G).

(2) SH-CM Alleviated UV-Induced Wrinkles

Figure 3:
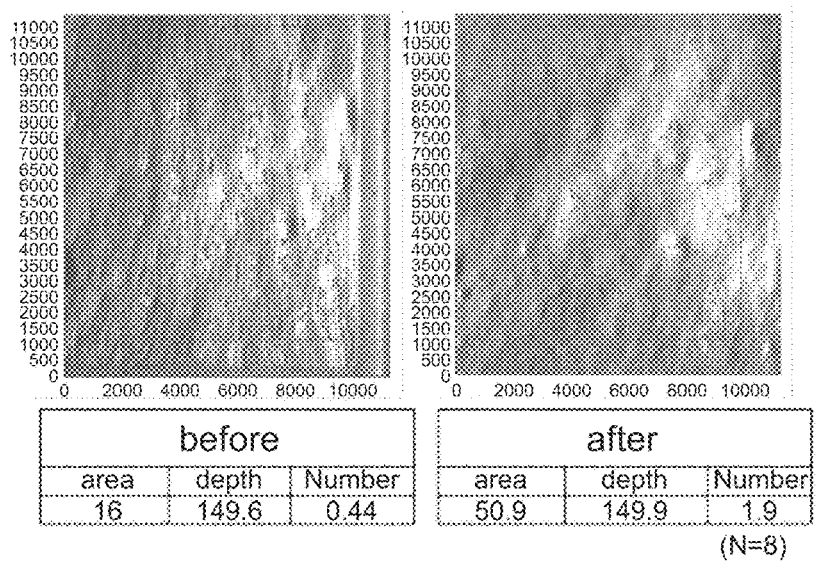
FIG. 3 is a view showing evaluation of wrinkles by replica analysis after SH-CM injection. (A) a group to be treated, (B) a group treated with 100% SH-CM.
Figure 4:
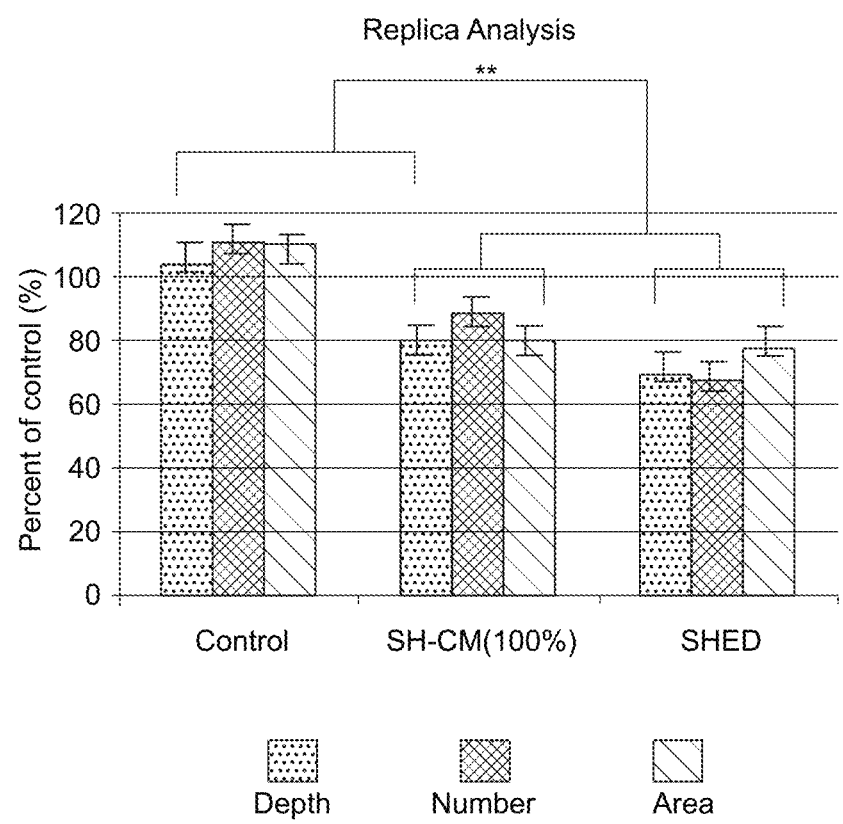
FIG. 4 is a diagram demonstrating amelioration of wrinkles in natural level of SH-CM- and SHED-injected group.

During the period of UV exposure, the mice were observed for fine wrinkling of the skin. However, the SH-CM treated group and the SHED injected group appeared to have fewer wrinkles than the PBS group during the treatment (n=8 for each group). In a replica analysis, FIG. 3 and FIG. 4 show that repeated SH-CM treatment alleviated the fine wrinkles induced by UVB irradiation. The SHED injected group showed the same tendency as that of the SH—CH group. When the inventors measured the parameters for the wrinkles of replicas with the skin visiometer SV 600, injection of natural-level (100%) of SH-CM significantly reduced all parameters for wrinkles. However, SHED-treated skin exhibits higher effectiveness than the SH-CM group.

(3) Histological Observation

Figure 5:
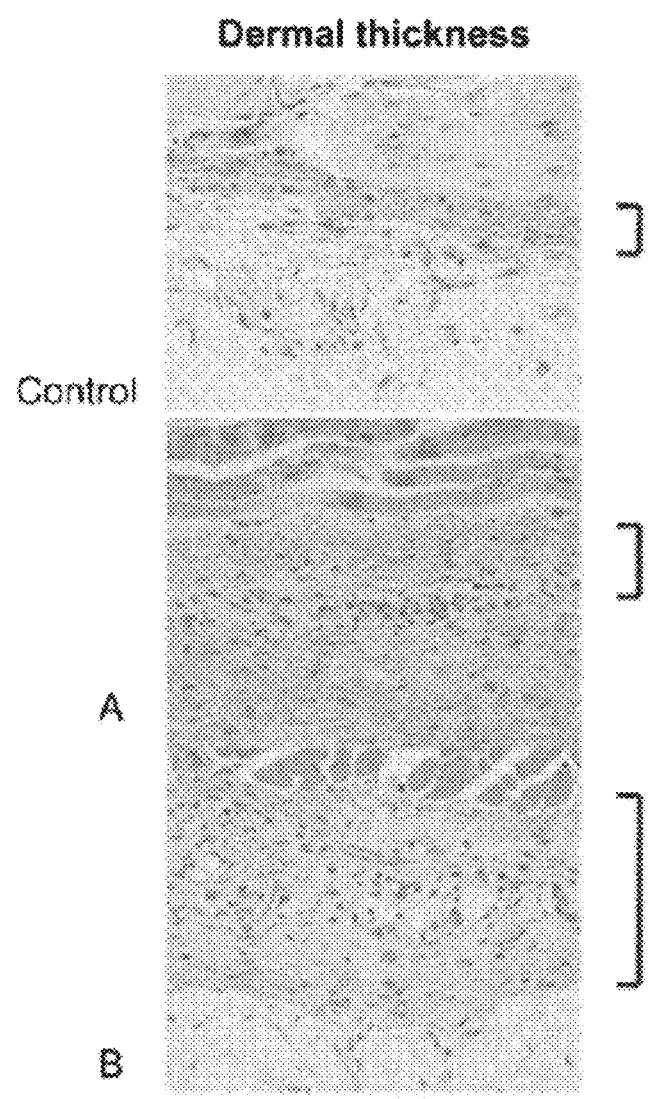
FIG. 5 is a view showing Hematoxylin-Eosin staining images. (A) SH-CM-treated group. (B) SHED-injected group.
Figure 6:
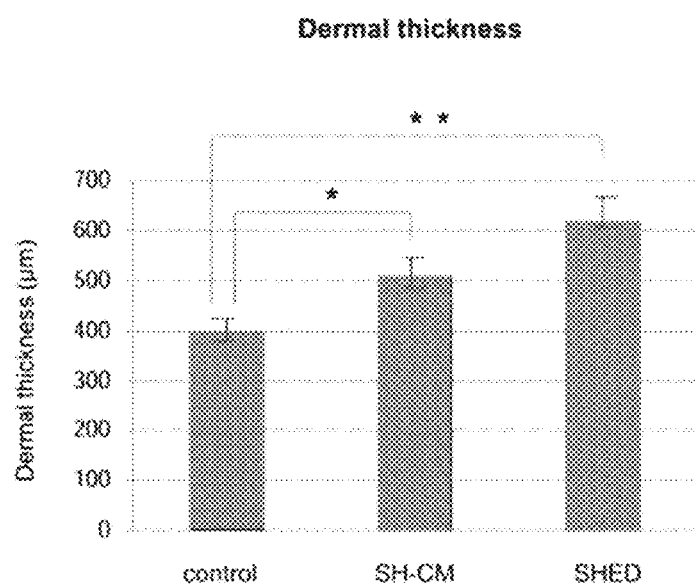
FIG. 6 is a graph comparing the dermal thicknesses.

The effect of SH-CM on dermal thickness in UVB irradiated hairless mice, which showed great changes in skin appendages, was investigated. FIG. 5 shows the histological measurements of the dermal thickness of the hairless mouse skin by H&E staining. Collagen fibers are stained as shown in FIG. 5, and the degree of staining is remarkably high in the SH-CM treated group (A) and the SHED injected group (B). Measurement of the dermal thickness showed significant increases in the SHED injected group and the SH-CM treated group (FIG. 6). Further, a marked increase of collagen bundles was observed in both groups, but was not observed in the control group (FIG. 5).

(4) SH-CM Increased Proliferation of HDFs

Figure 7:
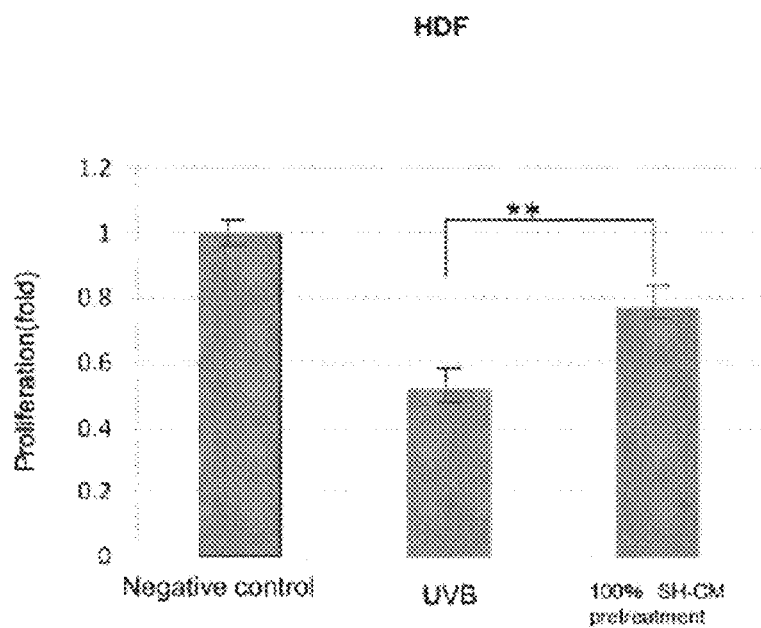
FIG. 7 is a diagram showing an effect of SH-CM on the proliferation of HDF.

In order to further study the paracrine mechanism with respect to the alleviation of skin wrinkles by SHED, a cell proliferation assay was performed in HDFs that had been primarily cultured with SH-CM. Although UVB irradiation significantly decreased the proliferation of HDFs, pretreatment with SH-CM showed a protective effect on HDFs (FIG. 7). SH-CM contains diverse growth factors, and in a case in which a unique characteristic of the growth factors is their ability to initiate mitosis of quiescent cells, it is possible that enhanced proliferation by SH-CM in this experiment is mediated by the growth factors secreted from SHED.

(5) Expression of Collagen Type I and MMP-1

Figure 8:
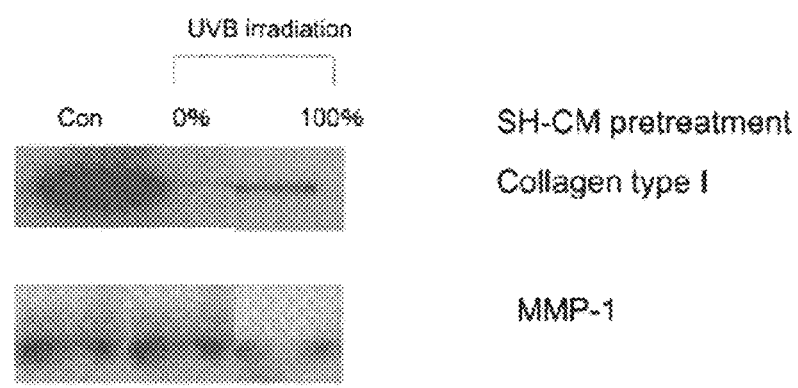
FIG. 8 shows a western blotting analysis demonstrating an effect of SH-CM on collagen type I and MMP-1.

Since the collagen content in the dermis was significantly increased in the SH-CM treated hairless mice, protein expressions of collagen type I and MMP-1 were examined in HDFs after the SH-CM treatment (FIG. 8). UVB irradiation clearly reduced the protein expression of collagen type I and induced that of MMP-1. However, the protein expression of collagen type I was significantly increased after the SH-CM pretreatment, while that of MMP-1 was decreased after the SH-CM pretreatment. These results indicate that the increased collagen content in the dermis of the SH-CM treated hairless mice was mediated by the stimulation of collagen synthesis and the inhibition of collagen degradation in the dermal fibroblasts.

Discussion

The characteristics of SHED were compared with those of DPSCs and BMSCs, which are considered as standard stem cell sources in tissue engineering and regenerative medicine. The results indicated that SHED possesses high proliferation ability, which is enhanced in the presence of an extracellular matrix, suggesting that SHED is a useful source for stem cell-based therapy. STRO-1 positive cells were found in SHED, DPSCs and BMMSCs. STRO-1 is known to recognize a trypsin-resistant cell-surface antigen present on a subpopulation of bone marrow cells, including a predominant proportion of skeletal stem cell having high growth and differentiation potential, and colony forming unit fibroblastic populations. High proliferative capacity is one of the most critical characteristics of postnatal somatic stem cells. The proliferation study using BrdU revealed that SHED shows the highest population rate among SHED, DPSCs and BMSCs. It was previously reported that micro array analysis revealed that SHED expresses multiple growth factors such as FGF, TGF-b, CTGF, NGF and BMP associated with this pathway, at high levels (S. Nakamura, Y. Yamada et al., *Stem Cell Proliferation Pathways Comparison between Human Exfoliated Deciduous Teeth and Dental Pulp Stem Cells by Gene Expression Profile from Promising Dental Pulp*, JOE, Vol. 35, (11), 1536-1542, 2009). FGF2 was reported as a cytokine that acts to promote the proliferation of numerous kinds of cells and control extracellular matrix generation during tissue regeneration and wound healing.

Paracrine factors, such as VEGF, KGF or FGF, may be used for skin regeneration, and this suggests that stem cell transplantation is also a "cell-based" cytokine therapy. Importantly, conditioned media containing growth factors can be used in order to avoid the negative effect of UVB on HDFs. The concept of paracrine effects mediating at least part of the effects of stem cell therapy is not inconsistent with previous data. Cell-based cytokine therapy can provide benefits in wound healing. Keratinocyte differentiation by SHED-derived growth factors may contribute to re-epithelialization in wound closure. Further, SHED-derived growth factors can provide benefits in wound healing, tissue remodeling and skin graft genesis.

Photoaging is a complex process having pathologic similarities to skin wounds. MSCs play a key role in this process, and interact with keratinocytes, fat cells and mast cells. MSCs are also a source of extracellular matrix proteins, of which fibrillar type I and type III collagens are significantly reduced in the papillary dermis, and their reduction has been shown to correlate well with the clinical severity of photoaging. This reduction results from a combination of reduced procollagen biosynthesis and increased enzymatic breakdown via the actions of MMP. Fisher et al. showed that UV irradiation induced the synthesis of MMP in human skin in vivo (Phipps R P, Borrello M A, Blieden T M., *Fibroblast heterogeneity in the periodontium and other tissues*, J Periodontal Res. 1997 January; 32(1 Pt 2):159-165; Fisher G J, Datta S C, Talwar H S, Wang Z Q, Varani J, Kang S, et al., *Molecular basis of sun-induced premature skin ageing and retinoid antagonism*. Nature 1996; 379: 335-339). Among the MMP family, MMP-1, MMP-13 and membrane-type MMP-14 display collagenolytic activity, and MMP-2 and MMP-9 were reported to be true elastases. MMP-mediated collagen and elastin destruction accounts for a large part of the connective tissue damage that occurs in photodamaged skin (Tsukahara K, Nakagawa H, Moriwaki S, Takema Y, Fujimura T, Imokawa G., *Inhibition of ultraviolet-B-induced wrinkle formation by an elastase-inhibiting herbal extract: implication for the mechanism underlying elastase-associated wrinkles*, Int J Dermatol 2006; 45: 460-468).

In this study, it was found that SH-CM not only inhibits a UVB-induced decrease of the type I collagen but also attenuates UVB-induced MMP-1 expression in HDFs. Wound healing and skin rejuvenation from photodamage are complex but orderly processes and are orchestrated via cytokines and growth factors. Therefore, these data, when combined with the present study, imply that local cytokine release may be an important factor mediating the beneficial SHED rejuvenation effects observed after delivery of SH-CM. Local delivery of SHED may contribute to healing also through returning circulating stem progenitor cells to the region of injury.

In conclusion, under a circumstance in which the application of SHED for dermal wound healing was still speculative, the interaction between SHED-derived growth factors and HDFs was investigated for the first time. SHED exerts effects on HDFs by causing an increase in collagen synthesis and by activating the proliferation and migration activity of HDFs, suggesting that SHED or SH-CM can be used for the treatment of photoaging and wound healing. The results also suggest that SHED is more suitable for dermal wound healing compared with MSCs, in terms of properties thereof. Mainly with secreted growth factors or ECM proteins, SHED contributes to enhance wound healing potential of HDFs.

Example 2

(1) Preparation of Growth Factor Mixture (Powder)

Immortalized human mesenchymal stem cells (MSCs: Ronza Co., Ltd, USA) were used to prepare a growth factor (GF) admixture. The cells were cultured for 2 to 8 passages using 10% FSC-containing DMEM. At a stage of 80% confluence of cells in the culture dish, the supernatant (culture medium: CM) was sampled. The sampled CM was then added to ethanol (CM: Ethanol=1:9), and incubated at −20° C. for 60 min. The CM was concentrated by spinning (4° C., 1500 rpm, 15 min). The remaining CM was washed with 90% ethanol at −20° C., and then spun again.

The concentrated CM was freeze-dried, thereby obtaining a growth factor powder.

(2) Growth Factors in the Powder

Each growth factor in the powder was analyzed by the Western-blotting method. The detected growth factors are as follows: PDGF, VEGF, IGF, KGF, HGF and TGF.

Example 3

Experimental Study of Bone Regeneration by Growth Factor (1) Methods

Four cylinder-shaped bone defects, each having a diameter of 10 mm and a depth of 10 mm, were formed in the dog mandible.

A titanium implant (3.75 mm in diameter) was inserted into the center of each defect.

Figure 10:
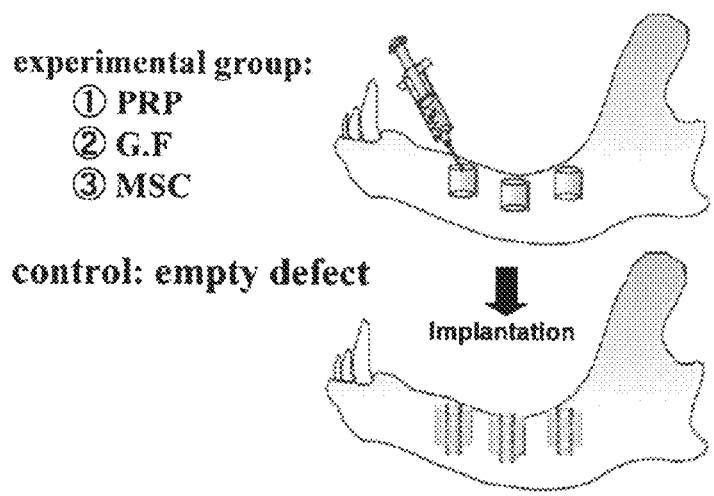
FIG. 10 is an explanatory diagram illustrating the experimental method according to Example 3 of the invention.

The spaces around the implant were filled with graft materials, such as (1) PRP, (2) 100% GF, (3) MSCs (1×1,000,000) and (4) empty defect (control) (FIG. 10).

(2) Results

Figure 11:
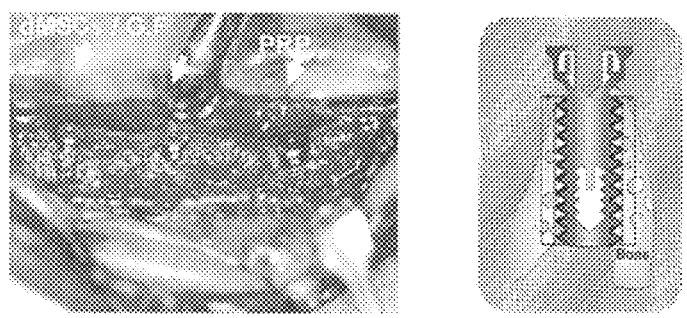
FIG. 11 is a view explaining the calculation of the BIC value employed in Example 3 of the invention.

Eight weeks later, the dog was euthanized and the mandible with the implants was dissected. A histological specimen was made and BIC (Bone-Implant Contact) was calculated using a light microscope and an image analyzing system (FIG. 11).

* BIC=total length of bone contact to implant surface/total length of implant surface×100(%)

Figure 12:
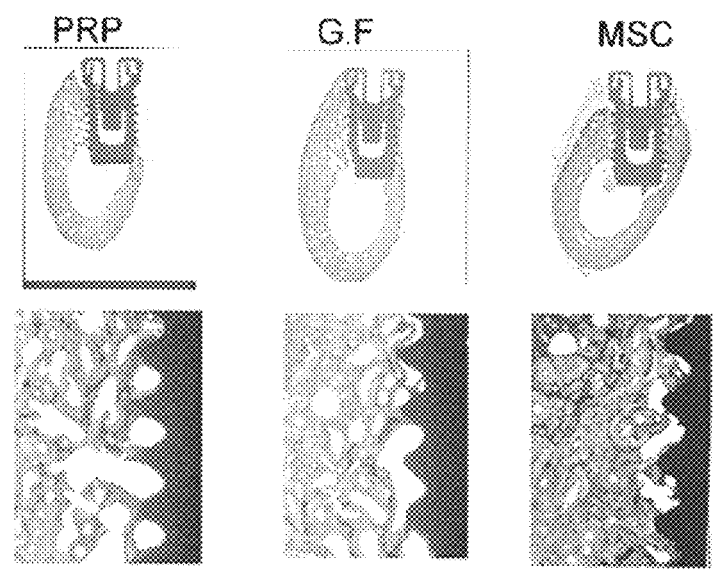
FIG. 12 shows staining images obtained as a result of Example 3 of the invention.
Figure 13:
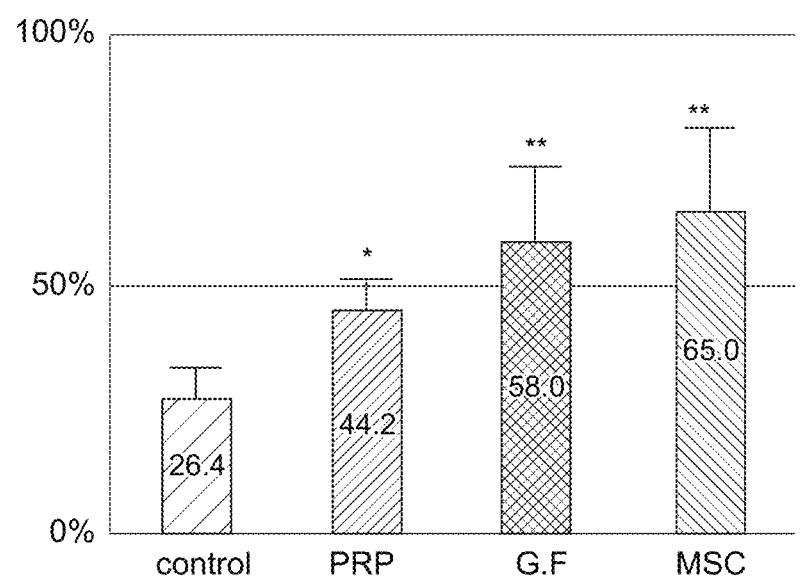
FIG. 13 is a diagram showing the results of Example 3 of the invention.

There was no significant difference in BIC between MSC (65.0) and GF (58.6), and the respective BIC values in MSC and GF were much higher than those of the control (26.4) and PRP (44.2) (FIGS. 12 and 13).

(3) Conclusion

In conclusion, growth factors derived from a mesenchymal stem cell have similar abilities to a living stem cell with respect to bone regeneration.

Clinical Case: 56 Years-Old Male

Figure 14:
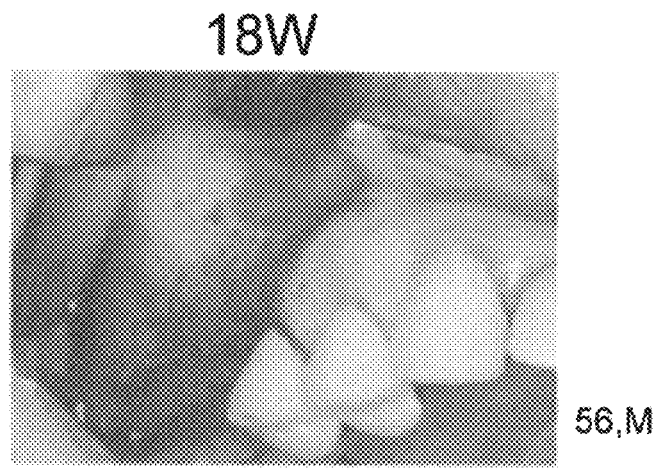
FIG. 14 is a photograph demonstrating the results of Example 3 of the invention.
Figure 15:
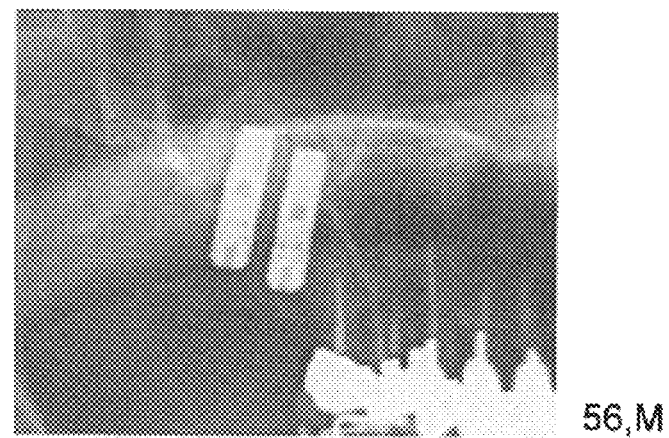
FIG. 15 is an X-ray photograph showing the results of the clinical case of Example 3 of the invention.

The sinus lift procedure with installation of two implants was performed at a post molar region in maxilla. A 100% cell-based GF with b-TCP (β-tricalcium phosphate) granules was grafted into the sinus cavity. Eight weeks later, the grafted portion was successfully filled with new bone, and osteointegration between the implants and the bone was confirmed by X-ray observation (FIGS. 14 and 15).

Example 4

Experimental Study of Periodontal Tissue Regeneration by Growth Factor (1) Methods A two-wall type periodontal defect was made in the distal portion of molar teeth in the dog mandible (FIG. 16). The defect in each dog was treated by the following method or procedure (FIGS. 17 and 18).

1) Flap Operation (FO, Control)
2) GTR method
3) MSCs (1×100,000)
4) GF (100%)

(2) Results

Figure 20:
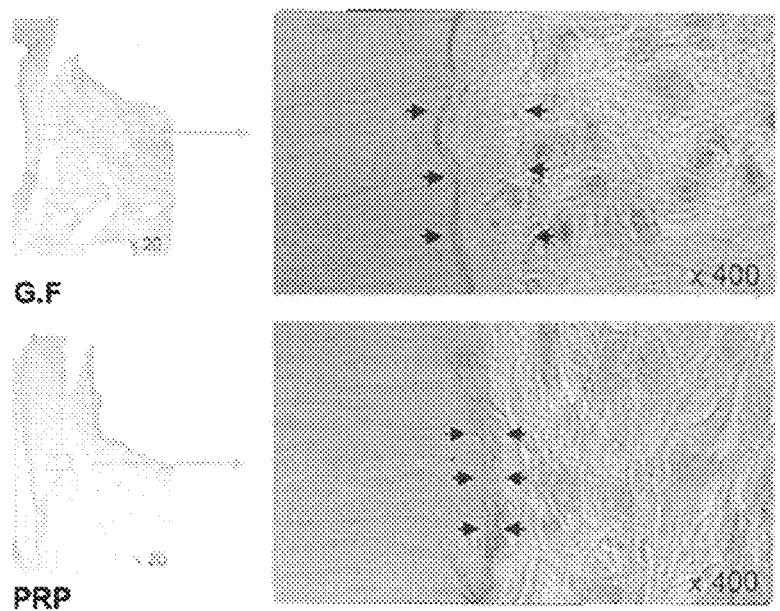
FIG. 20 shows staining images showing the regeneration state of the cementum obtained as a result of Example 4 of the invention. The upper photographs show the case of using GF, and the lower photographs show the case of using PRP.
Figure 21:
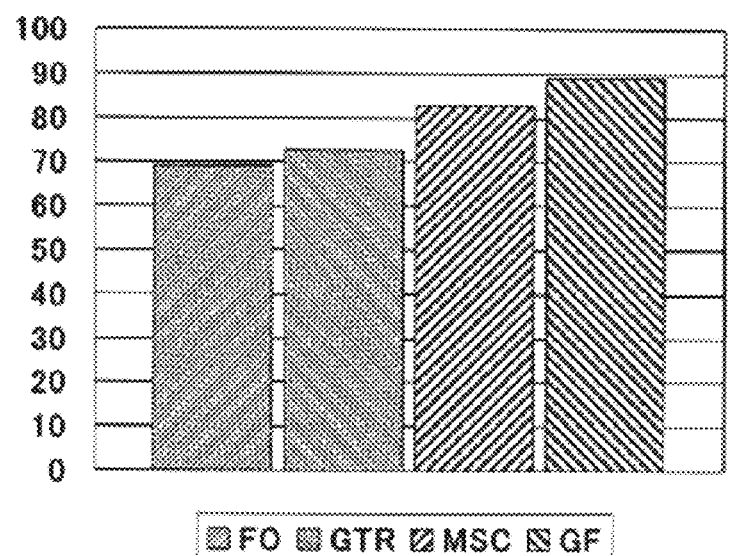
FIG. 21 is a graph showing the results of Example 4 of the invention ($N_2$-NC).
Figure 22:
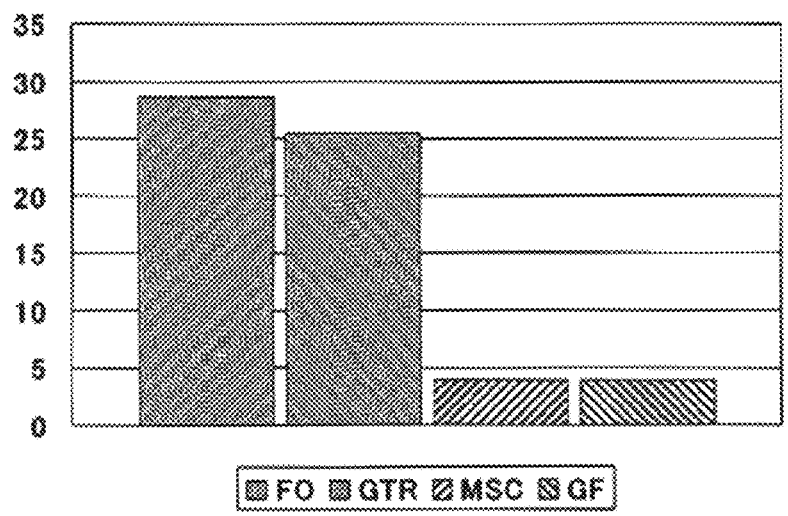
FIG. 22 is a graph showing the results of Example 4 of the invention ($N_1$-JE).

At 8 weeks after surgery, the dog mandible with molar teeth and gingiva was dissected, and a histological specimen thereof was made. By the histological observation, the depth of the pocket ($N_1$-JE; length of the epithelium down growth) and the length of new cementum ($N_2$-NC) were evaluated using a light microscope (FIG. 19). These parameters were useful for the evaluation of the amelioration of periodontal disease. The length of new cementum was much longer in GF and MSC than in GTR and the control. Further, the GF and MSC groups showed remarkable improvement in the depth of pocket, compared with the GTR and control groups (FIGS. 20 to 22).

(3) Conclusion

The MSC-derived growth factor has similar capacity to MSC themselves in terms of periodontal tissue regeneration.

Case Report: 64 Year-Old Female

Figure 23:
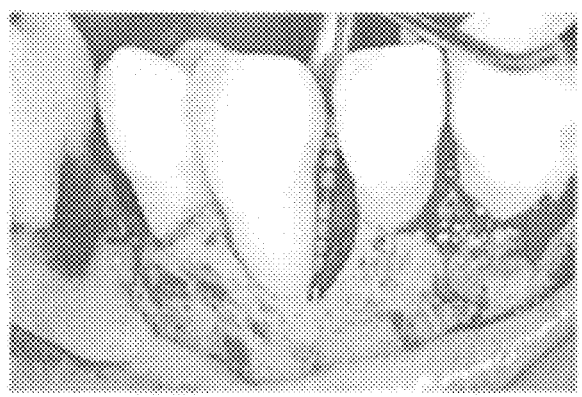
FIG. 23 is a photograph showing the pretreatment in the clinical case of Example 4 of the invention.
Figure 24:
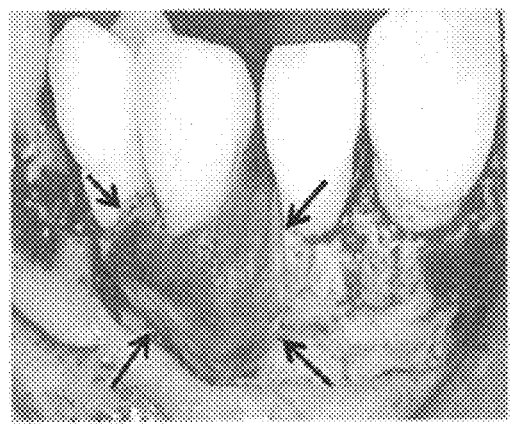
FIG. 24 is a photograph explaining the manner of treatment in the clinical case of Example 4 of the invention.
Figure 25:
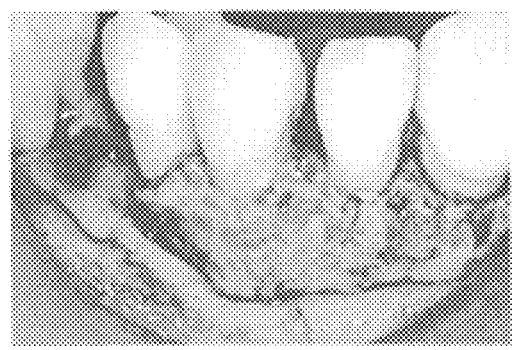
FIG. 25 is a photograph showing the results of the clinical case of Example 4 of the invention.

The medial portion of the lower right canine had a deep periodontal defect having a depth of 7 mm. The aterocollagen sponge with 100% GF was filled into the defect (FIGS. 23 and 24). Sixteen weeks later, the defect seemed to be clinically repaired with a newly formed periodontal tissue (FIG. 25).

As described above, cytokine therapies have an advantage over stem cell therapies in terms of safety, stability, easy manipulation, easy preservation, easy transportation and low cost.

Example 5

Confirmation of Therapeutic Effects on Cerebral Infarction

Cerebral Ischemia Model

Figure 26:
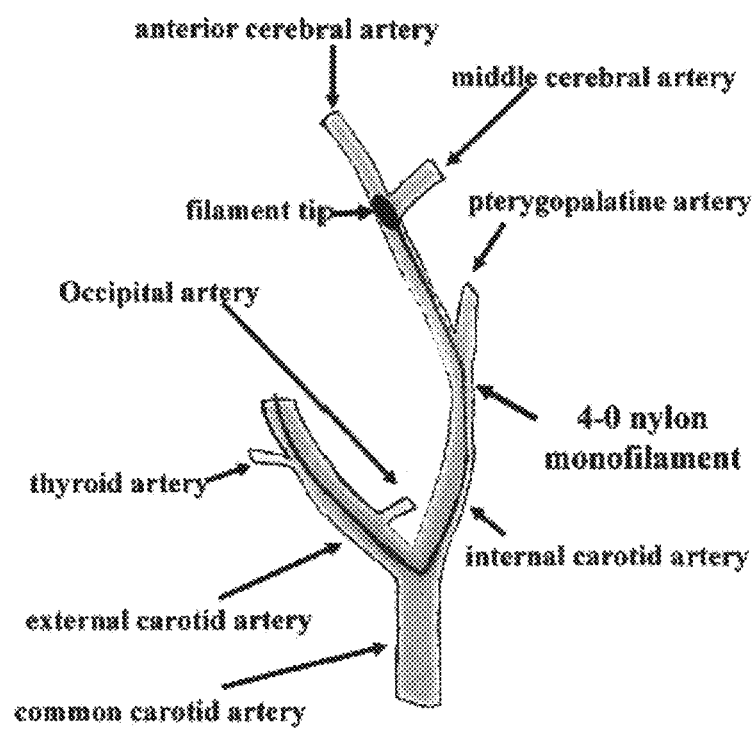
FIG. 26 is a diagram illustrating the induction of cerebral infarction according to Example 5 of the invention.

All animal experiments were approved by the Institutional Animal Care and Use Committee (Nagoya University Graduate School of Medicine). Adult male Sprague Dawley rats (Japan SLC Inc., Shizuoka, Japan) weighing 300-400 g were used. The animals were initially anesthetized with 5% isoflurane (Abbott Laboratories, North Chicago), and maintained under anesthesia with 1.5% isoflurane in a mixture of 70% $N_2O$ and 30% $O_2$. Their rectal temperature was maintained at 37° C.±0.5° C. on a heating pad. Focal cerebral ischemia was induced by permanent focal cerebral ischemia (pMCHO) (day 0) (FIG. 26). A 4-0 monofilament nylon suture (Shirakawa, Tokyo, Japan) with the tip rounded by flame heating and silicone (KE-200, Shin-Etsu Chemical, Tokyo, Japan) was advanced from the external carotid artery into the internal carotid artery until it blocked the origin of the MCA. The regional cerebral blood flow of the MCA territory was measured using a laser-Doppler flowmeter (Omega FLO-N1: Omega Wave Inc, Tokyo, Japan) after occlusion. The response was considered positive and included only if the reduction in regional cerebral blood flow was greater than 70%.

Intranasal Administration of SH-CM

Seventy-two hours after pMCAO (day 3), the rats were again anesthetized with 5% isoflurane (Abbott Laboratories, North Chicago), and maintained under anesthesia with 1.5% isoflurane in a mixture of 70% $N_2O$ and 30% $O_2$. Their rectal temperature was maintained at 37° C.±0.5° C. on a heating pad. The animals were randomly divided into three groups, given SHED-derived conditioned medium (SH-CM) intranasally (n=1, day 16 sacrificed=1) (group I) or phosphate-buffered saline (PBS) intranasally (n=1, day 16 sacrificed=1) (group II) or pMCAO operation only (n=5, day 16 sacrificed=5) (group III). SH-CM, which had been prepared in the same manner as in Example 1, was used in this experiment. The rats were laid on their backs, their neck were elevated by rolled-up 4 cm×4 cm gauze, and a total of 100 µl per rat was administered in the olfactory pathway using a Hamilton microsyringe, 10 µl at a time, alternating the nostrils, with an interval of 2 min between each administration. During these procedures, the mouth and the opposite nostril were shut. Intranasal administration was performed everyday during a period from day 3 to day 15.

Evaluation of Motor Disability

A blind test on the rats was carried out on days 1, 3, 6, 9, 12 and 15 using a standardized motor disability scale with slight modifications. The rat was given 1 point for each of the following parameters: flexion of the forelimb contralateral to the stroke when instantly hung by the tail; extension of the contralateral hindlimb when pulled from the table; and rotation to the paretic side against resistance. In addition, 1 point was given for circling motion to the paretic side when trying to walk, 1 point was given for failure to walk out of a circle of 50 cm in diameter within 10 seconds, 2 points were given for failure to leave the circle within 20 seconds, and 3 points were scored for inability to exit the circle within 60 seconds. In addition, 1 point each was given for inability of the rat to extend the paretic forepaw when pushed against the table from above, laterally, or sideways. The evaluation according to the motor disability scale was performed 3 times per animal time-point.

Assessment of Infarct Volume

The cryosections obtained from samples on day 16 were stained with Hematoxylin and Eosin. Image J (National Institutes of Health, ML) was used to determine each infarct area in 20 coronal sections (20 mm-thick) at 1.00-mm intervals. The entire infarct area was covered by these 12 coronal sections. Regional infarct volumes were calculated by summing the infarct areas and multiplying these areas by the distance between sections (1.00 mm), followed by remediation for brain edema.

Results

Evaluation of Motor Function

Figure 27:
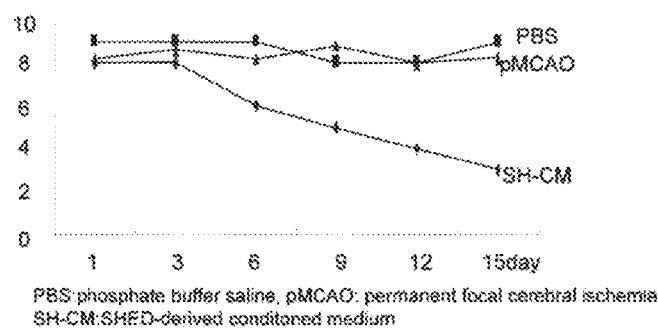
FIG. 27 is a graph showing changes in disability score after starting the nasal administration to Group I, Group II and Group III in Example 5 of the invention.

All groups (group I, group II and group III) displayed high scores for motor function at the early-stage (the scores on day 1 were 8, 9 and 8.2±0.45, respectively, and the scores on day 3 were 8, 9 and 8.6±0.89, respectively). 6 days later, progressive alleviation in motor disability in the group I on day 6 became significant as compared with groups II and III (6, 9 and 8.2±0.84, respectively), and more significant on day 9 as compared with the groups II and III (5, 8 and 8.8±1.0, respectively) (FIG. 27). Persistent improvement in the group I was noted on day 12 (4) and day 15 (3), while persistent impairment due to motor disability (scores above 8) was observed in the groups II and III on day 15 (9 and 8.25±0.96, respectively).

Reduction of Infarct Volume

Figure 28:
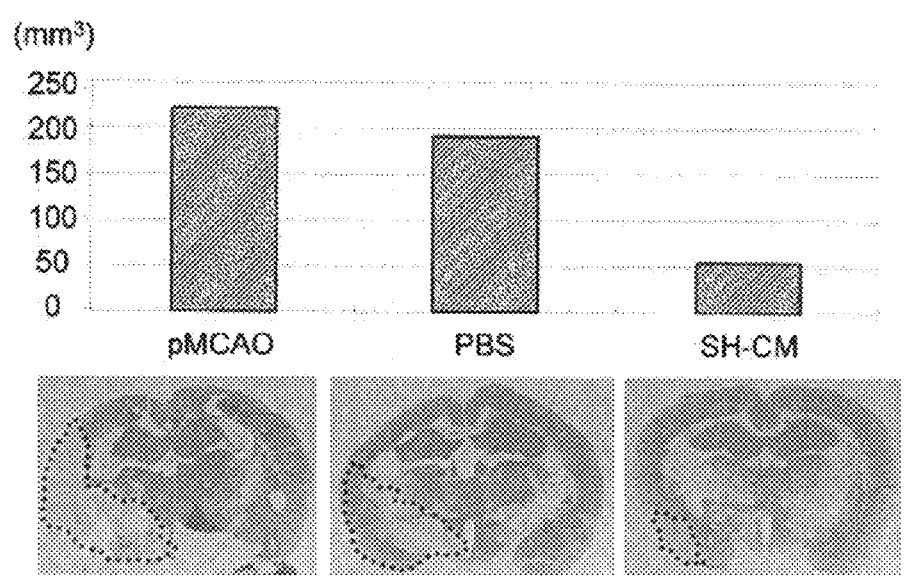
FIG. 28 is a graph showing the infarct volumes on day 16 after starting the nasal administration to Group I, Group II and Group III in Example 5 of the invention.

There was a significant decrease in the infarct volume on day 16 in the group I (day 16, 54.3 mm$^3$, n=1), as compared to the groups II and III (day 16, 192.7 mm$^3$, n=1; day 16, 222.7 mm$^3$, n=1) (FIG. 28). These results suggest that the intranasal administration of SH-CM promoted regeneration.

As described above, it was found that cytokine therapy has an excellent restorative effect toward cerebral infarct areas, and is useful for treatment of cerebral infarction. Similar results were also confirmed in other rats.

It was also found that selection of intranasal administration for cytokine therapy provides less invasiveness, and exerts a direct effect on ischemic regions after passing the blood-brain barrier. Further, since the deciduous teeth stem cell-conditioned medium is considered to contain various nutritional factors, more rapid restoration as compared with single administration of a nutritional factor is expected.

Example 6

1. Preparation of Conditioned Medium from Dental Pulp Stem Cells

Figure 29:
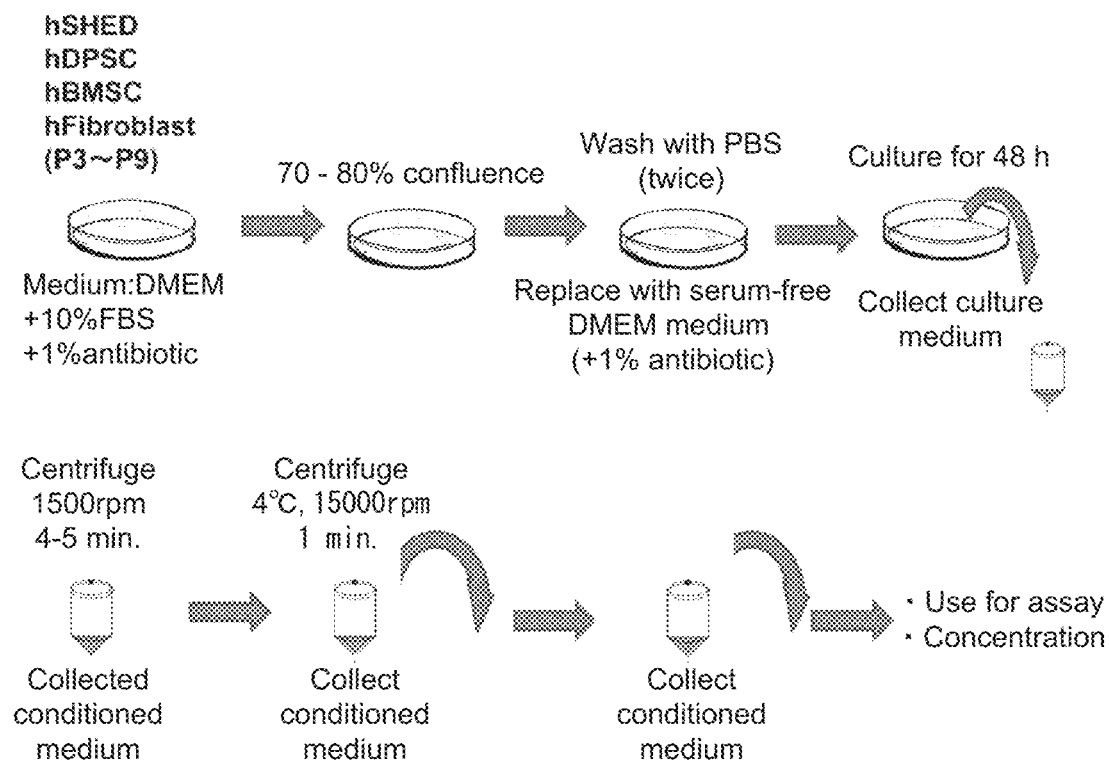
FIG. 29 is a conceptual diagram explaining a preparation method of the conditioned medium. hSHED: stem cell from human exfoliated deciduous teeth. hDPSC: permanent teeth dental pulp stem cell. hBMSC: human bone marrow mesenchymal stem cell. hFibroblast: human fibroblast.

Conditioned media from dental pulp stem cells (SHED and DPSCs) were prepared according to the following procedure (see, FIG. 29), and were used in an experiment for verifying the nerve regeneration effect.

(i) Culture dental pulp stem cells in a serum (10% FBS)-containing medium at 37° C. with 5% $CO_2$ until the cells in the culture dish reaches 70% to 80% confluence.

(ii) When reach 70% to 80% confluence, wash the culture dish twice with PBS, and replace the medium with a serum-free (0% FBS) medium.

(iii) Culture at 37° C. with 5% $CO_2$ for 48 hours.

(iv) After the 48 hours culture, collect the serum-free medium into a centrifugation tube.

(v) Centrifuge the collected serum-free medium at 1,500 rpm for 4 to 5 minutes to precipitate impurities such as dead cells.

(vi) Transfer the supernatant from the centrifuged centrifugation tube into another centrifugation tube while paying attention not to suction impurities.

(vii) Further centrifuge the collected supernatant at 4° C. and 15,000 rpm for 1 minute to precipitate impurities again.

(viii) Transfer the supernatant from the centrifuged centrifugation tube into another centrifugation tube again while paying attention not to suction impurities (ix) obtain the resultant supernatant, which serves as dental pulp stem cell-conditioned medium.

2. Neural Cells Used for In Vitro Analysis

PC12 cells, a cell line derived from an immortalized rat adrenal pheochromocytoma, were used as neural cells. It is known that the addition of nerve growth factor (NGF), one of neurotrophic factors, to PC 12 cells induces the outgrowth of axon-like processes and differentiation into neuron-like cells. Thus, PC12 cells are used as model cells for various in vitro experiments on nervous system.

3. Neurite Outgrowth Effect and Apoptosis Inhibitory of Dental Pulp Stem Cell-Conditioned Medium (Neurite outgrowth experiment and apoptosis induction experiment using nerve regeneration inhibitory substances)

The neurite outgrowth effect and apoptosis inhibitory effect of the dental pulp stem cell-conditioned medium were examined in the presence or absence of a nerve regeneration inhibitory substance (neurite outgrowth inhibitory factor). CSPG and MAG were used as nerve regeneration inhibitory substances. The protocol of the experiment is as described below.

(1) Neurite Outgrowth Experiment (i) Coat a nerve regeneration inhibitory substance (CSPG or MAG) on a (poly-L-lysine coated) cell culture well at 37° C. for 24 hours.

(ii) Seed PC12 cells in the plates coated with the nerve regeneration inhibitory substance, and culturing them with the dental pulp stem cell-conditioned medium for 24 hours. As comparative groups, a serum-free medium, a fibroblast-conditioned medium and a bone marrow mesenchymal stem cell-conditioned medium are used.

(iii) Evaluate the neurite outgrowth of the PC 12 cells based on a phase-contrast micrograph thereof.

(2) Apoptosis Induction Experiment

P12 cells are seeded in the plates coated with the nerve regeneration inhibitory substance, and are cultured with the dental pulp stem cell-conditioned medium for 24 hours. The apoptosis of the cells is evaluated according to the TUNEL assay. A serum-free medium, a fibroblast-conditioned medium and a bone marrow mesenchymal stem cell-conditioned medium are used as comparative groups.

In the plates coated with nerve regeneration inhibitory substance (CSPG, MAG), the dental pulp stem cell-conditioned medium exhibited a stronger neurite outgrowth effect (FIGS. 30 to 33) and apoptosis inhibitory effect (FIGS. 34 and 35) as compared to other groups (comparative groups). The dental pulp stem cell-conditioned medium exhibited a strong neurite outgrowth effect even without the addition of NGF, which is essential for PC12 cells to differentiate into neuron-like cells (i.e., the dental pulp stem cell-conditioned medium exhibited a strong neurite outgrowth effect by itself).

Figure 30:
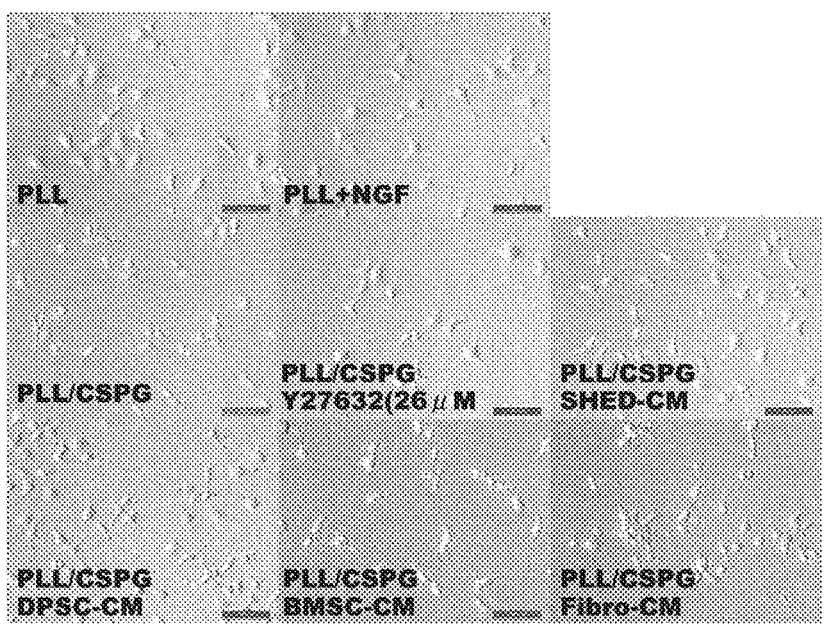
FIG. 30 is a photograph showing the results of a neurite outgrowth experiment (phase-contrast microscopic image).

That is, as shown in FIG. 30, culturing PC12 neuron-like cells with the dental pulp stem cell-conditioned medium (for 24 hours) results in outgrowth of neurites (i.e., the dental pulp stem cell-conditioned medium exhibits neurite outgrowth activity), even in the dish coated with a nerve regeneration inhibitory substance CSPG (see FIG. 30). Addition of the bone marrow mesenchymal stem cell-conditioned medium or the skin-derived fibroblast-conditioned medium alone, or addition of Y27632 alone, which inhibits ROCK activation, does not exhibit such outgrowth activity.

Figure 31:
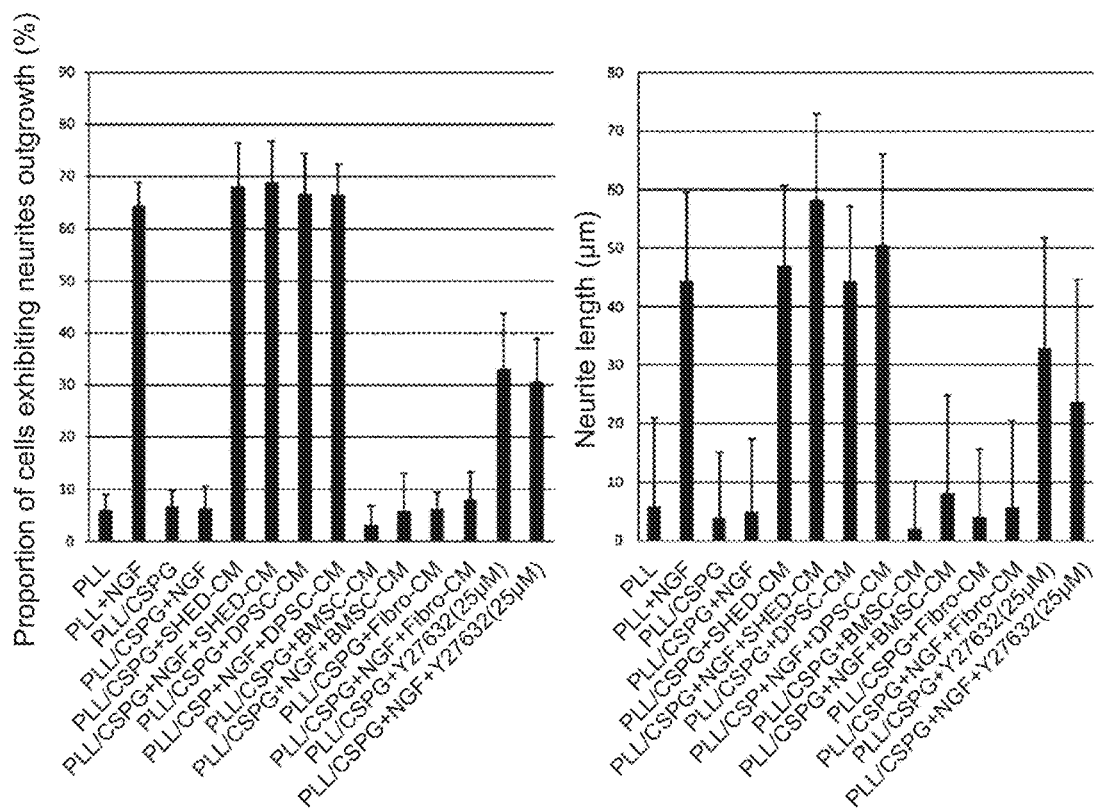
FIG. 31 shows the results of a neurite outgrowth experiment. The graph shows the proportion of cells of which neurites were observed (left) and neurite length (right).

As shown in FIG. 31, the dental pulp stem cell-conditioned medium increases the proportion of cells exhibiting neurite outgrowth, and promotes the formation of longer neurites, even under conditions in which a nerve regeneration inhibitory substance CSPG is present.

Figure 32:
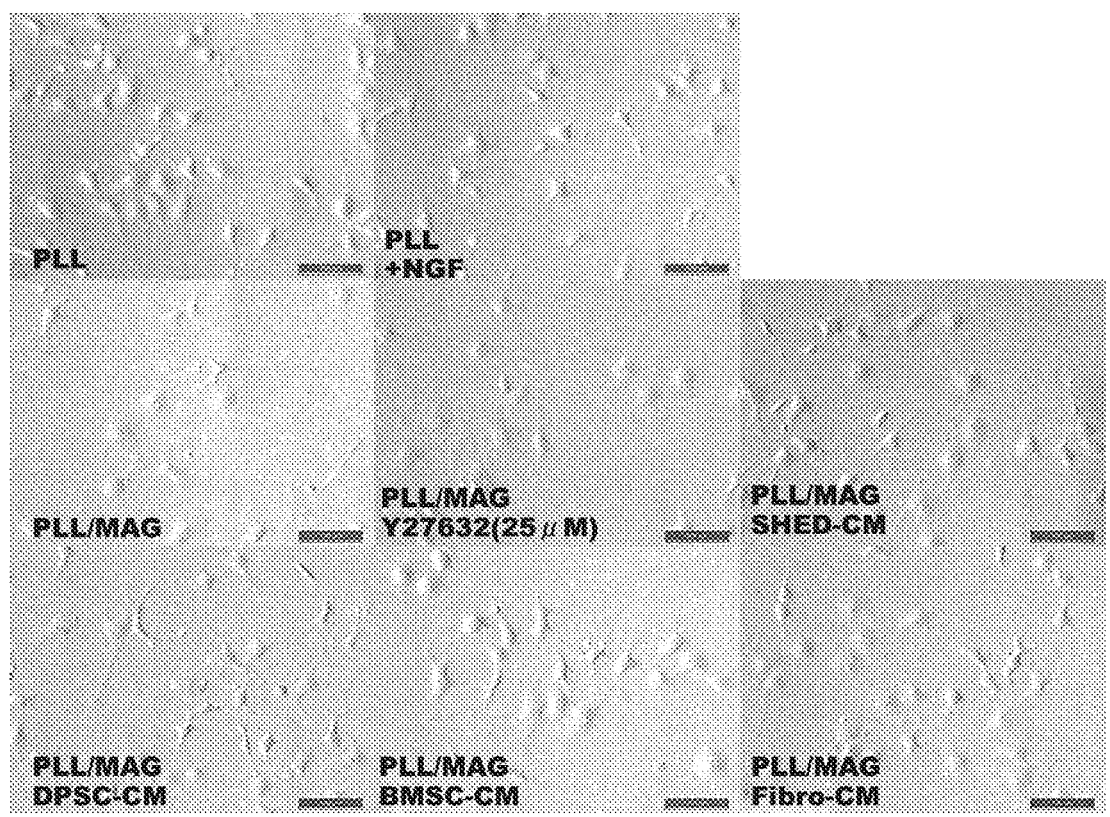
FIG. 32 is a photograph showing the results of a neurite outgrowth experiment (phase-contrast microscopic image).

As shown in FIG. 32, culturing PC12 neuron-like cells with the dental pulp stem cell-conditioned medium (for 24 hours) results in outgrowth of neurites (i.e., the dental pulp stem cell-conditioned medium exhibits neurite outgrowth activity), even in the dish coated with a nerve regeneration inhibitory substance MAG. Addition of the bone marrow mesenchymal stem cell-conditioned medium or the dermal fibroblast-conditioned medium alone, or addition of Y27632 alone, which inhibits ROCK activation, does not exhibit such outgrowth activity.

Figure 33:
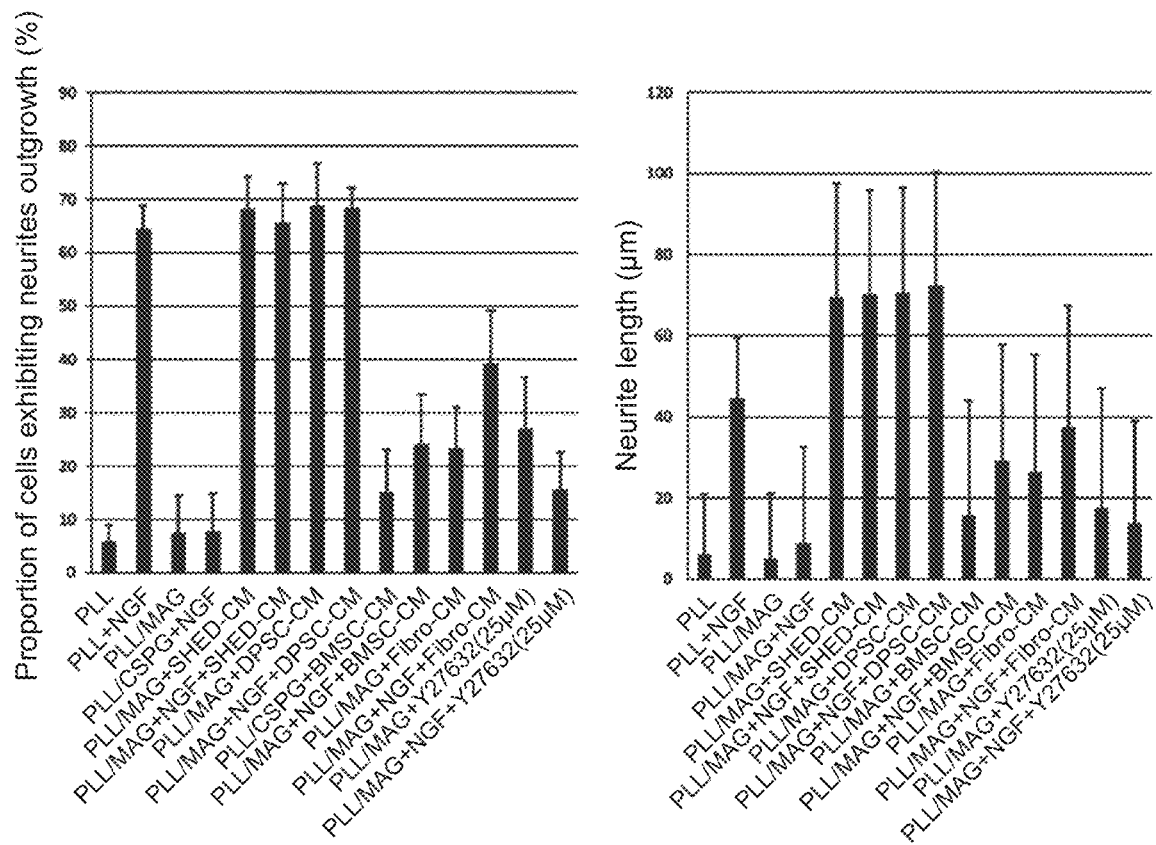
FIG. 33 shows the result of a neurite outgrowth experiment. The graph shows the proportion of cells of which neurites were observed (left) and neurite length (right).

As shown in FIG. 33, the dental pulp stem cell-conditioned medium increases the proportion of cells exhibiting neurite outgrowth, and promotes the formation of longer neurites, even under conditions in which a nerve regeneration inhibitory substance MAG is present.

Figure 34:
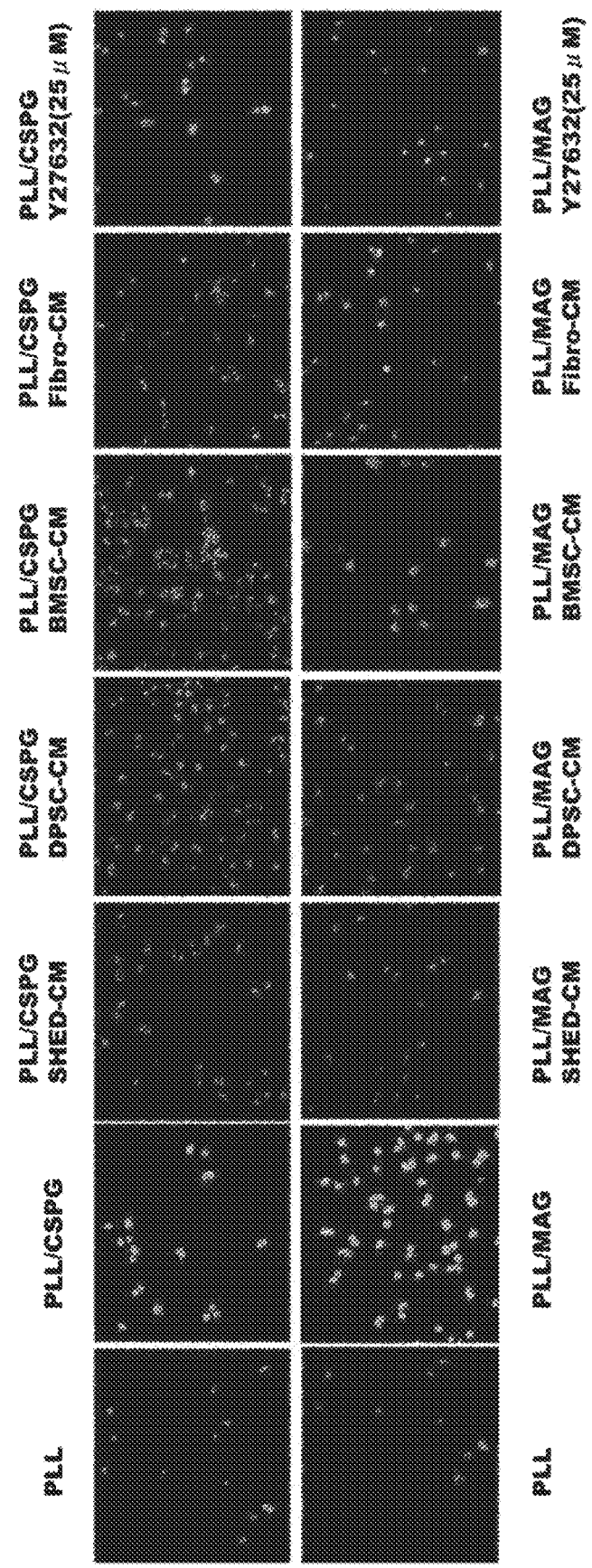
FIG. 34 is a photograph showing the results of an apoptosis inhibition experiment (TUNEL assay).
Figure 35:
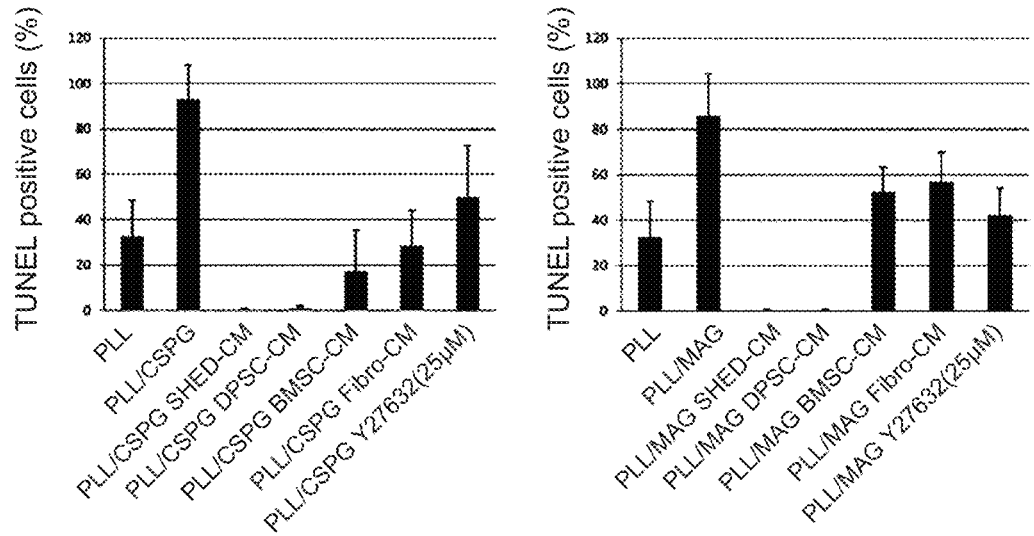
FIG. 35 shows the result of an apoptosis inhibition experiment (TUNEL assay). The graph shows statistically-processed apoptosis inhibiting effects of the conditioned medium from dental pulp stem cells. The left graph is a graph in which apoptosis inhibiting effects in the presence of CSPG are checked, and the right graph is a graph in which apoptosis inhibiting effects in the presence of MAG are checked.

As shown in FIGS. 34 and 35, almost all of the PC12 neuron-like cells cultured for 24 hours in the dish coated with a nerve regeneration inhibitory substance MAG or CSPG underwent apoptosis. The dental pulp stem cell-conditioned medium almost perfectly inhibits the apoptosis thereof.

The symbols in FIG. 30 represent the following: PLL: poly-L-lysine coat, PLL+NGF: poly-L-lysine coat and addition of nerve growth factor (NGF), PLL/CSPG: poly-L-lysine coat and CSPG coat, PLL/CSPG Y27632: poly-L-lysine coat, CSPG coat and addition of Y27632, PLL/CSPG SHED-CM: poly-L-lysine coat, CSPG coat and culturing with SHED-conditioned medium, PLL/CSPG DPSC-CM: poly-L-lysine coat, CSPG coat and culturing with DPSC-conditioned medium, PLL/CSPG BMSC-CM: poly-L-lysine coat, CSPG coat and culturing with bone marrow mesenchymal stem cell-conditioned medium, PLL/CSPG Fibro-CM: poly-L-lysine coat, CSPG coat and culturing with fibroblast-conditioned medium.

The symbols in FIG. 31 represent the following: PLL: poly-L-lysine coat, PLL+NGF: poly-L-lysine coat and addition of nerve growth factor (NGF), PLL/CSPG: poly-L-lysine coat and CSPG coat, PLL/CSPG+NGF: poly-L-lysine coat, CSPG coat and addition of NGF, PLL/CSPG+SHED-CM: poly-L-lysine coat, CSPG coat and culturing with SHED-conditioned medium, PLL/CSPG+NGF+SHED-CM: poly-L-lysine coat, CSPG coat, addition of NGF and culturing with SHED-conditioned medium, PLL/CSPG+DPSC-CM: poly-L-lysine coat, CSPG coat and culturing with DPSC-conditioned medium, PLL/CSPG+NGF+DPSC-CM: poly-L-lysine coat, CSPG coat, addition of NGF and culturing with DPSC-conditioned medium, PLL/CSPG+BMSC-CM: poly-L-lysine coat, CSPG coat and culturing with bone marrow mesenchymal stem cell-conditioned medium, PLL/CSPG+NGF+BMSC-CM: poly-L-lysine coat, CSPG coat, addition of NGF and culturing with bone marrow mesenchymal stem cell-conditioned medium, PLL/CSPG+Fibro-CM: poly-L-lysine coat, CSPG coat and culturing with fibroblast-conditioned medium, PLL/CSPG+NGF+Fibro-CM: poly-L-lysine coat, CSPG coat, addition of NGF and culturing with fibroblast-conditioned medium, PLL/CSPG+Y27632: poly-L-lysine coat, CSPG coat and addition of Y27632, PLL/CSPG+NGF+Y27632: poly-L-lysine coat, CSPG coat, addition of NGF and addition of Y27632.

The symbols in FIG. 32 represent the following: PLL: poly-L-lysine coat, PLL+NGF: poly-L-lysine coat and addition of nerve growth factor (NGF), PLL/MAG: poly-L-lysine coat and MAG coat, PLL/MAG Y27632: poly-L-lysine coat, MAG coat and addition of Y27632, PLL/MAG SHED-CM: poly-L-lysine coat, MAG coat and culturing with SHED-conditioned medium, PLL/MAG DPSC-CM: poly-L-lysine coat, MAG coat and culturing with DPSC-conditioned medium, PLL/MAG BMSC-CM: poly-L-lysine coat, MAG coat and culturing with bone marrow mesenchymal stem cell-conditioned medium, PLL/MAG Fibro-CM: poly-L-lysine coat, MAG coat and culturing with fibroblast-conditioned medium.

The symbols in FIG. 33 represent the following: PLL: poly-L-lysine coat, PLL+NGF: poly-L-lysine coat and addition of nerve growth factor (NGF), PLL/MAG: poly-L-lysine coat and MAG coat, PLL/MAG+NGF: poly-L-lysine coat, MAG coat and addition of NGF, PLL/MAG+SHED-CM: poly-L-lysine coat, MAG coat and culturing with SHED-conditioned medium, PLL/MAG+NGF+SHED-CM: poly-L-lysine coat, MAG coat, addition of NGF and culturing with SHED-conditioned medium, PLL/MAG+DPSC-CM: poly-L-lysine coat, MAG coat and culturing with DPSC-conditioned medium, PLL/MAG+NGF+DPSC-CM: poly-L-lysine coat, MAG coat, addition of NGF and culturing with DPSC-conditioned medium, PLL/MAG+BMSC-CM: poly-L-lysine coat, MAG coat and culturing with bone marrow mesenchymal stem cell-conditioned medium, PLL/MAG+NGF+BMSC-CM: poly-L-lysine coat, MAG coat, addition of NGF and culturing with bone marrow mesenchymal stem cell-conditioned medium, PLL/MAG+Fibro-CM: poly-L-lysine coat, MAG coat and culturing with fibroblast-conditioned medium, PLL/MAG+NGF+Fibro-CM: poly-L-lysine coat, MAG coat, addition of NGF and culturing with fibroblast-conditioned medium, PLL/MAG+Y27632: poly-L-lysine coat, MAG coat and addition of Y27632, PLL/MAG+NGF+Y27632: poly-L-lysine coat, MAG coat, addition of NGF and addition of Y27632.

The symbols in FIG. 34 represent the following: PLL: poly-L-lysine coat, PLL/CSPG: poly-L-lysine coat and CSPG coat, PLL/CSPG SHED-CM: poly-L-lysine coat, CSPG coat and culturing with SHED-conditioned medium, PLL/CSPG DPSC-CM: poly-L-lysine coat, CSPG coat and culturing with DPSC-conditioned medium, PLL/CSPG BMSC-CM: poly-L-lysine coat, CSPG coat and culturing with bone marrow mesenchymal stem cell-conditioned medium, PLL/CSPG Fibro-CM: poly-L-lysine coat, CSPG coat and culturing with fibroblast-conditioned medium, PLL/CSPG+Y27632: poly-L-lysine coat, CSPG coat and addition of Y27632, PLL: poly-L-lysine coat, PLL/MAG: poly-L-lysine coat and MAG coat, PLL/MAG SHED-CM: poly-L-lysine coat, MAG coat and culturing with SHED-conditioned medium, PLL/MAG DPSC-CM: poly-L-lysine coat, MAG coat and culturing with DPSC-conditioned medium, PLL/MAG BMSC-CM: poly-L-lysine coat, MAG coat and culturing with bone marrow mesenchymal stem cell-conditioned medium, PLL/MAG Fibro-CM: poly-L-lysine coat, MAG coat and culturing with fibroblast-conditioned medium, PLL/MAG Y27632: poly-L-lysine coat, MAG coat and addition of Y27632.

The symbols in FIG. 35 represent the following: PLL: poly-L-lysine coat, PLL/CSPG: poly-L-lysine coat and CSPG coat, PLL/CSPG SHED-CM: poly-L-lysine coat, CSPG coat and culturing with SHED-conditioned medium, PLL/CSPG DPSC-CM: poly-L-lysine coat, CSPG coat and culturing with DPSC-conditioned medium, PLL/CSPG BMSC-CM: poly-L-lysine coat, CSPG coat and culturing with bone marrow mesenchymal stem cell-conditioned medium, PLL/CSPG Fibro-CM: poly-L-lysine coat, CSPG coat and culturing with fibroblast-conditioned medium, PLL/CSPG+Y27632: poly-L-lysine coat, CSPG coat and addition of Y27632, PLL: poly-L-lysine coat, PLL/MAG: poly-L-lysine coat and MAG coat, PLL/MAG SHED-CM: poly-L-lysine coat, MAG coat and culturing with SHED-conditioned medium, PLL/MAG DPSC-CM: poly-L-lysine coat, MAG coat and culturing with DPSC-conditioned medium, PLL/MAG BMSC-CM: poly-L-lysine coat, MAG coat and culturing with bone marrow mesenchymal stem cell-conditioned medium, PLL/MAG Fibro-CM: poly-L-lysine coat, MAG coat and culturing with fibroblast-conditioned medium, PLL/MAG Y27632: poly-L-lysine coat, MAG coat and addition of Y27632.

As described above, a surprising fact that the dental pulp stem cell-conditioned medium suppresses the action of nerve regeneration inhibitory substances, promotes neurite outgrowth, and suppresses apoptosis, was revealed. In other words, it was revealed that the dental pulp stem cell-conditioned medium is quite effective for CNS regeneration and the treatment of CNS diseases.

4. Verification Using Spinal Cord-Injured Model Animal (1) Improvement of Motor Function of Hindlimbs by Administration of Conditioned Medium 10th thoracic vertebrae were removed from 8-week-old female SD rats under general anesthesia with pentobarbital sodium, and crush injury damage was induced by applying a 200 kilodyn force from outside the dura mater using an IH impactor, to obtain a model of spinal cord crush injury. From immediately after the crush injury, a silicone tube connected to a perfectly implantable microinfusion pump in which a dental pulp stem cell-conditioned medium (SHED-CM), a bone marrow mesenchymal stem cell-conditioned medium (BMSC-CM) or PBS (control) was charged, was inserted from the subarachnoid cavity below the 12th thoracic vertebra, and placed so as to allow outflow from directly above the injury site. The administration was continuously carried out at a flow rate of 24 μl/day for 8 weeks until the rats were sacrificed, and the motor function of hindlimbs was evaluated every week. The Basso-Beattie-Bresnahan (BBB) score (Basso D M, Beattie M S, Bresnahan J C. A sensitive and reliable locomotor rating scale for open field testing in rats. J. Neurotrauma., 1995: 12: 1-21.) was used for the evaluation.

<Bbb Score>

0. No observable movement of the hip joint, knee joint and foot joint at all.
1. Slight movement of one or two of the joints.
2. Extensive movement of one joint only.
3. Extensive movement of two joints only.
4. Slight movement of all of the three joints.
5. Slight movement of two joints and extensive movement of the remaining one joint.
6. Extensive movement of two joints and slight movement of the remaining one joint.
7. Extensive movement of all of the three joints.
8. Sweeping with no weight support, or plantar placement of the paw with no weight support.
9. Very occasional sweeping or stepping with weight support by the hindlimbs.
10. Occasional (5% to 50%) weight supported steps and no forelimb-hindlimb coordination.
11. Frequent (50% to 100%) weight supported steps and no forelimb-hindlimb coordination.
12. Occasional (5% to 50%) weight supported steps and occasional (5% to 50%) forelimb-hindlimb coordination.
13. Frequent (50% to 100%) weight supported steps and frequent (50% to 100%) forelimb-hindlimb coordination.
14. Frequent plantar weight supported steps with forelimb-hindlimb coordination/consistent plantar weight supported steps with external rotation of paw position (due to weak muscle strength).
15. Forelimb-hindlimb coordination, occasional (5% to 50%) steps with heel lifting, and external rotatation of paw position.
16. Forelimb-hindlimb coordination, frequent (50% to 100%) steps with heel lifting, and occasional parallel positioning of paw to the body.
17. Forelimb-hindlimb coordination, frequent (50% to 100%) steps with heel lifting, and parallel positioning of paw to the body.
18. Forelimb-hindlimb coordination, steps with heel lifting, and parallel positioning of paw to the body.
19. Forelimb-hindlimb coordination, steps with heel lifting, parallel positioning of paw to the body, the tail remains down.
20. Forelimb-hindlimb coordination, steps with heel lifting, parallel positioning of paw to the body, and lifting the tail.
21. Forelimb-hindlimb coordination, steps with heel lifting, parallel positioning of paw to the body, lifting of the tail, and weight support.

Figure 36:
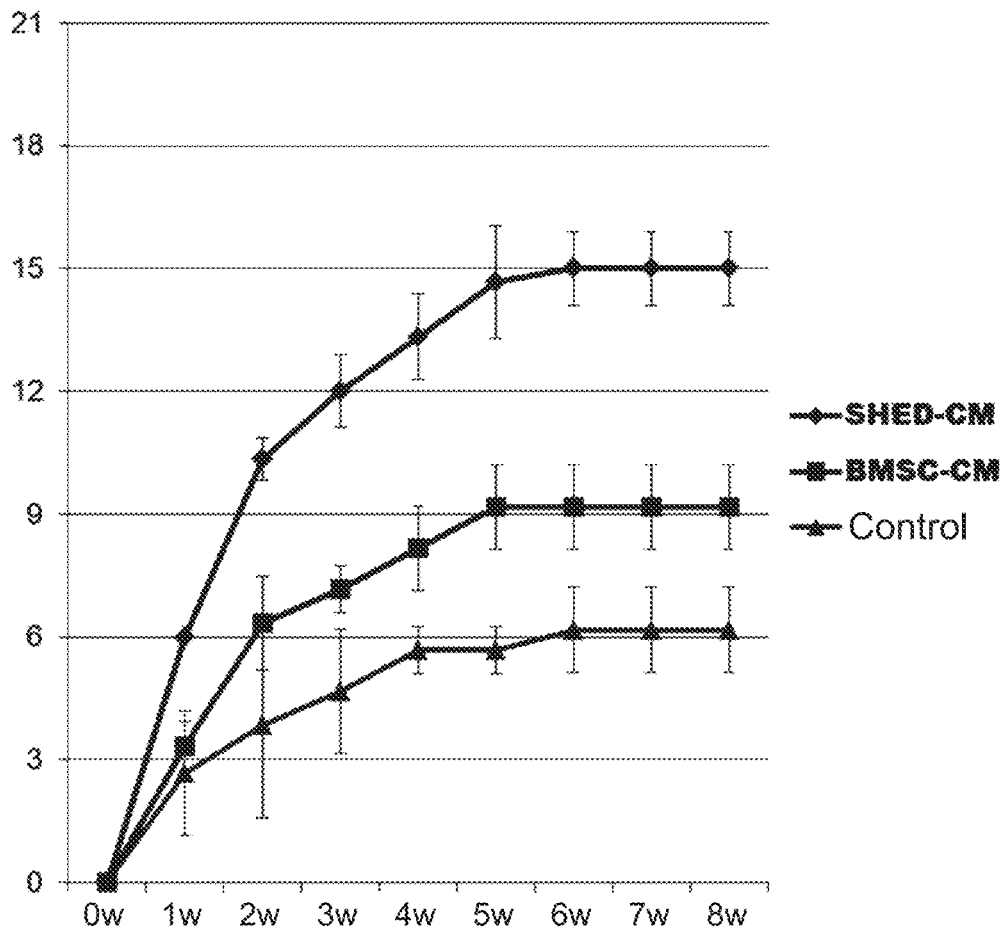
FIG. 36 is a graph showing the results of an experiment using an animal model of spinal cord crush injury. SHED-CM: dental pulp stem cell-conditioned medium administered group. BMSC-CM: bone marrow mesenchymal stem cell-conditioned medium administered group. Control: PBS administered group.

The ameliorating effects of the hindlimb motor function was compared based on the BBB scores. The evaluation results are shown in FIG. 36. The group administered with the dental pulp stem cell-conditioned medium (SHED-CM) exhibited surprising improvement and recovery of the hindlimb motor function as represented by score 15 (forelimb-hindlimb coordination, occasional (5% to 50%) steps with heel lifting, and external rotation of paw position). Although the group administered with the bone marrow mesenchymal stem cell-conditioned medium (BMSC-CM)

also exhibited a certain degree of improvement, the improvement effect thereof is far lower than that of the SHED-CM group.

(2) Alteration of Spinal Cord Morphology after 8 Weeks 8 weeks after the initiation of the administration of SHEM-CM (or BMSC-CM or PBS), the rats were perfusion fixed with paraformaldehyde. Subsequently, a length of the spinal cord including the injury site and extending 5 mm rostrally and 5 mm caudally from the injury site was dissected, and taken out. The weights of the spinal cords were compared between the Sham group, the control group, the BMSC-CM group and the SHED-CM group.

The morphological alteration of the spinal cord 8 weeks after the initiation of the administratioin was assessed. The states of the spinal cords taken out are shown in the upper panel of FIG. 37. The comparison of the weights (masses) of the spinal cords is shown in the lower panel of FIG. 37. In the SHED-CM treated group, the atrophy of the spinal cord caudal to the injury site (injury epicenter) was suppressed (the upper panel of FIG. 37). In other words, the morphological alteration of the injured spinal cord was suppressed by the administration of SHED-CM. In accordance with this result, the SHEM-CM group also exhibited an increase in the weight of the spinal cord (the lower panel of FIG. 37).

(3) Spinal Neuroaxis after 8 Weeks 8 weeks after the initiation of the administration of SHEM-CM (or PBS), the rats were perfusion fixed with paraformaldehyde. A length of the spinal cord including the injury site and extending 5 mm rostrally and 5 mm caudally from the injury site was dissected, and taken out. Then, the spinal cord was embedded and frozen in O.C.T compound, and frozen section slides of the spinal cord were prepared. The frozen section slides of the spinal cord were immunostained with an anti-serotonin (5-HT) antibody and with an antibody against neuroaxis (anti-Neurofilament-M (NF-M) antibody).

Figure 38:
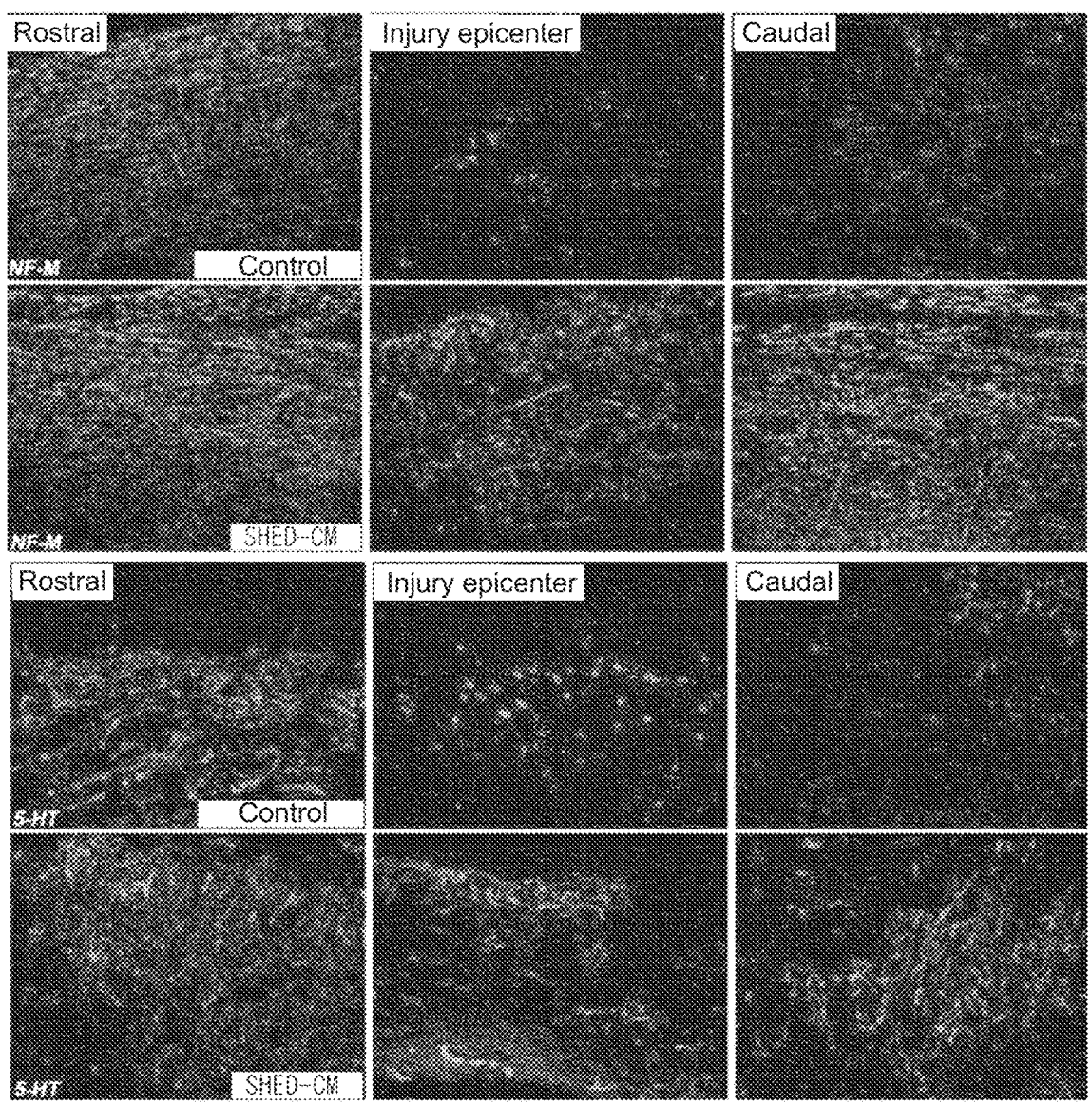
FIG. 38 shows the results of an experiment using an animal model of spinal cord crush injury. SHED-CM: dental pulp stem cell-conditioned medium administered group. Control: PBS administered group.

The damaged portion and a neighbourhood thereof were histologically examined 8 weeks after the initiation of the administration. The results of the immunostaining are shown in FIG. 38. Continuous administration of a small amount of SHED-CM maintained the number of the total neurofilaments (NF-M) in the region caudal to the injury site. The number of serotonin fibers projecting from the raphe nuclei of the brain stem to the spinal cord was also maintained. It was revealed that the loss of neurofilaments is suppressed by the administration of SHED-CM, and that a neurotransmitter serotonin produced in the upper areas and the brain stem was transported to the areas lower than the injury site.

(4) Experiment on Apoptosis Suppression by Conditioned Medium

The control group and the SHED-CM group were perfusion fixed with paraformaldehyde 24 hours after the spinal cord crush injury and one week after the spinal cord crush injury. A length of the spinal cord including the injury site and extending 5 mm rostrally and 5 mm caudally from the injury site was dissected, and taken out. Then, the spinal cord taken out was embedded and frozen in O.C.T compound, and frozen section slides of the spical cord were prepared. The frozen section slides of the spical cord were double-immunostained with TUNEL, which specifically reacts with fragmentalized DNAs, and an anti-GFAP antibody specific for astrocytes, an anti-NeuN antibody specific for neuronal cells or an anti-CNPase antibody specific for oligodendrocytes, to compare the cell death of neuronal cells and glia cells.

Figure 39:
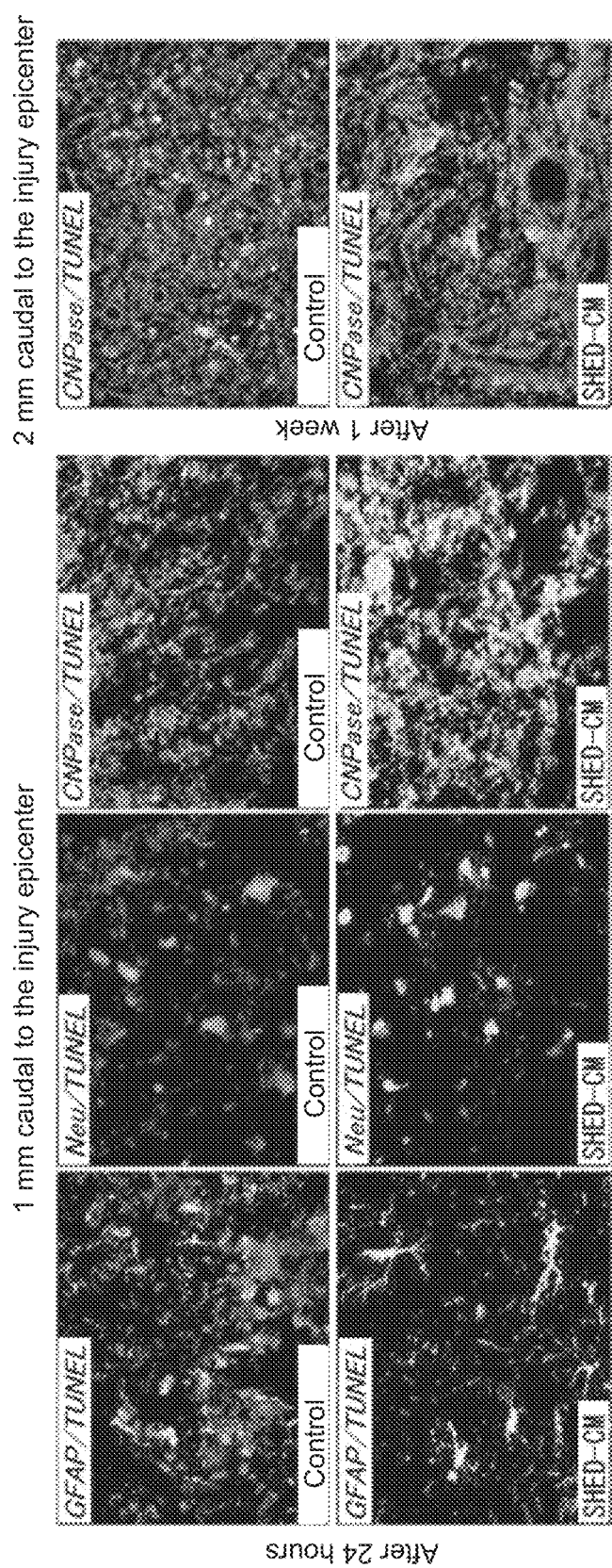
FIG. 39 shows the results of an experiment using an animal model of spinal cord crush injury. SHED-CM: dental pulp stem cell-conditioned medium administered group. Control: PBS administered group.

The cell death of the neuronal cells in the damaged portion and in the neighbourhood thereof was evaluated 24 hours after the spinal cord crush injury and one week after the spinal cord crush injury. The results are shown in FIG. 39. Continuous administration of a small amount of SHED-CM suppressed apoptotic cell death of astrocytes, neurons and oligodendrocytes that occured immediately after the nerve injury. In spinal cord injury, apoptotic cell death of oligodendrocytes are observed in a larger area one week after the injury (enlargement of secondary damage). It was revealed that SHED-CM also suppresses this apoptotic cell death, thereby suppressing the enlargement of neural damage.

From the above, spinal cord injury, neurodegenerative diseases such as amyotrophic lateral sclerosis, Alzheimer's disease, Parkinson's disease, progressive supranuclear palsy, Huntington's disease, multiple system atrophy and spinocerebellar ataxia, degeneration or loss of neuronal cells caused by cerebral ischemia, intracerebral hemorrhage or cerebral infarction and a retinal disease involving a neuronal cell disorder are contemplated as diseases to which the CNS disease treatment composition according to the invention can be applied.

Therefore, according to the invention, since a stem cell-conditioned medium that is obtained by culturing stem cells and that contains a mixture of cytokines is used, endogenous stem cells in the target tissue is allowed to differentiate and proliferate. As a result, the target tissue is repaired and regenerated through the proliferation of cells in the damaged part, the generation of extracellular matrix, etc.

The invention is by no means limited to the embodiments and examples of the invention described above. Various modifications are also included in the invention as long as they are within the scope of the claims, and can easily be conceived therefrom by those skilled in the art.

U.S. Provisional Application No. 61/317,713, filed Mar. 26, 2010, U.S. Provisional Application No. 61/410,370, filed Nov. 5, 2010, Japanese Patent Application No. 2010-267962, filed Dec. 1, 2010, U.S. Provisional Application No. 61/437,697, filed Jan. 31, 2011 and Japanese Patent Application No. 2011-037028, filed Feb. 23, 2011, are incorporated by reference herein in their entirety.

All publications, patent applications, and technical standards mentioned in this specification are herein incorporated by reference to the same extent as if each individual publication, patent application, or technical standard was specifically and individually indicated to be incorporated by reference.

The invention claimed is:

1. A method of repairing a damaged target tissue in a patient in need thereof, comprising administering an effective amount of a dental pulp stem cell-conditioned medium to the patient,
   wherein the target tissue is brain, skin, periodontal tissue, bone, or spinal cord,
   wherein the dental pulp stem cell-conditioned medium does not comprise stem cells, and
   wherein the dental pulp stem cell-conditioned medium has been prepared by a process including the following steps (1) to (3):
   (1) a step of selecting adhesive cells from dental pulp cells;
   (2) a step of culturing the adhesive cells; and
   (3) a step of collecting a conditioned medium of the adhesive cells.

2. The method according to claim 1, wherein the repair of the damaged target tissue is achieved based on an ability of endogenous stem cells.

3. The method according to claim 1, wherein the dental pulp stem cell-conditioned medium is administered by an administration method selected from the group consisting of intravenous administration, intraarterial administration, intraportal administration, intradermal administration, subcutaneous administration, intramuscular administration, intraperitoneal administration and intranasal administration.

4. The method according to claim 1, wherein the patient is a cerebral infarction patient, and the repairing of a damaged target tissue includes repairing a damaged tissue in the brain.

5. The method according to claim 1, wherein the dental pulp stem cell-conditioned medium is administered by intranasal administration.

6. The method according to claim 1, wherein the patient is a central nervous system (CNS) disease patient, and the repairing of a damaged target tissue includes treating a CNS disease.

7. The method according to claim 1, wherein the dental pulp stem cell is an undifferentiated dental pulp stem cell that has not been subjected to differentiation-inducing treatment after acquisition thereof, or a differentiation-induced dental pulp stem cell that has been induced to differentiate into a neural cell after acquisition thereof.

8. The method according to claim 6, wherein a pluripotent stem cell that has been induced to differentiate into a neural cell is administered to the CNS disease patient after the administration of the dental pulp stem cell-conditioned medium.

9. The method according to claim 1, wherein the repairing of a damaged target tissue comprises treatment of damage to skin, periodontal tissue or bone, treatment of cerebral infarction, or treatment of a CNS disease.

10. The method according to claim 6, wherein the CNS disease is a disease or disorder selected from the group consisting of a spinal cord injury, a neurodegenerative disorder, degeneration or loss of neuronal cells and a retinal disease involving a neuronal cell disorder.

11. The method according to claim 1, wherein the dental pulp stem cell-conditioned medium has been prepared by a process including the following steps (1) to (4):

(1) a step of selecting adhesive cells from dental pulp cells;
(2) a step of culturing the adhesive cells to 70% to 80% confluence;
(3) a step of culturing the cells obtained in step (2) in serum-free liquid; and
(4) a step of collecting a conditioned medium of the cells obtained in step (3).

12. The method according to claim 1, wherein the process further includes the following step (4):

(4) a step of subjecting the collected conditioned medium to at least one treatment selected from the group consisting of centrifugation, concentration, solvent substitution, dialysis, freezing, drying, freeze-drying, dilution, desalting and storage.

13. The method according to claim 1, wherein the process further includes one of the following steps (a) or (b):

(a) a step of checking the collected conditioned medium with respect to the presence or absence of a neurite outgrowth activity in the presence of a nerve regeneration inhibitory substance; or
(b) a step of checking the collected conditioned medium with respect to the presence or absence of an apoptosis inhibitory activity toward neuronal cells.

14. The method according to claim 1, wherein the dental pulp stem cell-conditioned medium is a conditioned medium of a stem cell from human exfoliated deciduous teeth.

15. The method according to claim 1, wherein the target tissue is spinal cord.

16. The method according to claim 1, wherein the patient is a spinal cord injury patient.

17. The method according to claim 1, wherein the patient is a spinal cord injury patient and the target tissue is spinal cord.

18. The method according to claim 1, wherein the dental pulp stem cell-conditioned medium is administered by local administration.

19. The method according to claim 1, wherein the dental pulp stem cell-conditioned medium is administered by intravenous administration.

* * * * *